US008791092B2

(12) United States Patent
Bitan et al.

(10) Patent No.: US 8,791,092 B2
(45) Date of Patent: Jul. 29, 2014

(54) MOLECULAR TWEEZERS FOR THE TREATMENT OF AMYLOID-RELATED DISEASES

(75) Inventors: Gal Bitan, Los Angeles, CA (US); Akila Shanmugam, Allen, TX (US); Aleksey Lomakin, Swampscott, MA (US); Thomas Schrader, Mettmann (DE); Frank Gerrit Klarner, Bochum (DE); Peter Talbiersky, Krems (AT); Jolanta Polkowska, Essen (DE); Frank Bastkowski, Braunschweig (DE); Sharmistha Sinha, Ames, IA (US); Sally Frautschy, Santa Monica, CA (US)

(73) Assignees: The Regents of the University of California, Oakland, CA (US); The United States of America as represented by the Department of Veterans Affairs, Washington, DC (US); Massachusetts Institute of Technology, Cambridge, MA (US); Universitat Duisburg-Essen, Essen (DE)

( * ) Notice: Subject to any disclaimer, the term of this patent is extended or adjusted under 35 U.S.C. 154(b) by 59 days.

(21) Appl. No.: 13/203,962

(22) PCT Filed: Mar. 5, 2010

(86) PCT No.: PCT/US2010/026419
§ 371 (c)(1),
(2), (4) Date: Jan. 9, 2012

(87) PCT Pub. No.: WO2010/102248
PCT Pub. Date: Sep. 10, 2010

(65) Prior Publication Data
US 2012/0108548 A1    May 3, 2012

Related U.S. Application Data

(60) Provisional application No. 61/157,597, filed on Mar. 5, 2009.

(51) Int. Cl.
A61K 31/6615  (2006.01)
A61K 31/663   (2006.01)
C07K 14/47    (2006.01)
C07F 9/40     (2006.01)
C07F 9/12     (2006.01)

(52) U.S. Cl.
USPC ............................ 514/107; 558/162; 530/410

(58) Field of Classification Search
USPC ............................ 514/107; 558/162; 530/410
See application file for complete search history.

(56) References Cited

FOREIGN PATENT DOCUMENTS

WO    WO 2006/056182    6/2006
WO    WO 2010/102248    9/2010

OTHER PUBLICATIONS

Fokkens et al., Selective Complexation of N-Alkylpyridinium Salts: Binding of NAD+ in Water, 2005, Chem. Eur. J., 11, 477-494.*

(Continued)

Primary Examiner — Kristin Vajda
(74) Attorney, Agent, or Firm — Tom Hunter; Weaver Austin Villeneuve & Sampson LLP

(57) ABSTRACT

This invention provides novel compositions to inhibit the aggregation of amyloid proteins. In various embodiments the compositions comprise a molecular tweezers that binds lysine and/or arginine and thereby inhibits the aggregation of amyloidogenic proteins.

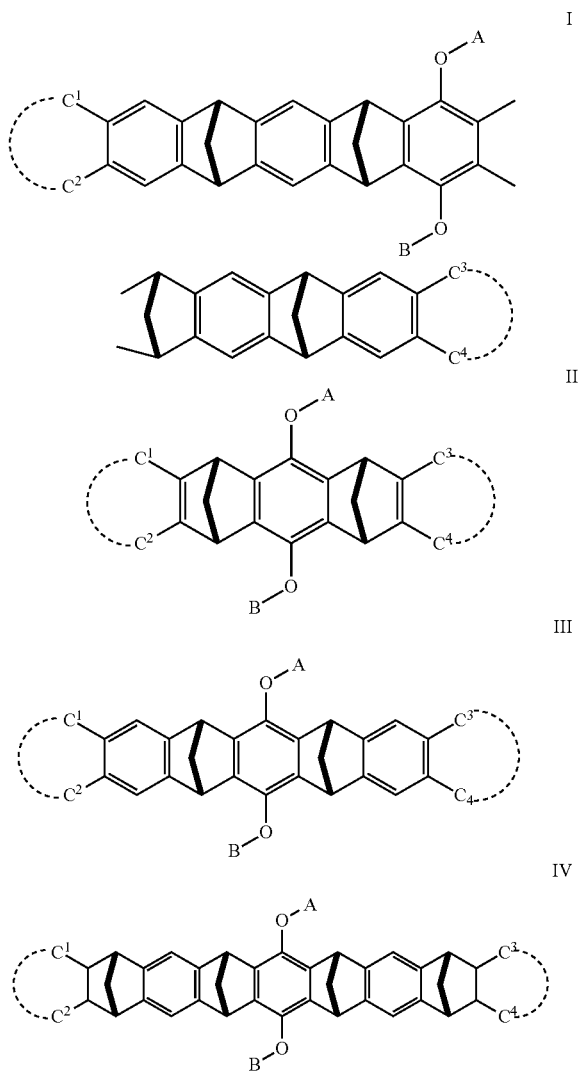

13 Claims, 22 Drawing Sheets

(56) References Cited

OTHER PUBLICATIONS

PCT International Search Report and Written Opinion dated Sep. 9, 2010 issued in PCT/US2010/026419 (P047WO).
PCT International Preliminary Report on Patentability dated Sep. 6, 2011 issued in PCT/US2010/026419 (P047WO).
EP Office Action dated Dec. 12, 2012 issued in EP10708075.6.
Branchi et al. (2008) "Fluorescent water-soluble molecular clips. Self-association and formation of adducts in aqueous and methanol solutions" *New Journal of Chemistry* 33(2): 397-407.
Dutt et al. (2013) "Molecular Tweezers with Varying Anions: A Comparative Study" *Journal of Organic Chemistry* 78 (13): 6721-6734.
Fokkens et al. (2005) "A Molecular Tweezer for Lysine and Arginine" Journal of the American Chemical Society 127(41): 14415-14421.
Gersthagen et al. (2013) "Ditopic Arginine-Aspartate Binders Recognize RGD Loops" *Eur. J. Org. Chem.* 1080-1092.
Gomes et al. (2009) "Host-Guest Interactions between Molecular Clips and Multistate Systems Based on Flavylium Salts" *Journal of the American Chemical Society* 131(25): 8922-8938.
Jasper et al. (2012) "Selective Complexation of N-Alkylpyridinium Salts: Recognition of NAD+ in Water" *Angewandte Chemie. Intl Edition* 41(8):1355-1358.
Kirsch et al. (2009) "A mechanism of efficient G6PD inhibition by a molecular clip" *Angewandte Chemie, Intl. Edition* 48(16): 2886-2890.
Klarner et al. (2003) "Molecular Tweezers and Clips as Synthetic Receptors. Molecular Recognition and Dynamics in Receptor-Substrate Complexes" *Accounts of Chemical Research* 36(12): 919-932.
Klarner et al. (1996) "Molecular Tweezers as Synthetic Receptors in Host-Guest Chemistry: Inclusion of Cyclohexane and Self-Assembly of Aliphatic Side Chains" *Angewandte Chemie, Intl. Edition* 35(10): 1130-1133.
Klarner et al. (2000) "Molecular tweezers as synthetic receptors: molecular recognition of neutral and cationic aromatic substrates. A comparison between the supramolecular structures in crystal and in solution" *J. Phys. Org. Chem.* 13: 604-611.
Klarner et al. (2004) "Effect of Substituents on the Complexation of Aromatic and Quinoid Substrates with Molecular Tweezers and Clips" *Eur. J. Org. Chem.* 1405-1423.
Polkowska et al. (2009) "A combined experimental and theoretical study of the pH-dependent binding mode of NAD+ by water-soluble molecular clips" *Journal of Physical Organic Chemistry* 22(8): 779-790.
Schrader et al. (2005) "Inclusion of Thiamine Diphosphate and S-Adenosylmethionine at Their Chemically Active Sites" *Journal of Organic Chemistry* 70(25): 10227-10237.
Talbiersky et al. (2008) "Molecular Clip and Tweezer Introduce New Mechanisms of Enzyme Inhibition" *Journal of the American Chemical Society* 130(30): 9824-9828.

\* cited by examiner

Scheme 1

Scheme 3

*Scheme 4*

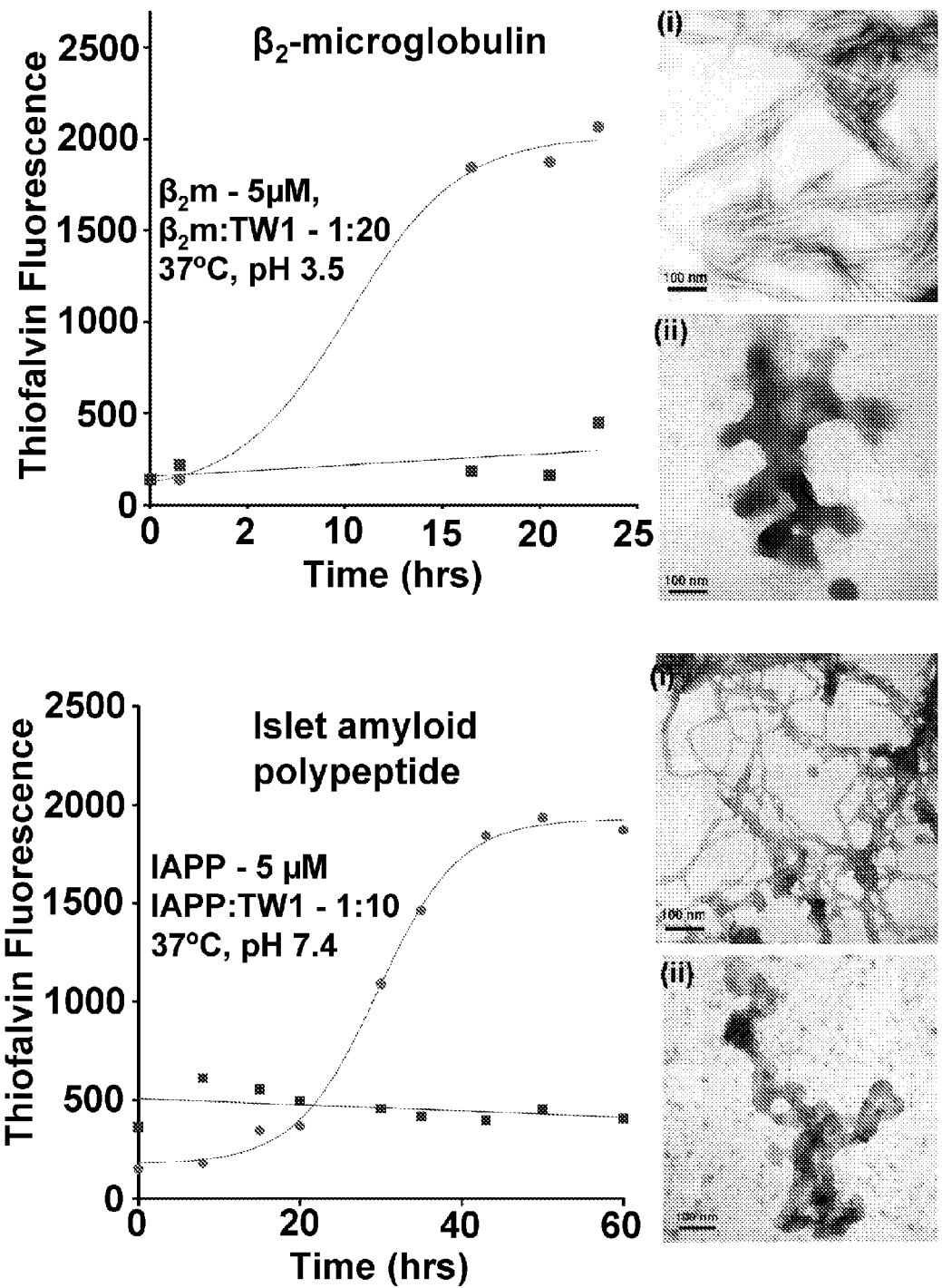
*Fig. 18, cont'd.*

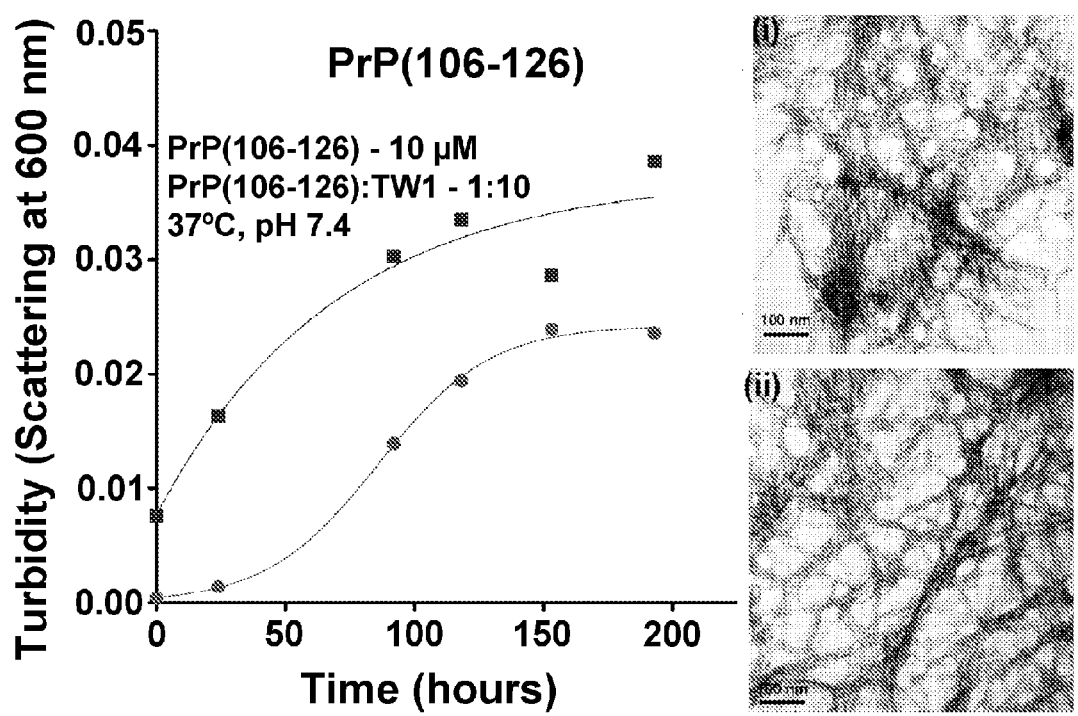
Fig. 18, cont'd.

3. Examples of potential Y groups:
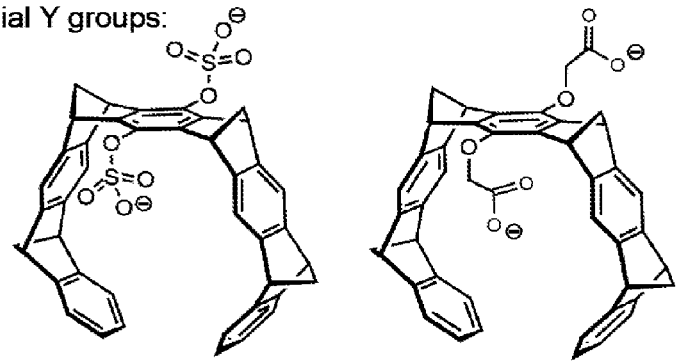
4. Examples of auxiliary groups conferring specificity for particular proteins:
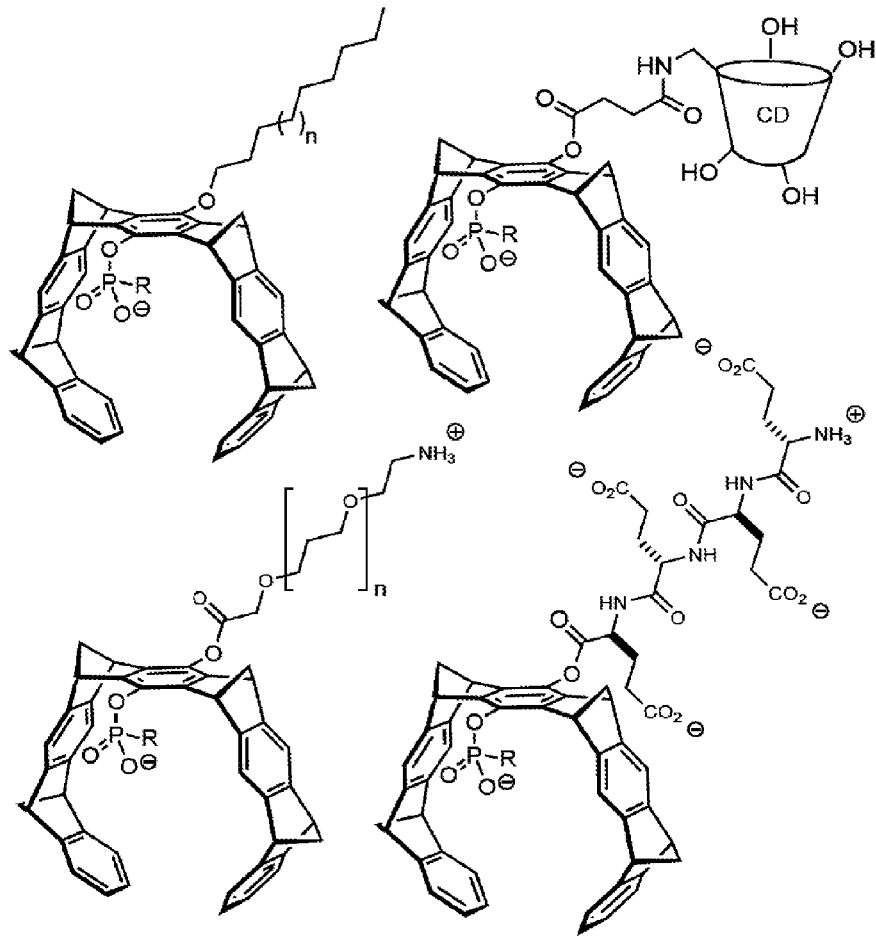
*Fig. 19, cont'd.*

4. Examples of auxiliary groups conferring specificity for particular proteins (continued):
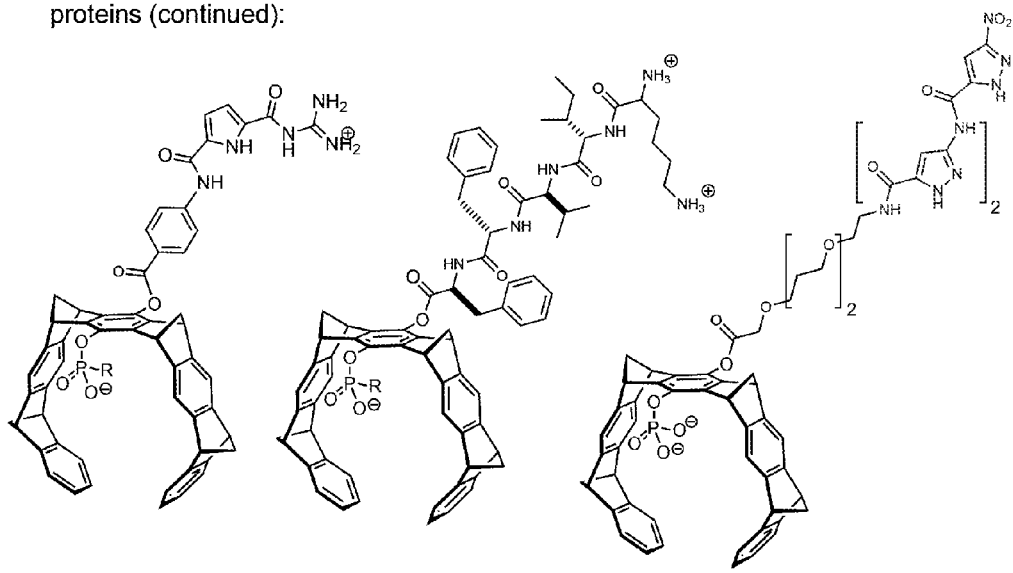
5. Tethered derivatives
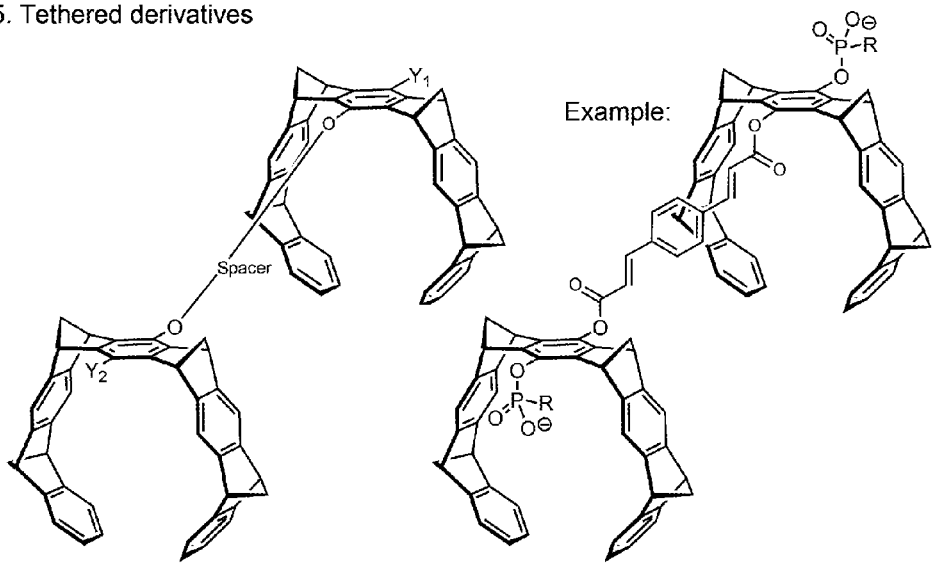
*Fig. 19, cont'd.*

MOLECULAR TWEEZERS FOR THE TREATMENT OF AMYLOID-RELATED DISEASES

STATEMENT OF GOVERNMENTAL SUPPORT

This work was supported by the U.S. Department of Veterans Affairs, and the Federal Government has certain rights in the invention.

CROSS-REFERENCE TO RELATED APPLICATIONS

This application is a 371 National Phase of PCT/US2010/026419, filed on Mar. 5, 2010, which claims priority to and benefit of U.S. Ser. No. 61/157,597, filed on Mar. 5, 2009, both of which are incorporated herein by reference in their entirety for all purposes.

FIELD OF THE INVENTION

The present invention relates to methods and composition for the treatment of disorders associated with amyloidosis. In particular, in certain embodiments, molecular tweezers are provided that are useful to inhibit aggregation of amyloidotic proteins.

BACKGROUND OF THE INVENTION

A number of diseases, including, for example Alzheimer's disease (AD) are associated with amyloidosis, a pathogenic process of protein or peptide misfolding and aggregation. The amyloid deposits present in these diseases consist of particular peptides or proteins that are characteristic for each of these diseases but regardless of the particular amino acid sequence of the peptides or proteins involved in each pathology, the amyloid fibrils have a characteristic β-sheet structure and generally share a common aggregation pathway.

In each disease, characterized by amyloidosis, a specific protein or peptide misfolds and/or oligomerizes to form soluble aggregation intermediates, and adopts β-sheet structure en route to fibril formation ultimately forming insoluble amyloid fibers, plaques or inclusions. These insoluble forms of the aggregated protein or peptide form by the intermolecular association of β-strands into β-sheets. Recent evidence suggests that the soluble amyloid oligomers may be the principal cause of toxicity.

To date, amyloid-related disorders cannot be cured or prevented. Alzheimer's disease (AD) often is considered as an archetype amyloid-related disease (Monien et al. (2006) *Expert Rev. Neurother.* 6: 1293-1306). Currently approved drugs for AD treat the symptoms, rather than the causes of the disease and provide only moderate and temporary relief (Shanmugam et al. (2008) *Development in Diagnostic and Therapeutic Strategies for Alzheimer's Disease*. Pp. 193-250 In: *Research Progress in Alzheimer's Disease and Dementia*, Vol. 3 (Ed. Sun, M.-K.), Nova Science Publishers, Inc.). AD is the leading cause of dementia and one of the leading causes of death among elderly people (Alzheimer's Disease Supersedes Diabetes As Sixth Leading Cause Of Death In The United States. (Medical News Today, 2008)). In the general population, AD is the 6$^{th}$ cause of death (Id.). A recent report by the Alzheimer Association has suggested that in 2007, the prevalence of AD in the US exceeded 5 million and may increase to 16 million by the middle of the century if no cure is found (see, e.g., (2007) Every 72 seconds someone in America develops Alzheimer's. http://www.alz.org/news-_and_events_rates_rise.asp). As the population ages, this situation may lead to an epidemic. Current estimates of cost of care for patients with AD in the US are over $148 billion a year (Id.). Globally, the prevalence of AD is estimated at ~27 million patients (Maslow et al. (2008) *Alzheimer's & Dementia* 4(2): 110-133).

Following the modified Amyloid Cascade Hypothesis (Hardy and Selkoe (2002) *Science* 297: 353-356), leading strategies have focused on Aβ as a primary cause of AD and therefore target inhibition of Aβ production, enhancement of Aβ clearance, or disruption of Aβ assembly. The normal physiologic function of Aβ is unknown, thus inhibiting its production or increasing its clearance may lead to adverse side effects. In fact, very recent data show that depletion of Aβ from rodent brain results in cognitive deficits, that can be rescued with sub-nM concentrations of human Aβ, demonstrating that at low concentration, Aβ is essential for normal brain function (Arancio, O., *Amyloid-β: From physiology to pathology* (S2-02-04); Mathews, P. M., *Endogenous Aβ enhances memory retention in the rat* (O2-02-01), International Conference on Alzheimer's Disease, Chicago, 2008). At higher concentrations, such as those that occur in the brains of people with AD, Down's syndrome, or cerebral amyloid angiopathy (CAA), Aβ self-association into oligomers and polymers is purely a pathologic phenomenon and therefore is an attractive target for development of inhibitors (Selkoe (2001) *Physiol. Rev.* 81: 741-766).

Aβ is produced as a non-toxic, "naturally unstructured" monomeric protein. With aging, Aβ accumulates and self-assembles into highly neurotoxic, soluble oligomers. The oligomers injure susceptible neurons and go on to form polymers that precipitate in the brain as amyloid plaques—one of the pathologic hallmarks of AD.

Because historically, Aβ polymers have been known for a long time and had been thought to be the cause of AD, multiple examples of small molecule inhibitors of Aβ fibrillization exist in the literature (Soto and Estrada (2005) *Subcell. Biochem.* 38: 351-364). Recently, following a paradigm shift in the amyloid field that identified pre-fibrillar oligomers as the primary cause of cytotoxicity (Kirkitadze et al. (2002) *J. Neurosci. Res.* 69: 567-577), several groups reported inhibitors of Aβ oligomeriztion (Wang et al. (2004) *J. Med. Chem.* 47: 3329-3333; Walsh et al. (2005) *J. Neurosci.* 25: 2455-2462; Yang et al. (2005) *J. Biol. Chem.* 280: 5892-5901; Necula et al. (2007) *J. Biol. Chem.* 282, 10311-10324; McLaurin et al. (2006) *Nat. Med.* 12, 801-808; Ehrnhoefer et al. (2008) *Nat Struct Mol Biol* 15, 558-566). Inhibitor selection in these studies was based on empirical findings, however, rather than structure-based rational design. Therefore, little can be deduced about their mechanism of action. In contrast, structure-based inhibitor design approaches can provide mechanistic data that can be used to improve inhibitor efficacy and pharmacokinetics.

SUMMARY OF THE INVENTION

In various embodiments, molecular tweezers are provided that are useful in the prevention and treatment of disorders associated with amyloidosis, a pathogenic process of protein or peptide misfolding and aggregation. Various tweezers include, but are not limited to, the molecular tweezers of Formulas I, II, III, or IV shown herein. Accordingly, in certain embodiments, there is provided a molecular tweezers as defined in claim 1 and further advantageous embodiments are the subject matter of the respective dependent claims.

In certain embodiments pharmaceutical formulations are also provided where the formulations comprise one or more of the molecular tweezers described herein and a pharmaceutically acceptable excipient. In certain embodiments the formulation is formulated for administration via a route selected from the group consisting of intraperitoneal administration, topical administration, oral administration, inhalation administration, transdermal administration, subdermal depot administration, sub-dural administration, and rectal administration. In certain embodiments the formulation is a unit dosage formulation. Accordingly, in certain embodiments, there is provided a pharmaceutical formulation as defined in claim 11 and further advantageous embodiments are the subject matter of the respective dependent claims.

Certain embodiments provide the use of molecular tweezers to inhibit the aggregation of amyloidogenic proteins. In certain embodiments the molecular tweezers binds lysine and/or arginine. In certain embodiments the molecular tweezers is a molecular tweezers as described herein. In certain embodiments the amyloidogenic proteins comprise one or more amyloidogenic proteins listed in Table 1. In certain embodiments the amyloidogenic proteins comprise one or more amyloidogenic proteins selected from the group consisting of calcitonin, β2-microglobulin (β2m), insulin, islet amyloid polypeptide (IAPP), and the neurotoxic prion protein (PrP) fragment$^{106-126}$. In certain embodiments the molecular tweezers is administered in a therapeutically effective amount. Accordingly, in certain embodiments, there is provided a use as defined in claim 14, and further advantageous embodiments are the subject matter of the respective dependent claims.

Also provided is the use of a molecular tweezers in the manufacture of a medicament or pharmaceutical composition to inhibit the aggregation of amyloidogenic proteins. In certain embodiments the molecular tweezers binds lysine and/or arginine. In certain embodiments the molecular tweezers is a molecular tweezers as described herein. In certain embodiments the amyloidogenic proteins comprise one or more amyloidogenic proteins listed in Table 1. In certain embodiments the amyloidogenic proteins comprise one or more amyloidogenic proteins selected from the group consisting of calcitonin, β2-microglobulin (β2m), insulin, islet amyloid polypeptide (IAPP), and the neurotoxic prion protein (PrP) fragment$^{106-126}$. In certain embodiments the molecular tweezers is administered in a therapeutically effective amount. Accordingly, in certain embodiments, there is provided a use as defined in claim 20, and further advantageous embodiments are the subject matter of the respective dependent claims.

Also provided in certain embodiments is the use of a molecular tweezers to inhibit amyloidosis. In various embodiments the molecular tweezers binds guest amino acid such as lysine and/or arginine. In certain embodiments the molecular tweezers is a molecular tweezers of Formulas I, II, III, or IV as shown herein. In various embodiments the molecular tweezers binds the guest amino acids listed in Table 2. In certain embodiments the molecular tweezers is a molecular tweezer from Table 2. In certain embodiments the amyloidosis is associated with a pathology selected from the diseases listed in Table 1. In certain embodiments the said molecular tweezers is administered in a therapeutically effective amount. Accordingly, in certain embodiments, there is provided a use as defined in claim 25, and further advantageous embodiments are the subject matter of the respective dependent claims.

In various embodiments the use of a molecular tweezers in the manufacture of a medicament or pharmaceutical composition to inhibit amyloidosis is provided. In various embodiments the molecular tweezers binds guest amino acid such as lysine and/or arginine. In certain embodiments the molecular tweezers is a molecular tweezers of Formulas I, II, III, or IV as shown herein. In various embodiments the molecular tweezers binds the guest amino acids listed in Table 2. In certain embodiments the molecular tweezers is a molecular tweezer from Table 2. In certain embodiments the amyloidosis is associated with a pathology selected from the diseases listed in Table 1. In certain embodiments the said molecular tweezers is formulated in a unit dosage formulation. Accordingly, in certain embodiments, there is provided a use as defined in claim 30, and further advantageous embodiments are the subject matter of the respective dependent claims.

In various embodiments the use of a molecular tweezers in the manufacture of a medicament or pharmaceutical to treat one or more of the diseases listed in Table 1 is provided. Also provided is the use of a molecular tweezers in the manufacture of a medicament or pharmaceutical composition for the prophylactic and/or curative treatment of amyloid-related disorders as listed in Table 1.

In various embodiments the use of one or more molecular tweezers described herein in pharmacology and/or medicine is provided.

In various embodiments methods are also provided for mitigating a symptom of a disease characterized by amyloidosis. The methods typically involve administering to a subject in need thereof a molecular tweezers that inhibits aggregation of an amyloidogenic protein in an amount sufficient to partially or fully inhibit aggregation of said amyloidogenic protein. In certain embodiments the disease is a disease selected from the diseases listed in Table 1. In certain embodiments the amyloidogenic protein is an amyloidogenic protein selected from the amyloidogenic proteins listed in Table 1. In certain embodiments the molecular tweezers is a molecular tweezers that binds lysine and/or arginine. In certain embodiments the molecular tweezers is a molecular tweezers of Formulas I, II, III, or IV as described herein. In various embodiments the molecular tweezers binds the guest amino acids listed in Table 2. In certain embodiments the molecular tweezers is a molecular tweezer from Table 2. Accordingly, in certain embodiments, there is provided a use as defined in claim 37, and further advantageous embodiments are the subject matter of the respective dependent claims.

In various embodiments methods are provided for inhibiting (completely or partially) the aggregation of amyloidogenic peptides/proteins. In various embodiments the methods involve administering one or more molecular tweezers (e.g., as described herein) to a mammal (human or non-human mammal) in need thereof, preferably in an amount to inhibit aggregation of amyloidogenic peptides/proteins. In certain embodiments the molecular tweezers is a molecular tweezers that binds lysine and/or arginine. In certain embodiments the molecular tweezers is a molecular tweezers of Formulas I, II, III, or IV as described herein. In various embodiments the molecular tweezers binds the guest amino acids listed in Table 2. In certain embodiments the molecular tweezers is a molecular tweezer from Table 2. In various embodiments the amyloidogenic proteins comprise one or more amyloidogenic proteins listed in Table 1. In certain embodiments the amyloidogenic proteins comprise one or more amyloidogenic proteins selected from the group consisting of calcitonin, β2-microglobulin (β2m), insulin, islet amyloid polypeptide (IAPP), and the neurotoxic prion protein (PrP) fragment$^{106-126}$. Accordingly, in certain embodiments, there is provided a method as defined in claim 43, and further advantageous embodiments are the subject matter of the respective dependent claims.

DEFINITIONS

The term "treatment of a pathology" refers to the amelioration of one or more symptoms associated with that pathology and/or slowing or stopping or reversal of the pathology, and/or the underlying physiology, and/or one or more of the symptoms associated therewith.

The terms "molecular tweezers" or "molecular clips", are noncyclic rigid polyaromatic beltlike molecules with open cavities capable of binding guests (e.g., amyloidogenic proteins in the present application). The open cavity of the molecular tweezers may bind guests using non-covalent bonding which includes hydrogen bonding, metal coordination, hydrophobic forces, van der Waals forces, $\pi$-$\pi$ interactions, and/or electrostatic effects. These molecules are a subset of polyaromatic molecular receptors and their structure is characterized by two "arms" that bind the guest molecule between them and only connected at one end.

The term "alkyl" used herein refers to a $C_1$-$C_{14}$, in various embodiments a $C_1$-$C_{10}$, and in certain embodiments a $C_1$-$C_6$ straight or branched saturated hydrocarbon group, including, for example, methyl, ethyl, n-propyl, iso-propyl, n-butyl, sec-butyl, iso-butyl, tert-butyl, etc.

The term "aryl" refers to an aromatic, unbranched, branched, and/or cyclic, and/or polycyclic hydrocarbon chain. In various embodiments, a $C_3$-$C_{14}$ or a $C_5$-$C_{14}$, in certain embodiments, a $C_5$-$C_{10}$, and in some embodiments a $C_5$-$C_6$, mono- or poly-cyclic aromatic ring, including, but not limited to, phenyl, naphthyl and the like. The aryl can be unsubstituted or have one or more substituent groups wherein the substituent group can include, for example, halogen, $C_{1-6}$ alkyl, $C_{1-6}$ halogenoalkyl, $C_{1-6}$ alkoxy, amino group, etc. In various embodiments the aryl can be neutral or positively or negatively charged.

The term "alkylphosphonate" refers to a salt of an alkylphosphonic acid anion.

The term "arylphosphonate" refers to a salt of an arylphosphonic acid anion.

The term "alkylphosphamide" refers to a salt of a phosphoric acid amide.

The term "arylphosphamide" refers to a salt of a phosphoric acid aryl amide.

The term "alkylcarboxylate" refers to a salt of an alkylcarboxylic acid.

Figure 14:
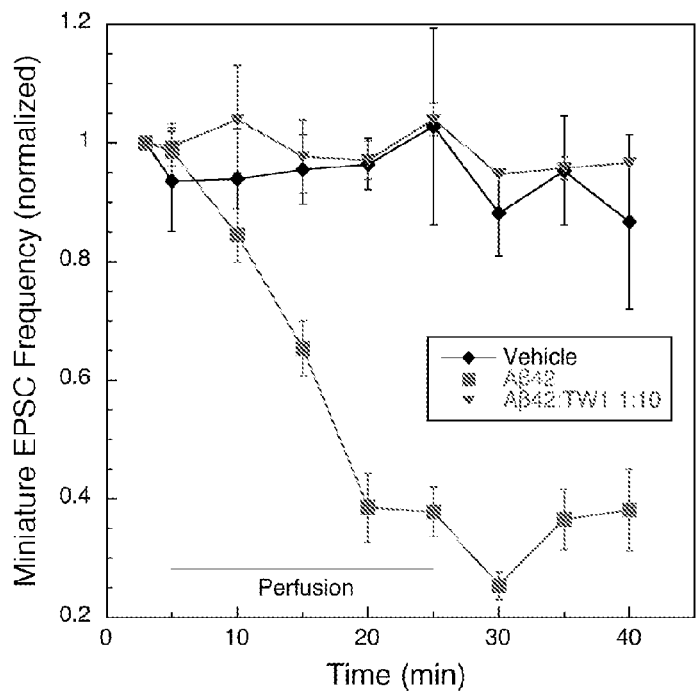

FIG. 14 shows that TW1 rescues Aβ-induced decrease in miniature excitatory post synaptic currents. Mouse primary hippocampal neurons were exposed to vehicle (n=5), 3 μM Aβ42 (n=8), or 1:10—Aβ42:TW1 (n=3) and the frequency and amplitude of mEPSCs were measured. Cells were perfused with vehicle for 5 min to establish baseline, and then with peptide or peptide:tweezers solutions for additional 20 minutes, and allowed to recover in vehicle solution for 15 minutes. The curves show the time-dependence of mEPSC frequency after exposure to Aβ42 in the absence or presence of CTFs over 40 minutes. TW1 rescues the toxic effect of Aβ42 to baseline level.

Figure 15:
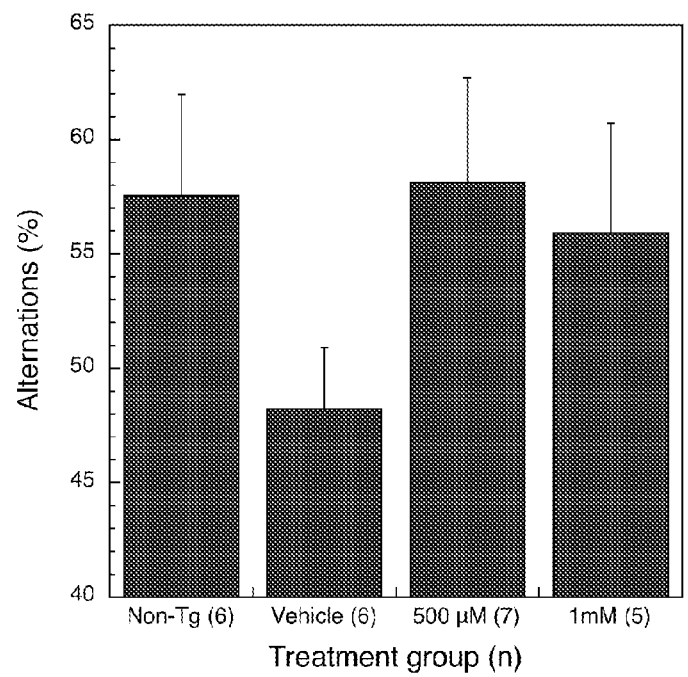

FIG. 15 shows that TW1 improves spatial memory in AD transgenic mice. Triple transgenic (Oddo et al, Neuron, 2003), 9-month old, mixed gender mice were treated with TW1 subcutaneously for 28 days. Both treatment groups show improvement in spatial memory relative to vehicle-treated transgenic mice to the level of wild-type, untreated mice.

Figure 16A:
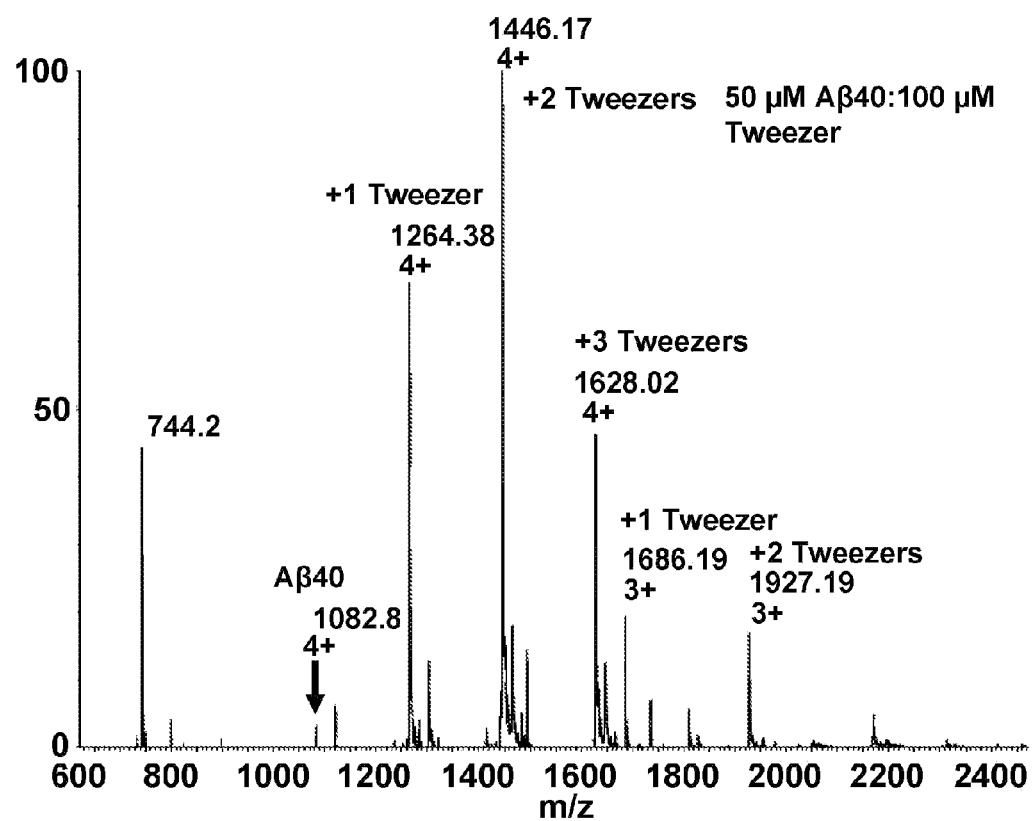
Figure 16B:
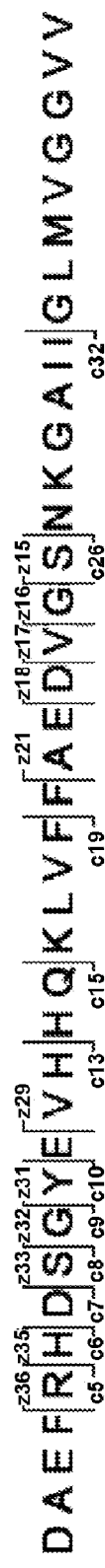
Figure 16B:
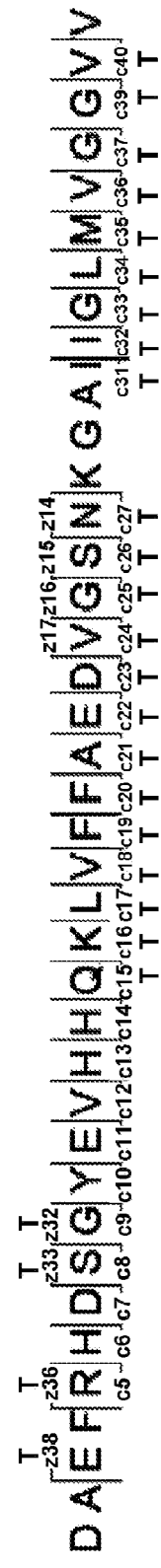

FIGS. 16A and 16B show that TW1 binds preferentially to Lys16. Aβ40:TW1 mixtures were analyzed by electrospray mass spectrometry ESI-MS. FIG. 16A: At 1:2 Aβ40:TW1 concentration ratio, the predominant complex contains 2 TW1 molecules per Aβ40 molecule. All stoichiometries are observed. FIG. 16B: At 1:1 Aβ40:TW1 concentration ratio, the predominant complex has a 1:1 stoichiometry (not shown). ECD applied under these conditions yields a mixture of free and tweezers-bound fragments. Analysis of these fragments reveals that in the 1:1 complex, TW1 is bound to Lys16.

Figure 17A:
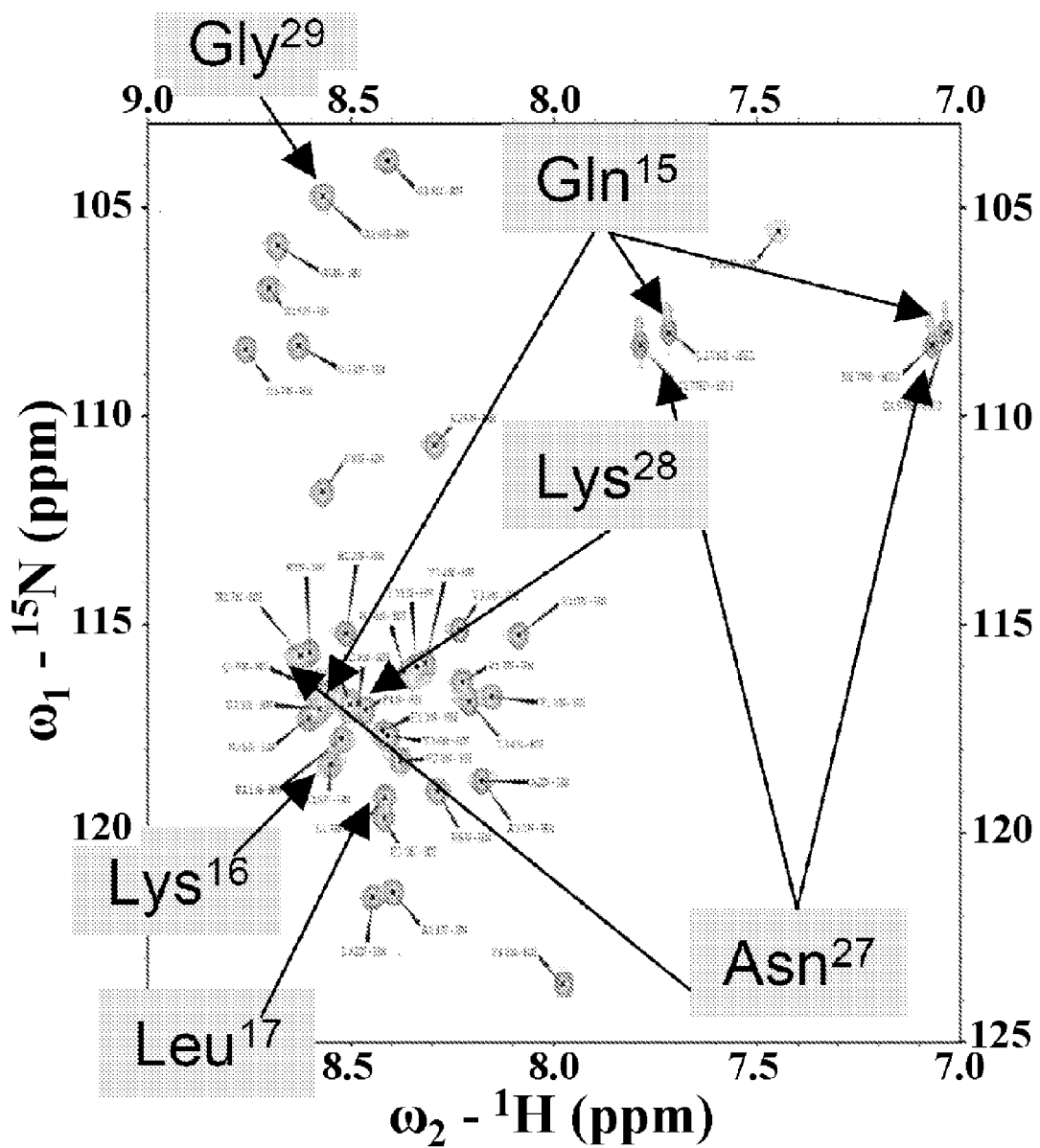
Figure 17B:
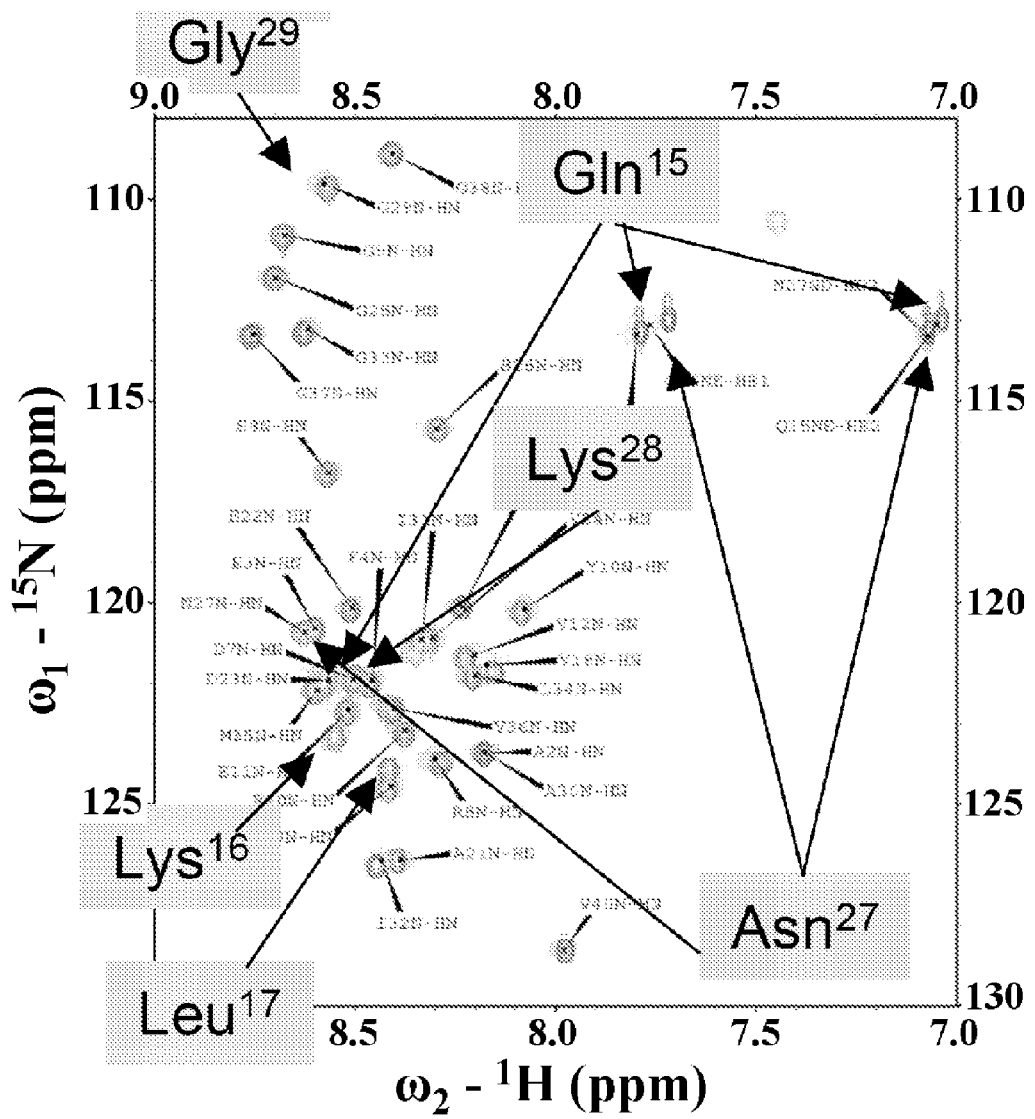
Figure 17C:
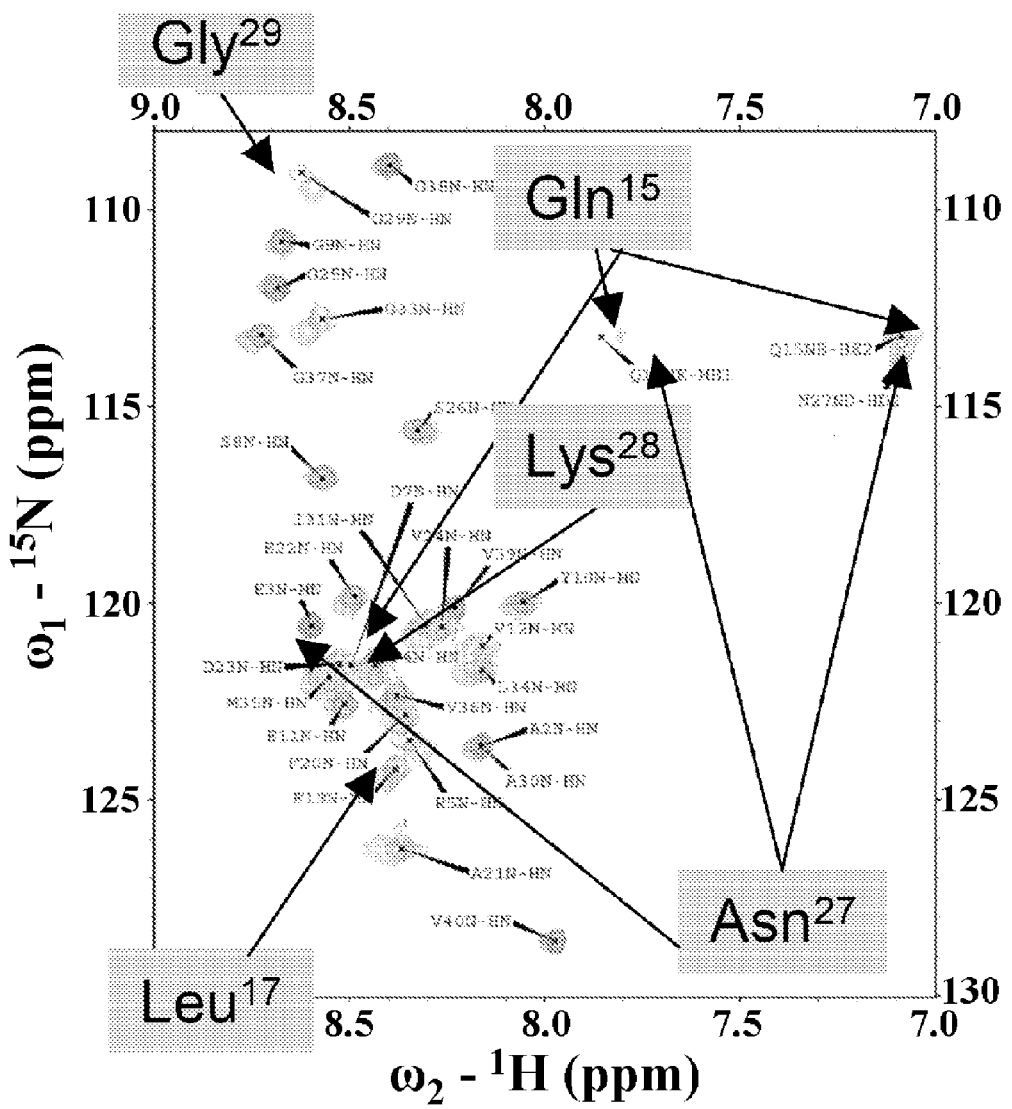

FIGS. 17A-17C indicate that TW1 binds to 3 sites in Aβ in the order Lys16, Lys28, Arg5. Aβ40:TW1 mixtures were analyzed by solution-state NMR using 2-dimentional heteronuclear single quantum correlation (HSQC). Aβ40 concentration was kept constant at 60 μM. FIG. 17A: Aβ alone. FIG. 17B: At 2:1 Aβ40:TW1 concentration ratio, strong reduction in peak intensity is observed around Lys16 and mild changes are observed around Lys28. FIG. 17C: At 1:2 Aβ40:TW1 concentration ratio, the peaks around Lys16 are virtually absent, multiple peak reduction/shifting is observed around Lys28, and milder effects are observed around Arg5.

Figure 18:
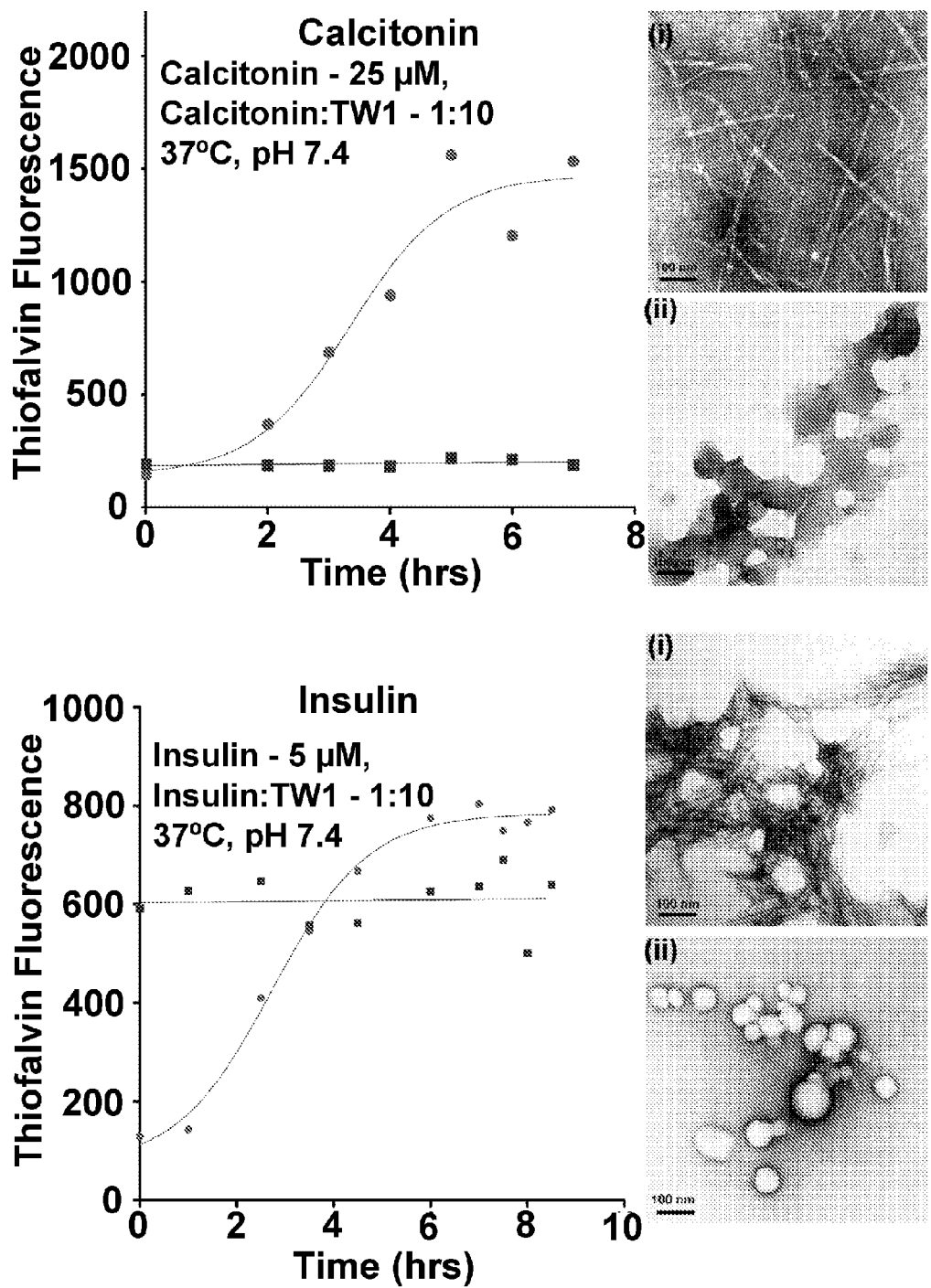

FIG. 18 shows that TW1 inhibits fibrillogenesis of amyloidogenic proteins other than Aβ. TW1 was mixed with each protein at 1:10 or 1:20 concentration ratio and incubated under conditions that induce fibril formation. The reaction was monitored by ThT fluorescence (squares) and compared to the protein incubated in the absence of TW1 (circles). PrP(106-126) was monitored using turbidity. Aliquots of each reaction were taken at the end of the reaction and examined by EM. TW1 inhibited the aggregation of calcitonin, β2m, insulin, and IAPP but not PrP(106-126).

Figure 19:
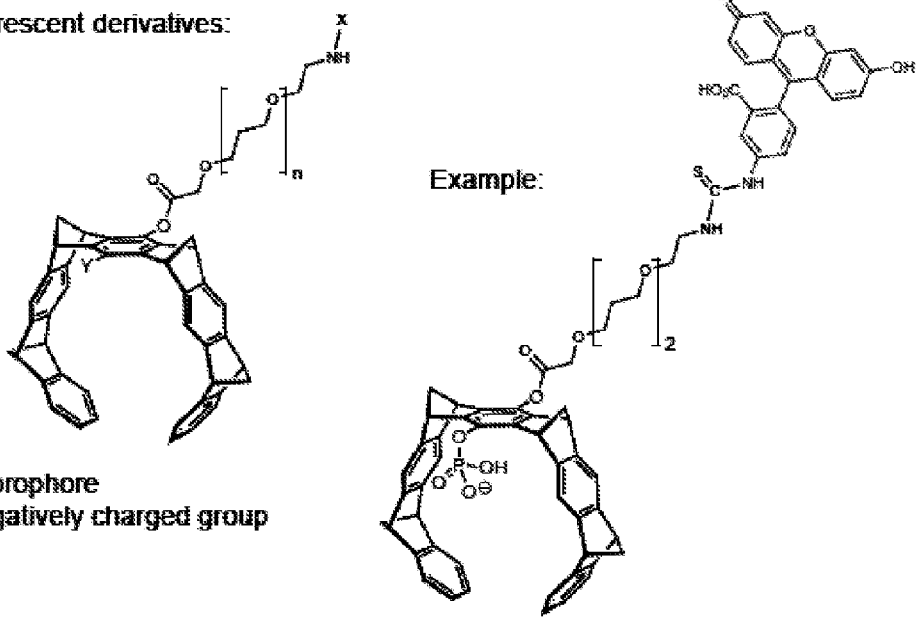

FIG. 19 illustrates various molecular tweezers.

DETAILED DESCRIPTION

In various embodiments, molecular tweezers are provided that are useful in the prevention and treatment of disorders associated with amyloidosis, a pathogenic process of protein or peptide misfolding and aggregation. The amyloid deposits present in these diseases consist of particular peptides or proteins that are characteristic for each of these diseases but regardless of their sequence the amyloid fibrils have a characteristic β-sheet structure and generally share a common aggregation pathway.

In each disease, a specific protein or peptide misfolds and/or oligomerizes to form soluble aggregation intermediates, and adopts β-sheet structure en route to fibril formation ultimately forming insoluble amyloid fibers, plaques or inclusions. These insoluble forms of the aggregated protein or peptide form by the intermolecular association of β-strands into β-sheets. Recent evidence suggests that the soluble amyloid oligomers may be the principal cause of toxicity. Table 1 describes each of a number amyloid related disorders and the corresponding amyloidogenic proteins involved.

TABLE 1

Illustrative amyloid related disorders and the corresponding amyloidogenic proteins involved.

| Disease | Amyloidogenic Proteins involved | References |
|---|---|---|
| Alzheimer's disease, Mild Cognitive Impairment (MCI) Cerebral Amyloid Angiopathy (CAA) | Aβ, tau | (1-4) |
| Down's Syndrom | | (5) |
| Age-related macular degeneration | Aβ | (6) |
| Familial Alzheimer's disease | Multiple mutation-containing variants of Aβ and tau | (7) |
| Finnish hereditary systemic amyloidosis | Gelsolin | (8) |
| Familial Danish Dementia | ADan | (9) |
| Familial British Dementia | ABri | |
| Type 2 diabetes | Islet amyloid polypeptide (amylin) | (10, 11) |
| Parkinson's disease | α-synuclein | (12) |
| Dementia with Lewy bodies | | (13) |
| Frontotemporal dementia | Tau | (14) |
| Huntington's disease | Huntingtin | (15) |
| Dentatombral Pallidoluysian Atrophy | Atrophin 1 | (16, 17) |
| spinocerebellar ataxia | Ataxin 1-3, TATA box-binding protein | (18, 19) |
| spinal and bulbar muscular atrophy/Kennedy's disease | Androgen receptor | (20) |
| Bovine Spongiform Encephalopathy Scrapie Kuru Gerstmann-Straussler-Scheinker disease Fatal familial insomnia Creutzfeldt- Jakob disease | Prion (PrP) | (21-23) |
| Dialysis-related amyloidosis | β₂-microglobulin | (24) |
| Secondary systemic amyloidosis | | (25, 26) |
| Systemic (reactive) AA amyloidosis | β₂-microglobulin, serum amyloid A | |
| Prostatic amyloidosis | β₂-microglobulin, transthyretin | (27, 28) |
| Conjunctival amyloidosis | Unknown deposits | (29) |
| Primary systemic amyloidosis | Insoluble monoclonal immunoglobulin | (30, 31) |
| Systemic AL amyloidosis | Immunoglobulin light chain | |
| Immunoglobulin heavy chain-associated amyloidosis | Immunoglobulin heavy chain | (32) |
| Nodular AL amyloidosis/Primary Sjoegren's Syndrome | Antinuclear antibodies | (33) |
| Myeloma-associated amyloidosis | Immunoglobulin | (34) |
| Nodular Glomerulosclerosis | | (35) |

TABLE 1-continued

Illustrative amyloid related disorders and the
corresponding amyloidogenic proteins involved.

| Disease | Amyloidogenic Proteins involved | References |
|---|---|---|
| Chronic inflammatory disease | $\beta_2$-microglobulin, serum amyloid A, immunoglobulin | (25, 26) |
| Hereditary non-neuropathic systemic amyloidosis | Lysozyme | (36) |
| Familial visceral amyloidosis | | (37) |
| Fibrinogen α-chain amyloidosis | Fibrinogen α-chain | (38) |
| Familial Mediterranean Fever | Serum amyloid A | (39) |
| Hereditary renal amyloidosis | Cystatin C | (40) |
| | Fibrinogen α-chain | (38) |
| | Gelsolin | (8) |
| Senile systemic amyloidosis Familial Amyloid Polyneuropathy/Corino de Andrade's disease Familial Cardia amyloidosis Familial oculo-leptomeningel amyloidosis | Transthyretin | (41-45) |
| Insulin-related amyloidosis/injection-localized amyloidosis | Insulin | (46) |
| Medullary Carcinoma of the thyroid | Calcitonin | (47) |
| Isolated atrial amyloidosis | Atrial natriuretic factor | (48) |
| Hereditary Cerebral amyloid angiopathy Hereditary Cerebral Hemorrhage with Amyloidosis (Icelandic) | Cystatin C | (40) |
| Familial amyotrophic lateral sclerosis | Superoxide dismutase 1 | (49) |

(1) Holtzman (2001) *J Mol Neurosci* 17: 147-155.
(2) Selkoe (2008) *Behav Brain Res* 192: 106-113.
(3) Butterfield et al. (2007) *Free Radic Biol Med* 43: 658-677.
(4) Thal et al. (2008) *Acta Neuropathol* 115: 599-609.
(5) Lott et al. (2006) *Curr Alzheimer Res* 3: 521-528.
(6) Wang et al (2008) *J Immunol* 181: 712-270.
(7) Krone et al. (2008) *J Mol Biol* 381: 221-228.
(8) Fadika and Baumann (2002) *Amyloid* 9: 75-82.
(9) Rostagno et al. (2005) *Cell Mol Life Sci* 62: 1814-1825.
(10) Johnson et al. (1989) *N Engl J Med* 321: 513-518.
(11) Kahn et al. (1999) *Diabetes* 48: 241-253.
(12) Baba et al. (1998) *Am J Pathol* 152: 879-884.
(13) Dodel et al. (2008) *J Neural* 255 Suppl 5: 39-47.
(14) Goux et al. (2004) *J Biol Chem* 279: 26868-26875.
(15) Scherzinger et al. (1999) *Proc. Natl. Acad. Sci. USA* 96: 4604-9460.
(16) Kanazawa (1999) *Philos Trans R Soc Lond B Biol Sci* 354: 1069-1074.
(17) Yamada et al. (2006) *Neuropathology* 26: 346-351.
(18) Manto (2005) *Cerebellum* 4: 2-6.
(19) Orr and Zoghbi (2001) *Hum Mol Genet* 10: 2307-2311.
(20) Davies et al (2008) *J Mol Endocrinol.*, 41(5): 301-314.
(21) Collinge (1997) *Hum Mol Genet* 6: 1699-705.
(22) Prusiner (1993) *Dev Biol Stand* 80: 31-44.
(23) Zou and Gambetti (2007) *Cell Mol Life Sci* 64: 3266-3270.
(24) Jahn et al. (2008) *J Biol Chem* 283: 17229-17286.
(25) DiBartola and Benson (1989) *J Vet Intern Med* 3: 31-41.
(26) Obici et al. (2005) *Biochim Biophys Acta* 1753: 11-22.
(27) Rocken et al. (1996) *Pathol Res Pract* 192: 998-1006.
(28) Cross et al. (1992) *J Clin Pathol* 45: 894-897.
(29) Demirci et al. (2006) *Surv Ophthalmol* 51: 419-433.
(30) Gertz and Rajkumar (2002) *Curr Treat Options Oncol* 3: 261-721.
(31) Sanchorawala (2006) *Clin J Am Soc Nephrol* 1: 1331-1341.
(32) Eulitz et al. (1990) *Proc. Natl. Acad. Sci. USA* 87: 6542-6546.
(33) Fox: R. I. (2005) Sjogren's syndrome. *Lancet* 366: 321-331.
(34) Shaheen et al. (2008) *Adv Anat Pathol* 15: 196-210.
(35) Ronco et al. (2006) *Clin J Am Soc Nephrol* 1: 1342-1350.
(36) Pepys et al. (1993) *Nature* 362: 553-557.
(37) Gillmore et al. (1999) *Nephrol Dial Transplant* 14: 2639-2644.
(38) Uemichi et al. (1994) *J Clin Invest* 93: 731-736.
(39) Ozen (2003) *Eur J Pediatr* 162: 449-454.
(40) Ghiso et al. (1986) *Proc. Natl. Acad. Sci. USA* 83: 2974-2978.
(41) Petersen et al. (1997) *Ann Neurol* 41: 307-313.
(42) Kelly (1996) *Curr Opin Struct Biol* 6: 11-17.
(43) Reixach et al. (2006) *Biochem Biophys Res Commun* 348: 889-897.
(44) Saraiva (1995) *Hum Mutat* 5: 191-196.
(45) Saraiva (2001) *FEBS Lett* 498: 201-203.
(46) Swift (2002) *Diabet Med* 19: 881-882.
(47) Dammrich et al. (1984) *Histochemistry* 81: 369-372.
(48) Torricelli et al. (2004) *J Mol Endocrinol* 33: 335-341.
(49) Banci et al. (2008) *PLoS ONE* 3: e1677.

It was a surprising discovery that the molecular tweezers described herein can inhibit the aggregation of amyloid proteins and thereby inhibit amyloidosis and consequently one or more of the symptoms associated with a pathology characterized by amyloidosis (e.g., pathologies listed in Table 1).

In particular, it was found that the molecular tweezers (TW1, see, e.g., FIG. 1) inhibited Aβ folding, aggregation and toxicity, both in vitro and in vivo, making it a promising lead compound for development of drugs for treatment of AD (and other pathologies characterized by amyloidosis). In contrast TW2 (see, FIG. 1), showed inhibition of Aβ aggregation similar to TW1 but was found to be toxic.

It was also demonstrated that TW1 inhibits the aggregation and fibril formation of several other amyloidogenic proteins (see Example 1). Based on these results, it is believed that molecular tweezers can be useful for inhibiting assembly and toxicity of amyloid forming proteins other than Aβ. More generally, it is believed that the tweezers scaffold(s) described herein provide a useful general platform for development of drugs targeting such proteins for treatment of amyloid-related diseases, including, but not limited to those listed in Table 1.

Accordingly, in certain embodiments, molecular tweezers useful for inhibiting the assembly and/or toxicity of amyloid forming proteins are provided herein. Illustrative molecular tweezers are shown for example, in FIG. 19. Pharmaceutical formulations comprising one or more molecular tweezers species are contemplated. In addition, uses of molecular tweezers for the inhibition of amyloidosis and/or the treatment of pathologies characterized by amyloidosis are also within the scope of the present invention as are the use of various molecular tweezers in the manufacture of a medicament to inhibit amyloidoisis, and/or to treat a pathology characterized by the formation of amyloid protein deposits.

Molecular Tweezers to Inhibit the Aggregation and/or Fibril Formation of Amyloidogenic Proteins.

Figure 1:
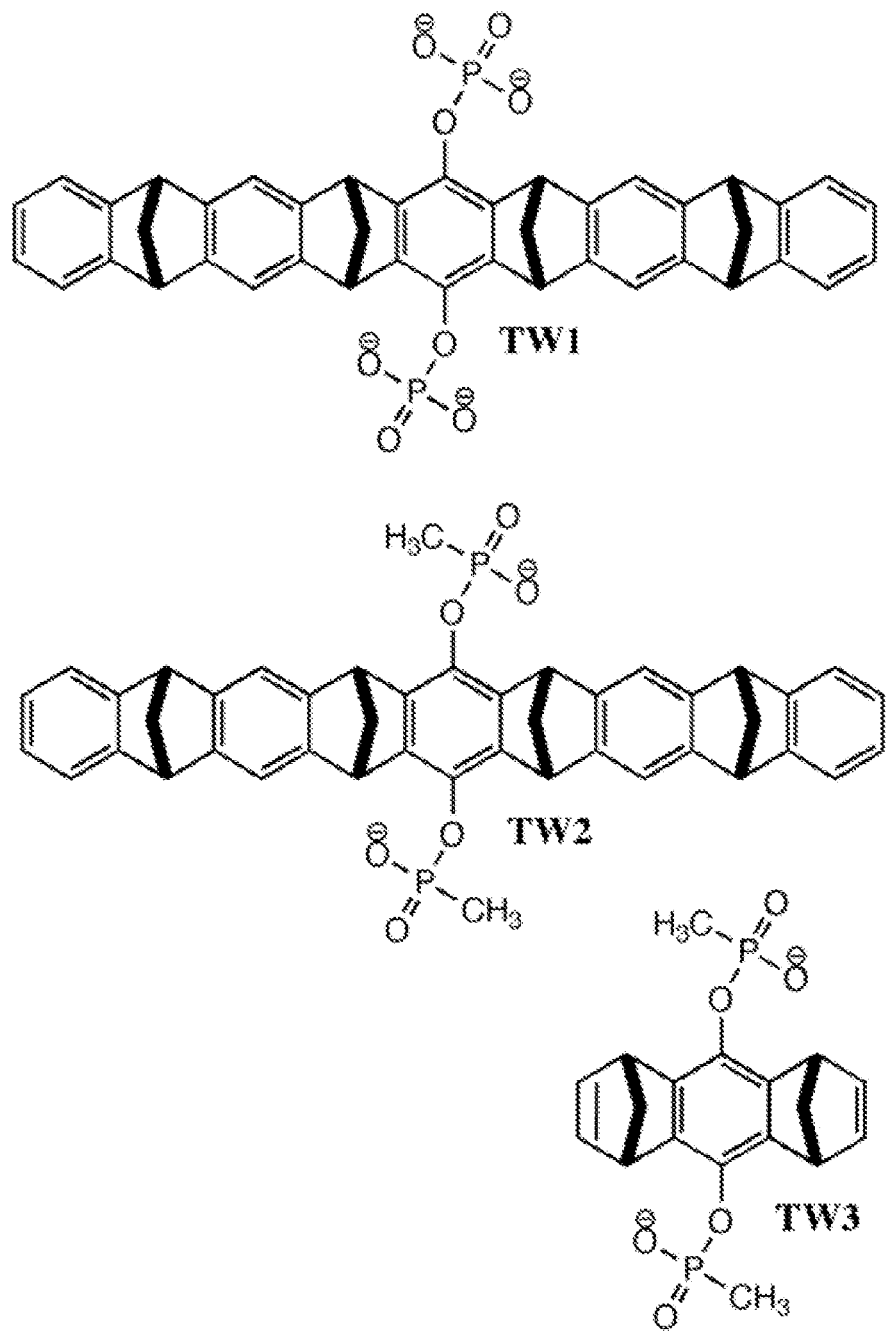
FIG. 1 illustrates various molecular tweezers described herein. The three derivatives are referred to as tweezers 1 (TW1), tweezers 2 (TW2), and tweezers 3 (TW3). A molecular tweezers is a tweezers-like molecule that can seize or complex one guest molecule. Two or more molecular tweezers are two or more independent tweezers molecules, that can seize or complex a total of two or more guest molecules.

In certain embodiments molecular tweezers are provided that inhibit the aggregation and/or fibril formation of amyloidogenic proteins. In addition compositions comprising one or more such molecular tweezers are also provided. In certain embodiments the molecular tweezers include molecular tweezers according to any of Formulas I, II, III, IV, or V:

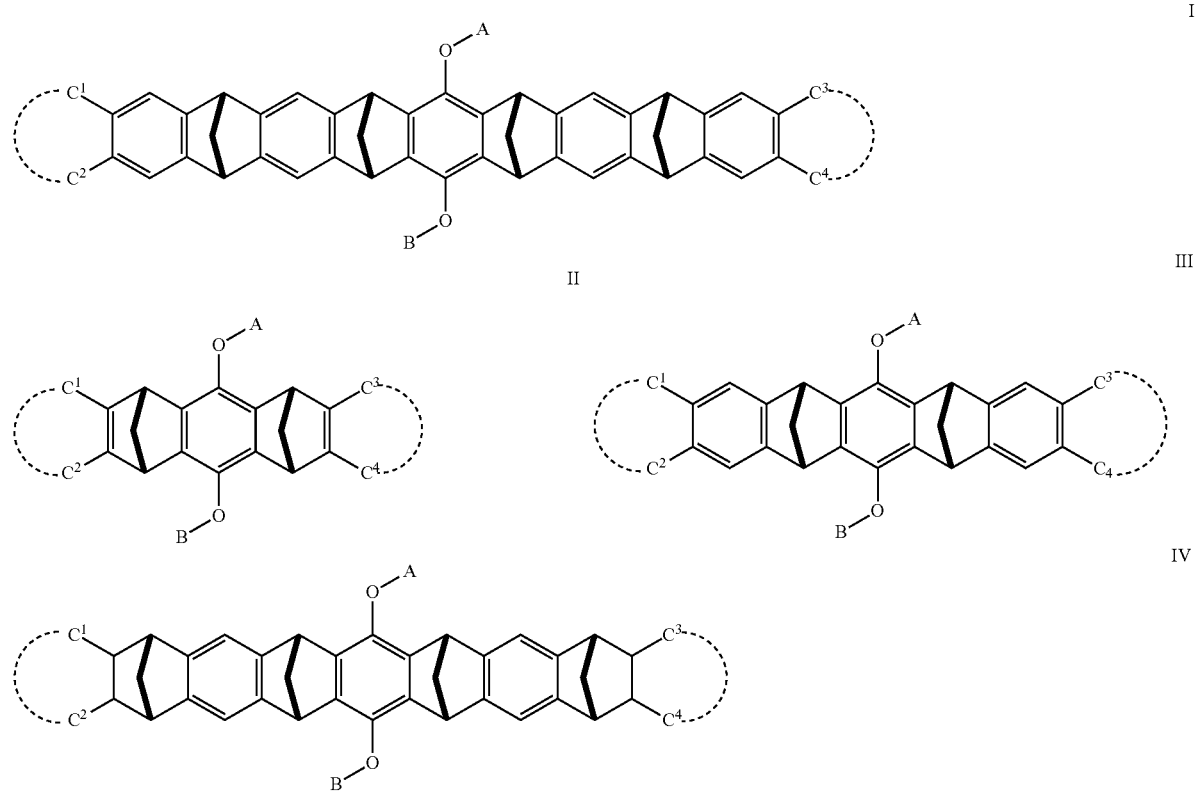

where $C^1$, $C^2$, $C^3$, and $C^4$ are independently selected from the group consisting of H, Cl, Br, I, OR, $NR_2$, $NO_2$, $CO_2H$, and $CO_2R$, where R is alkyl, aryl, or H. As illustrated by the dotted lines, in certain embodiments, $C^1$ and $C^2$ and/or well as $C^3$ and $C^4$ can also form an aliphatic or aromatic ring. A is selected from the group consisting of phosphate, hydrogen phosphate, alkylphosphonate, arylphosphonate, alkylphosphamide, arylphosphamide, sulfate, and alkylcarboxylate; B is selected from the group consisting of phosphate, hydrogen phosphate, alkylphosphonate, arylphosphonate, alkylphosphamide, arylphosphamide, sulfate, and alkylcarboxylate, or B has the formula —X—S—Y—Z where X is present or absent and when present is —(C═O)—; S is a spacer; Y is selected from the group consisting of an ester, an amide, a urethane, and a sulfonic ester link; and Z is selected from the group consisting of a detectable label, a protein, a nucleic acid, a sugar, and a glycoprotein; and, in various embodiments, said molecular tweezers does not have the formula of TW2 (e.g., as shown in FIG. 1). In certain embodiments $C^1$, $C^2$, $C^3$, and $C^4$ are all the same.

In certain embodiments A and/or B are selected from the group consisting of

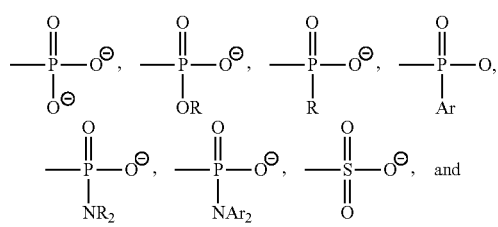

-continued

—$(CH_2)_n$—$CO_2^\ominus$ where R is alkyl or H; n ranges from 1 to 10, and Ar is aryl.

In certain embodiments B includes, but is not limited to:

B═—X-Spacer-Y-Fluorescence Dye, or —X-Spacer-Y-Binding site

With X=nothing or —(C═O)—;

and Spacer=$C_1$-$C_{10}$ alkyl chain, or $C_2$-$C_{10}$ PEG chain, or $C_1$-$C_{10}$ arylalkyl chain;

and Y=any ester, amide, urethane, or sulfonic acid ester link such as —(C═O)O—, or —(C═O)NH—, or —O(C═O)—, or —NH(C═O), or —NH—(C═O/S)—NH, or —$OSO_2$—, or NH(C═O)O—, etc.

where fluorescence dye=any commercially available fluorescent dye; and binding site=any organic fragment. Examples include, but are not limited to:

B═—X-Spacer-Y-Fluorescence Dye;

B132

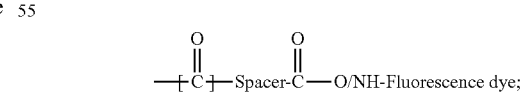

B2=

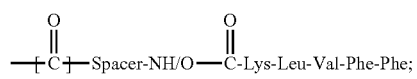

and

B3=

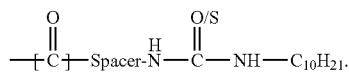

In certain embodiments formulas I, II, III, or IV expressly exclude the molecular tweezers species TW1, and/or TW2, and/or TW3.

Other illustrative, but non-limiting, molecular tweezers are shown in FIG. 19 and in Table 2. The foregoing molecular tweezers are intended to be illustrative and not limiting. Using the teaching provided herein, other molecular tweezers, for example, other molecular tweezers that bind lysine and/or arginine, can be identified by one of skill in the art.

TABLE 2

Illustrative guest amino acid(s) and their corresponding molecular tweezers.
References describing synthesis of tweezers are identified in brackets.

| Guest Amino Acid/ (Reference) | Molecular Tweezers |
|---|---|
| Arginine, Lysine | TW1<br>TW3 |
| Lysine (49) | |
| Lysine (50) | |
| Lysine (50) | |
| Lysine (51) | ns-curcubituril [6] |

TABLE 2-continued
Illustrative guest amino acid(s) and their corresponding molecular tweezers.
References describing synthesis of tweezers are identified in brackets.
| Guest Amino Acid/ (Reference) | Molecular Tweezers |
|---|---|
| Arginine (53) | 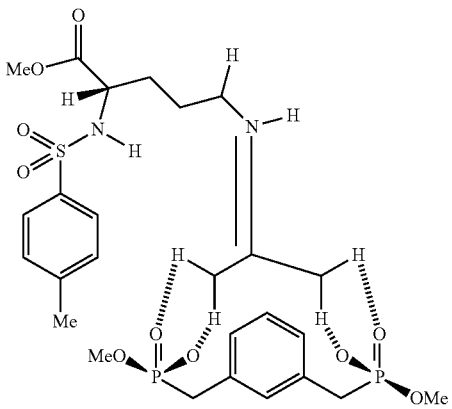 |
| Arginine (53) | 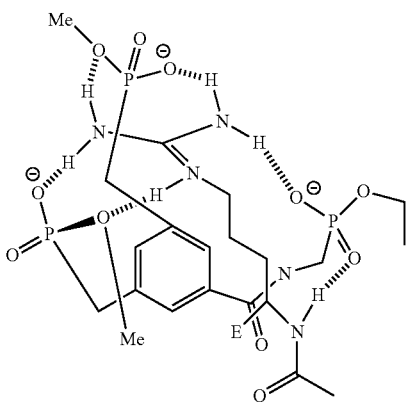 |
| Arginine (53) | 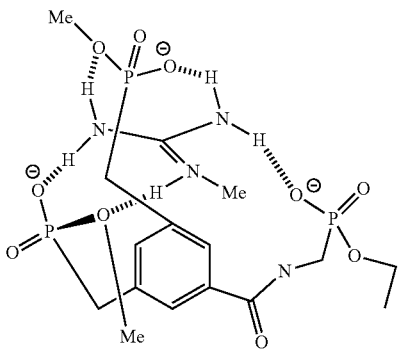 |
| Argnine (53) | 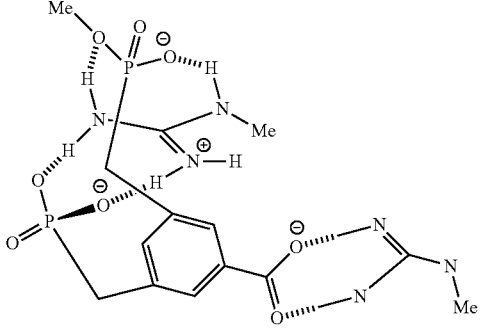 |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| Arginine, Lysine, X-Arg dipeptides (Aspartate, Glutamate) (54) | 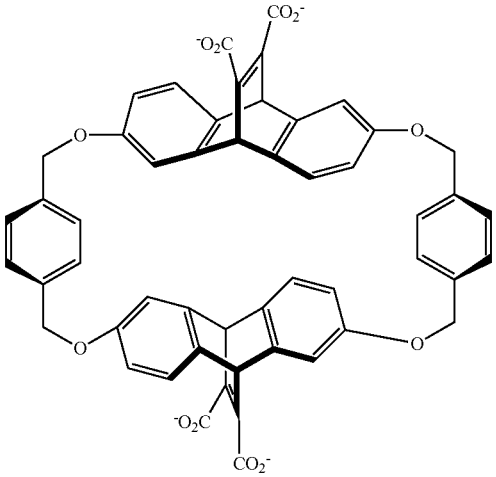 |
| Arginine, Lysine, X-Arg dipeptides (Aspartate, Glutamate) (54) | 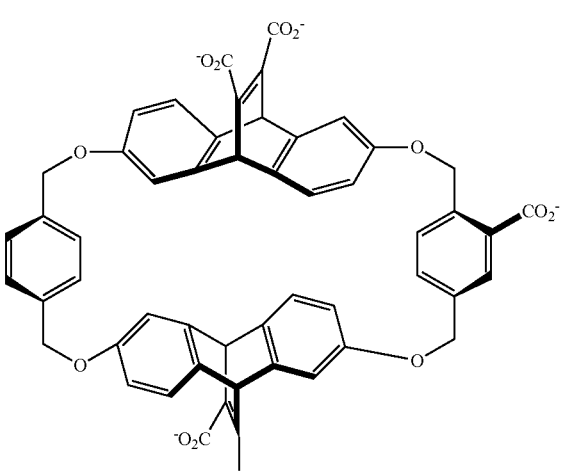 |
| Arginine, Lysine, X-Arg dipeptides (Aspartate, Glutamate) (54) | 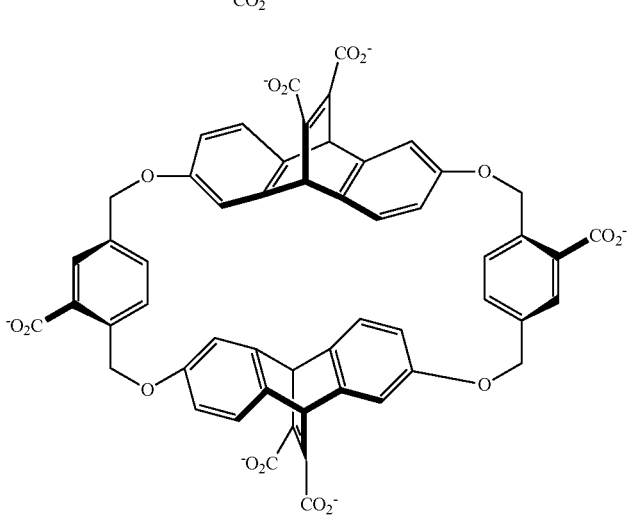 |

TABLE 2-continued
Illustrative guest amino acid(s) and their corresponding molecular tweezers.
References describing synthesis of tweezers are identified in brackets.
| Guest Amino Acid/ (Reference) | Molecular Tweezers |
|---|---|
| Arginine, Lysine, X-Arg dipeptides (Aspartate, Glutamate) (54) | 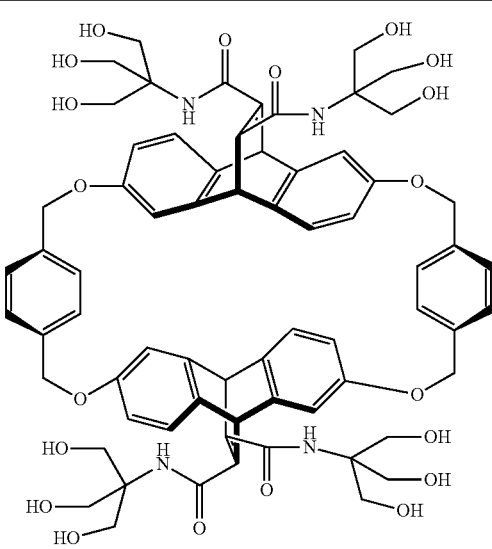 |
| Arginine, Lysine, X-Arg dipeptides (Aspartate, Glutamate) (54) | 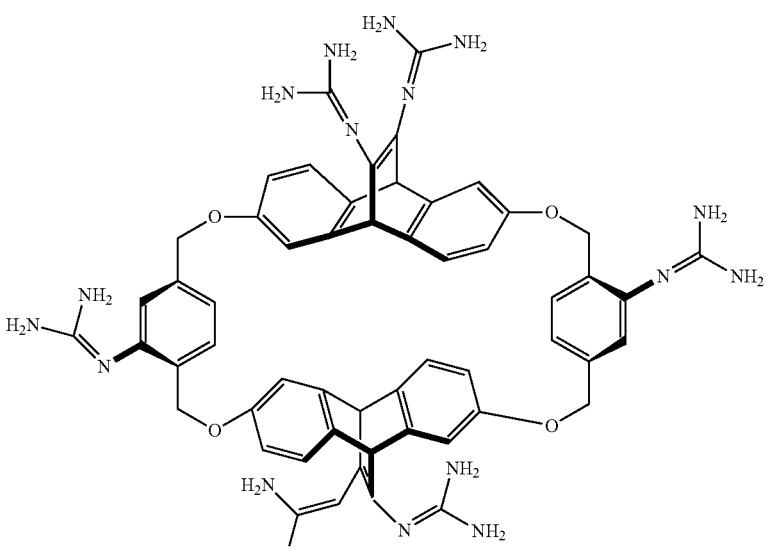 |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| Arginine, Lysine, X-Arg dipeptides (Aspartate, Glutamate) (54) | |
| Tyrosine (55) | |

TABLE 2-continued
Illustrative guest amino acid(s) and their corresponding molecular tweezers.
References describing synthesis of tweezers are identified in brackets.
| Guest Amino Acid/ (Reference) | Molecular Tweezers |
|---|---|
| Tyrosine (56) | 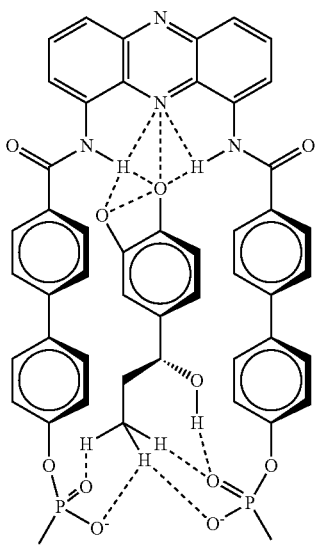 |
| Tyrosine (56) | 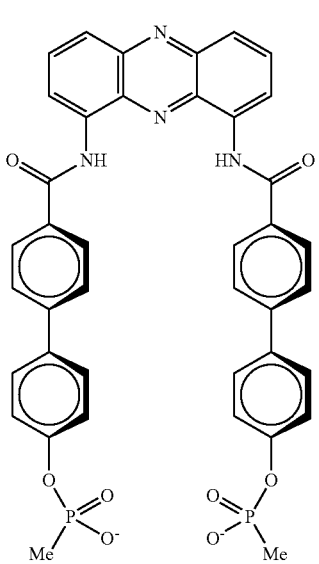 |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| Tyrosine (56) | *[structure]* |
| Tyrosine (56) | *[structure]* |
| Phenylalanine (57) | *[structure]* |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| Phenylalanine (57) | (structure: glycoluril-based tweezer with two dimethoxybenzene arms, OMe groups at 4 positions, Ph substituents) |
| Phenylalanine (57) | (structure: glycoluril-based tweezer with two dimethoxynaphthalene arms, OMe groups, Ph substituents) |
| Phenylalanine (57) | (structure: glycoluril core with four ClCH$_2$–N groups and two Ph substituents) |
| Phenylalanine (57) | (structure: glycoluril-based tweezer with two dihydroxynaphthalene arms, OH groups, Ph substituents) |
| Phenylalanine (57) | (structure: glycoluril-based tweezer with two diacetoxynaphthalene arms, OAc groups, Ph substituents) |
| Phenylalanine (57) | (structure: glycoluril-based tweezer with two dimethoxynaphthalene arms, OMe groups, Ph substituents) |

TABLE 2-continued
Illustrative guest amino acid(s) and their corresponding molecular tweezers.
References describing synthesis of tweezers are identified in brackets.
| Guest Amino Acid/ (Reference) | Molecular Tweezers |
|---|---|
| Phenylalanine (57) | 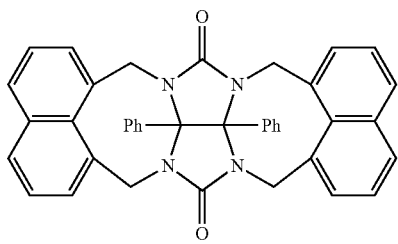 [SMILES: O=C1N2Cc3cccc4cccc(c34)CN3C(=O)N4Cc5cccc6cccc(c56)CN1C4(c1ccccc1)C23c1ccccc1] |
| Phenylalanine (58) | 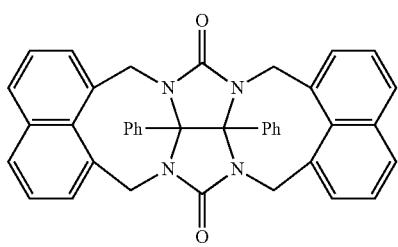 [SMILES: O=C1N2Cc3cccc4cccc(c34)CN3C(=O)N4Cc5cccc6cccc(c56)CN1C4(c1ccccc1)C23c1ccccc1] |
| Phenylalanine (58) | 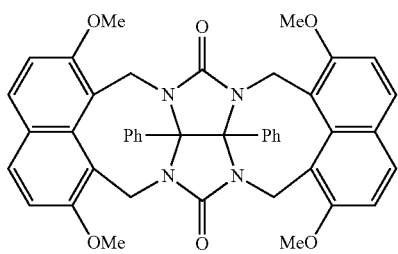 [SMILES: COc1ccc2ccc(OC)c3c2c1CN1C(=O)N2Cc4c(OC)ccc5ccc(OC)c(c45)CN4C(=O)N(C3)C1(c1ccccc1)C24c1ccccc1] |
| Phenylalanine (58) | 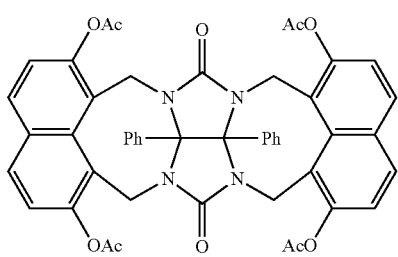 [SMILES: CC(=O)Oc1ccc2ccc(OC(C)=O)c3c2c1CN1C(=O)N2Cc4c(OC(C)=O)ccc5ccc(OC(C)=O)c(c45)CN4C(=O)N(C3)C1(c1ccccc1)C24c1ccccc1] |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
| --- | --- |
| Phenylalanine (58) | [chemical structure] |
| Phenylalanine, Tryptophan, Tyrosine (59) | 1-Acetyl-4,4-bis[4-(ethoxycarbonylmethoxy)-3,5-dimethylphenyl]piperidine<br><br>1-Acetyl-4,4-bis[4-(carboxymethoxy)-3,5-dimethylphenyl]piperidine<br>1-Acetyl-4,4-bis[4-(succinimidyloxycarbonylmethoxy)-3,5-dimethylphenyl]piperidine<br>1-Acetyl-4,4-bis[4-(carbamoylmethoxy)-3,5-dimethylphenyl]piperidine<br>1-Ethyl-4,4-bis[4-(2-aminoethoxy)-3,~dimethylphenyl]~p<br>1-Benzyloxycarbonyl-4,4-b is [4-(carboxymethoxy)-3,5 dimethylphenyl]piperidine<br>1 -Benzyloxycarbonyl-4,4-bis[4-(chloroformylmethoxy)-3,5-dimethylphenyl]piperidine<br>1-Acetyl-1'-ethyl-9,13,17,19,29,33,37,39-octamethyl-3,25-dioxodispiro[1,7,21,27-tetraoxa-4,24-diaza[7.1.7.1]paracyclophane-14,4':34,4"-bispiperidine]<br>l',1"'-Diethyl-9,13,17,19,29,33,37,39-oc~methyldispir~1,7,21,27-tetraoxa-4,24-diaza[7.1.7.1]paracyclophanel-4,4':34,4"-bispiperidine<br>1'-benzyloxy carbonyl-I",1"'-diethyl-6,12,22,28,37,43,48,51,52,55,-56,59-dodecamethyl-2,16-dioxotrispiro[4,14,20,30,35,45-hexaoxa-1,17-Diazaoctacyclo[15.15.15.2$^{5,8}$.2$^{10,13}$.2$^{21,24}$.2$^{26,29}$.2$^{36,39}$.2$^{41,44}$]nonapentaconta-5,7,10,12,21,23,26,28,36,38,41,43,48,50,52,54,56,58-octadecaene-9,4':25,4":40,4'''-trispiperidine]<br>1",1'''-Diethyl-6,12,22,28,37,43,48,51,52,55,56,59-dodecamethyl-2,16-dioxotrispiro[4,14,20,30,35,45-hexaoxa-1,17-diazaoctacyclo-[15.15.15.2$^{5,8}$.2$^{10,13}$.2$^{21,24}$.2$^{26,29}$.2$^{36,39}$.2$^{41,44}$]nonapentaconta-5,7,10,12,21,23,26,28,36,38,41,43,48,50,52,54,56,58-octadecaene-9,4':25,4":40,4'''-trispiperidine]<br>1 -Acetyl-1",1'''-diethyl-6,12,22,28,37,43,48,51,52,55,56,59-dodecamethyl-2,16-dioxotrispiro(4,14,20,30,35,45-hexaoxa-1,17-diazaoctacyclo[15.15.15.2$^{5,8}$.2$^{10,13}$.2$^{21,24}$.2$^{26,29}$.2$^{36,39}$.2$^{41,44}$]nonapentaconta-5,7,10,12,21,23,26,28,36,38,41,43,48,50,52,54,56,58-octadecaene-9,4':25,4":40,4'''-trispiperidine]<br>1',1",1'''-Triethyl-6,12,22,28,37,43,48,51,52,55,56,59-dodecamethyl-2,16-dioxotrispiro[4,14,20,30,35,45-hexaoxa- 1,17-diazaoctacyclo-[15.15.15.2$^{5,8}$.2$^{10,13}$.2$^{21,24}$.2$^{26,29}$.2$^{36,39}$.2$^{44,41}$]nonapentaconta-5,7,10,12,21,23,26,28,36,38,41,43,48,50,52,54,56,58-octadecaene- |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| | 9,4':25,4":40,4'''-trispiperidine]<br>1',1",1'''-Triethyl-6,12,22,28,37,43,48,51,52,55,56,59-dodecamethyltrispiro[4,14,20,30,35,45-hexaoxa-1,17-diazaoctacyclo-[15.15.15.2$^{5,8}$.2$^{10,13}$.2$^{21,24}$.2$^{26,29}$.2$^{36,39}$.2$^{41,44}$]nonapentaconta-5,7,10,12,21,23,26,28,36,38,41,43,48,50,52,54,56,58-octadecaene-9,4':25,4":40,4'''-trispiperidine] |
| Phenylalanine, Tryptophan, Tyrosine (60) | 5,10,15,20-tetrakis{5-p-[ö-methoxypoly(oxyethylene)]phenyl}porphyrin cobalt(II) |
| Phenylalanine, Tryptophan, Tyrosine (61) | 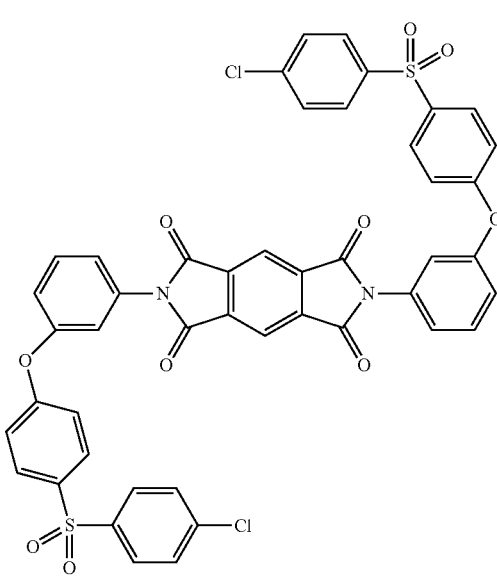 [SMILES: O=c1c2cc3c(=O)n(-c4cccc(Oc5ccc(S(=O)(=O)c6ccc(Cl)cc6)cc5)c4)c(=O)c3cc2c(=O)n1-c1cccc(Oc2ccc(S(=O)(=O)c3ccc(Cl)cc3)cc2)c1]<br>2,6-bis(3-(4-((4-chlorophenyl)sulfonyl)phenoxy)phenyl) pyrrolo[3,4-f]isoindole-1,3,5,7(2H,6H)-tetraone |
| Phenylalanine, Tryptophan, Tyrosine (61) | 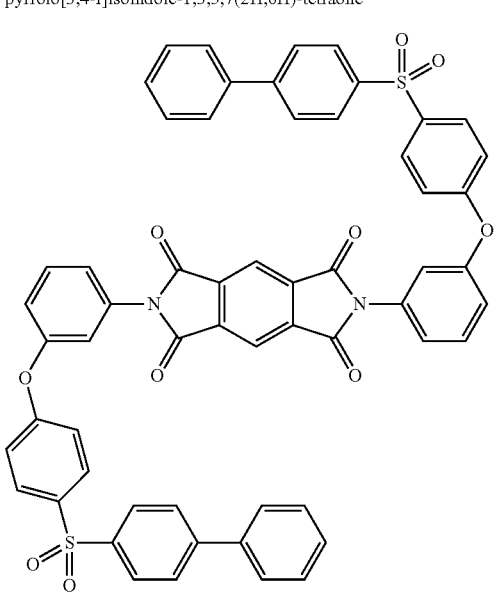<br>2,6-bis(3-(4-([1,1'-byphenyl]-4-ylsulfonyl)phenoxy)phenyl)[3,4-f]isoindole 1,3,5,7(2H,6H)-tetraone |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| Phenylalanine, Tryptophan, Tyrosine (61) | 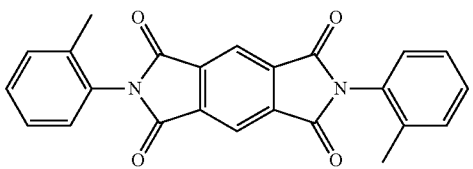 [SMILES: Cc1ccccc1-n1c(=O)c2cc3c(=O)n(-c4ccccc4C)c(=O)c3cc2c1=O]<br>2,6-di-o-tolylpyrrolo[3,4-f]isoindole-1,35,7(2H,6H)-tetraone |
| Phenylalanine, Tryptophan, Tyrosine (61) | 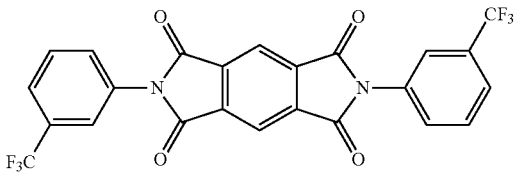<br>2,6-bis(3-(trifluoromethyl)methyl)phenyl)pyrrolo[3,4-f]isoindole-1,3,5,7(2H,6H)-tetraone |
| Phenylalanine, Tryptophan, Tyrosine (61) | 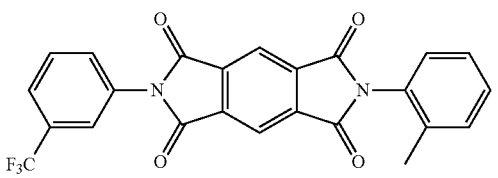 [SMILES: Cc1ccccc1-n1c(=O)c2cc3c(=O)n(-c4cccc(C(F)(F)F)c4)c(=O)c3cc2c1=O]<br>2-(o-tolyl)-6-(3-(trifluoromethyl)phenyl)pyrrolo[3,4-f]isoindole-1,3,5,7(2H,6H)-tetraone |
| Phenylalanine, Tryptophan, Tyrosine (61) | 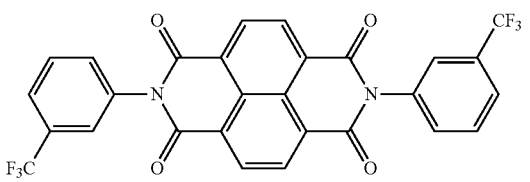 [SMILES: O=C1c2ccc3c4c(ccc(c24)C(=O)N1c1cccc(C(F)(F)F)c1)C(=O)N(c1cccc(C(F)(F)F)c1)C3=O]<br>2,7-bis(3-(trifluoromethyl)phenyl)benzo[imn][3,8]phenanthroline-1,3,6,8-(2H,7H)-tetraone |
| Glutamine, Asparagine (62) | 5-Bromo-25,26-27,28-bis(crown-3)-calix[4]arene<br>5-Cyano-25,26-27,28-bis(crown-3)-calix[4]arene<br>5-Aminomethyl-25,26-27,28-bis(crown-3)-calix[4]-Arene<br>5-(4-Methylbenzenesulfonamido)methyl-25,26-27,28-bis(crown-3)-calix[4]arene<br>5-Amino-25,26-27,28-bis(crown-3)-calix[4]arene<br>5-(N-Phenylureido)methyl-25,26-27,28-bis(crown-3)-calix[4]arene<br>5-(N-Phenyl(thio)ureido)methyl-25,26-27,28-bis(crown-3)-calix[4]arene<br>5-(N-Phenylureido)-25,26:27,28-bis(crown-3)-calix[4]-Arene<br>5-(N-Phenylureido)methyl-25,26-27,28-bis(crown-3)-calix[4]arene<br>N-benzyl-N-phenylurea 11<br>Phenylureidomethyl-tetrapropoxy-calix[4]arene 12 |
| Phenylalanine, Tryptophan (63) | 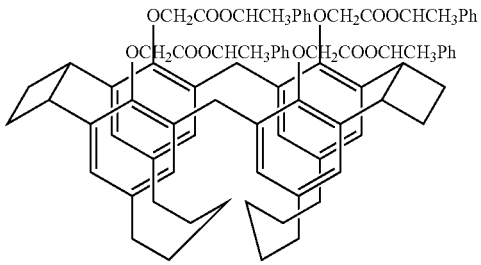 |

TABLE 2-continued
Illustrative guest amino acid(s) and their corresponding molecular tweezers.
References describing synthesis of tweezers are identified in brackets.
| Guest Amino Acid/ (Reference) | Molecular Tweezers |
|---|---|
| Phenylalanine, Tryptophan (63) | 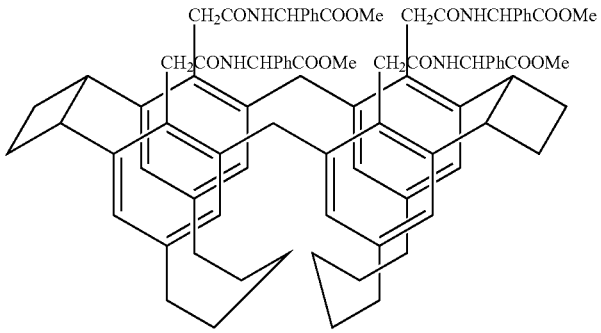 |
| Phenylalanine, Tryptophan (63) | 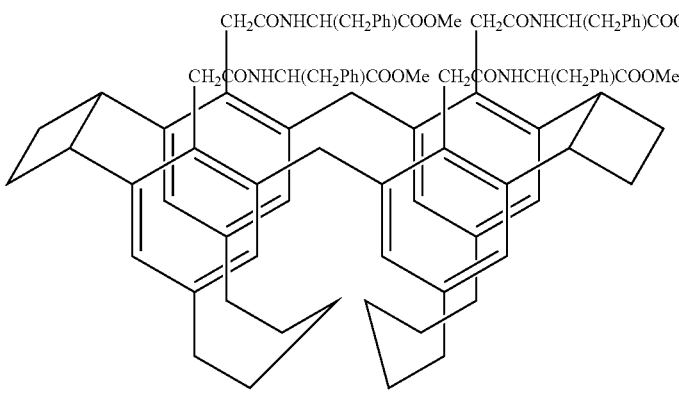 |
| Phenylalanine, Tryptophan (63) | 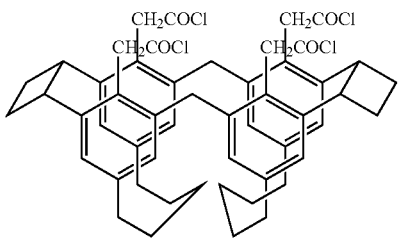 |
| Phenylalanine, Tryptophan (63) | 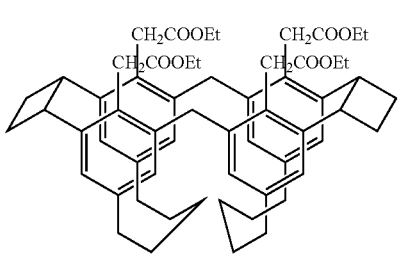 |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| Glutamate, Aspartate, Carboxylates, C-terminal Val, C-terminal Ala, C-terminal Phe (64) | |
| Glutamate, Aspartate, Carboxylates, C-terminal Val, C-terminal Ala, C-terminal Phe (64) | |
| Glutamate, Aspartate, Carboxylates, C-terminal Val, C-terminal Ala, C-terminal Phe: (64) | |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| Glutamate, Aspartate, Carboxylates, C-terminal Val, C-terminal Ala, C-terminal Phe (64) | 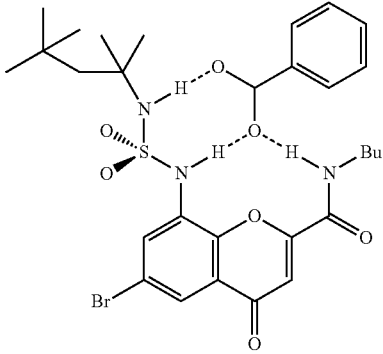 |
| Glutamate, Aspartate, Carboxylates, C-terminal Val, C-terminal Ala, C-terminal Phe (65) | 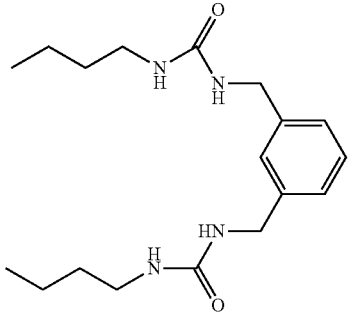 [SMILES: CCCCNC(=O)NCc1cccc(CNC(=O)NCCCC)c1]<br>1,1'-(1,3-phenylenebis(methylene))bis(3-butylurea) |
| Glutamate, Aspartate, Carboxylates, C-terminal Val, C-terminal Ala, C-terminal Phe (65) | 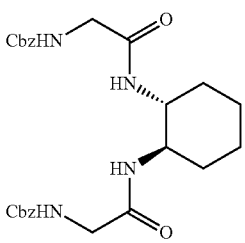 [SMILES: O=C(CNC(=O)OCc1ccccc1)N[C@@H]1CCCC[C@H]1NC(=O)CNC(=O)OCc1ccccc1]<br>dibenzyl (((1R,2R)-cyclohexane-1,2-diylbis (azanediyl))bis(2-oxoethane-2,1))dicarbamate |
| Glutamate, Aspartate, Carboxylates, C-terminal Val, C-terminal Ala, C-terminal Phe (65) | 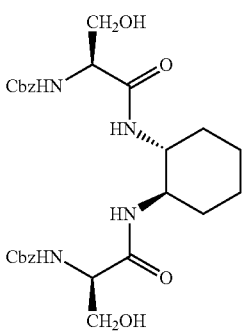 [SMILES: O=C(N[C@@H](CO)C(=O)N[C@@H]1CCCC[C@H]1NC(=O)[C@@H](CO)NC(=O)OCc1ccccc1)OCc1ccccc1]<br>dibenzyl ((2S,2'R)-((1R,2R)-cyclohexane-1-2 diylbis(azanediyl))bis(3-hydroxy-1-oxopropane-2,1-diyl))dicarbamate |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| Glutamate, Aspartate, Carboxylates, C-terminal Val, C-terminal Ala, C-terminal Phe (65) | 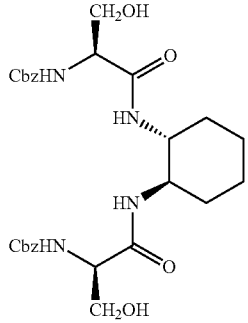 [SMILES: O=C(N[C@@H](CO)C(=O)N[C@@H]1CCCC[C@H]1NC(=O)[C@@H](CO)NC(=O)OCc1ccccc1)OCc1ccccc1]<br>dibenzyl ((2S,2'R)-((1R,2R)-cyclohexane-1,2-diylbis(azanediyl))bis(3-hydroxy-1-oxopropane-2,1-diyl))dicarbamate |
| Glutamate, Aspartate, Carboxylates, C-terminal Val, C-terminal Ala, C-terminal Phe (65) | 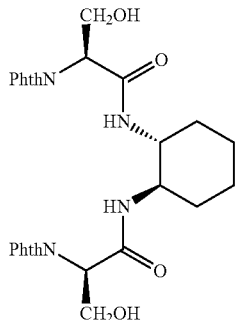 |
| Glutamate, Aspartate, Carboxylates, C-terminal Val, C-terminal Ala, C-terminal Phe (65) | 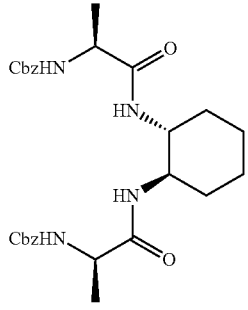 [SMILES: C[C@H](NC(=O)OCc1ccccc1)C(=O)N[C@@H]1CCCC[C@H]1NC(=O)[C@@H](C)NC(=O)OCc1ccccc1]<br>dibenzyl ((2S,2'R)-((1R,2R)-cyclohexane-1,2-diylbis(azanediyl))bis(1-oxopropane-2,1-diyl))dicarbamate |
| Glutamate, Aspartate, Carboxylates, C-terminal Val, C-terminal Ala, C-terminal Phe (66) | 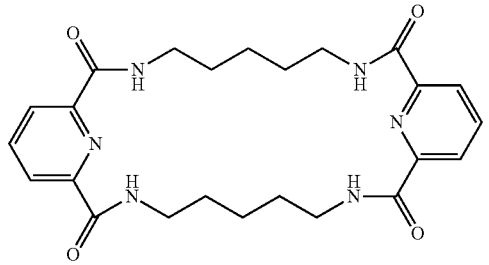 [SMILES: O=C1NCCCCCNC(=O)c2cccc(n2)C(=O)NCCCCCNC(=O)c2cccc1n2] |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
| --- | --- |
| Glutamate, Aspartate, Carboxylates, C-terminal Val, C-terminal Ala, C-terminal Phe (66) | 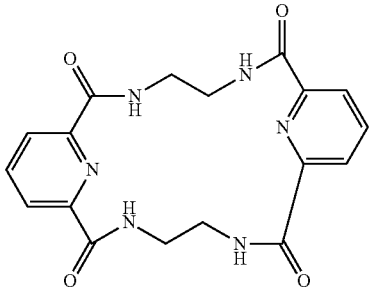 [SMILES: O=C1NCCNC(=O)c2cccc(n2)C(=O)NCCNC(=O)c2cccc1n2] |
| Glutamate, Aspartate, Carboxylates, C-terminal Val, C-terminal Ala, C-terminal Phe (66) | 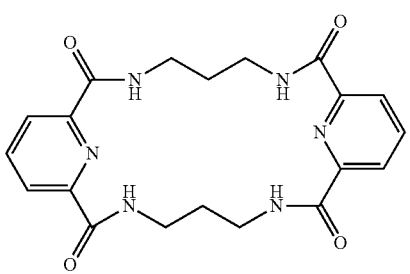 [SMILES: O=C1NCCCNC(=O)c2cccc(n2)C(=O)NCCCNC(=O)c2cccc1n2] |
| Glutamate, Aspartate, Carboxylates, C-terminal Val, C-terminal Ala, C-terminal Phe (66) | 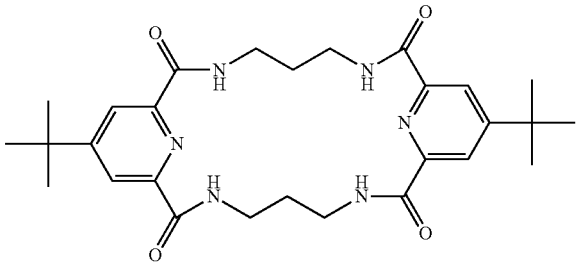 [SMILES: CC(C)(C)c1cc2nc(c1)C(=O)NCCCNC(=O)c1cc(C(C)(C)C)cc(n1)C(=O)NCCCNC2=O] |
| Glutamate, Aspartate, Carboxylates, C-terminal Val, C-terminal Ala, C-terminal Phe (67) | 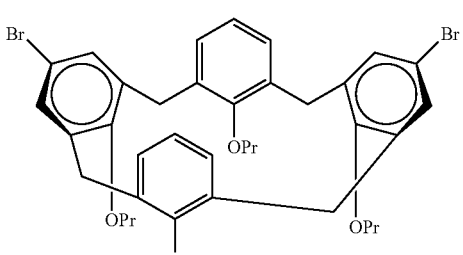 |
| Glutamate, Aspartate, Carboxylates, C-terminal Val, C-terminal Ala, C-terminal Phe (67) | 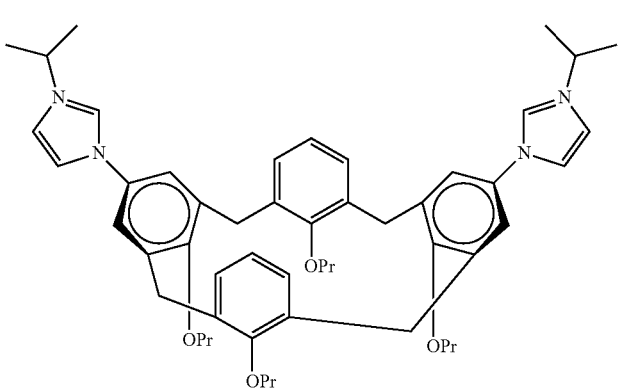 |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| Glutamate, Aspartate, Carboxylates, C-terminal Val, C-terminal Ala, C-terminal Phe (67) | |
| Glutamate, Aspartate, Carboxylates, C-terminal Val, C-terminal Ala, C-terminal Phe (67) | |
| Glutamate, Aspartate, Carboxylates, C-N terminal Val, C-terminal Ala, C-terminal Phe (67) | |
| Glutamate, Aspartate, Carboxylates, C-terminal Val, C-terminal Ala, C-terminal Phe (67) | |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| Glutamate, Aspartate, Carboxylates, C-terminal Val, C-terminal Ala, C-terminal Phe (67) | 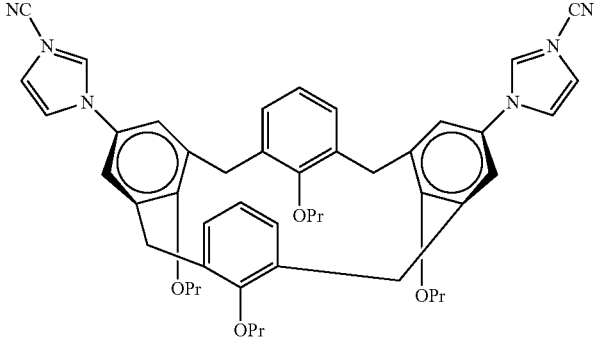 |
| Glutamate, Aspartate, Carboxylates, C-terminal Val, C-terminal Ala, C-terminal Phe (67) | 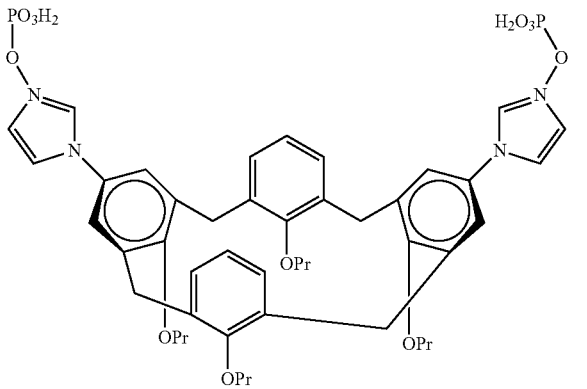 |
| Glutamate, Aspartate, Carboxylates, C-terminal Val, C-terminal Ala, C-terminal Phe (67) | 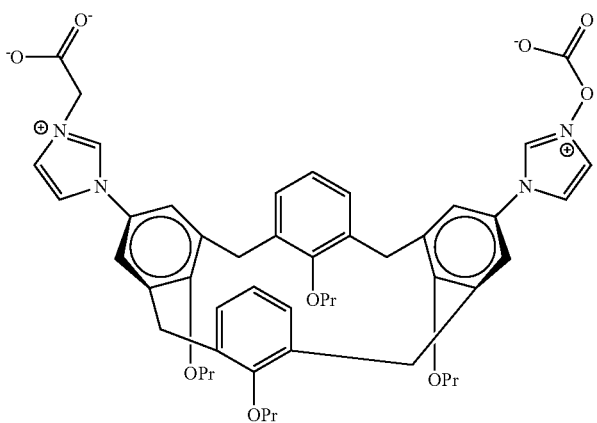 |
| Glutamate, Aspartate, Carboxylates, C-terminal Val, C-terminal Ala, C-terminal Phe (67) | 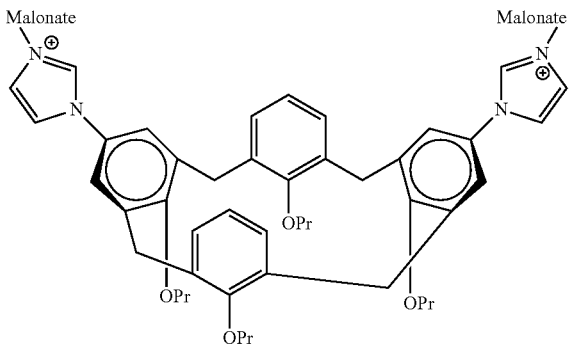 |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| Glutamate, Aspartate, Carboxylates, C-terminal Val, C-terminal Ala, C-terminal Phe (67) | 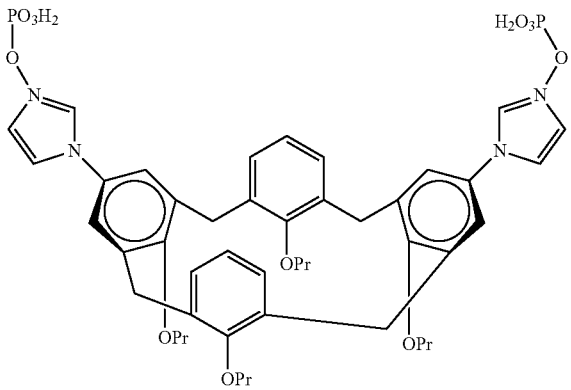 |
| Gly-Gly, Ala-Ala, Val-Ala, Val-Val (69) | 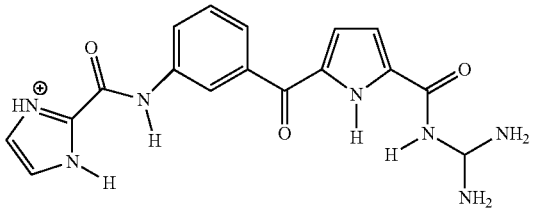 [SMILES: NC(N)NC(=O)c1ccc(C(=O)c2cccc(NC(=O)c3[nH]cc[nH+]3)c2)[nH]1] 2-((3-(5-diaminomethyl)carbamoyl)-1H-pyrrole-2-carbonyl)phenyl)carbamoyl)-1H-imidazol-3-ium 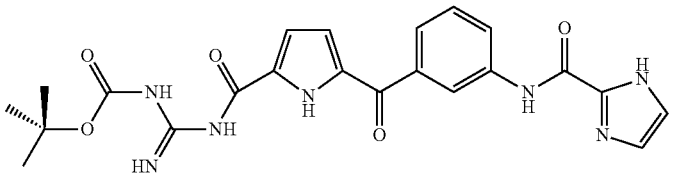 |
| Gly-Gly, Ala-Ala, Val-Ala, Val-Val (70) | 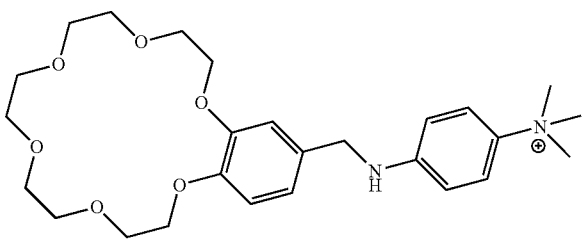 [SMILES: C[N+](C)(C)c1ccc(NCc2ccc3c(c2)OCCOCCOCCOCCOCCO3)cc1] 4-((2,3,5,6,8,9,11,12,14,15-decahydrobenzo[b][1,4,7,10,13,16]hexaoxacyclooctadencin-18-yl)methyl)amino)-N,N,N-trimethylbenzenaminium |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| | 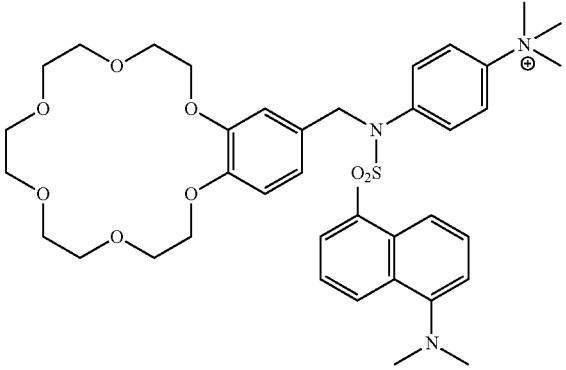 [SMILES: CN(C)c1cccc2c(S(=O)(=O)N(Cc3ccc4c(c3)OCCOCCOCCOCCOCCO4)c3ccc([N+](C)(C)C)cc3)cccc12]<br>4-(((2,3,5,6,8,9,11,12,14,15-decahydrobenzo[b][1,4,7,10,13,16]hexaoxacyclooctadecin-18-yl)methyl)(((5-(dimethylamino)naphthalen-1-yl)peroxy)thio)amino)-N,N,N-trimethylbenzenaminium |
| Glutamate, Aspartate, Carboxylates, C-terminal Val, C-terminal Ala, C-terminal Phe (68) | 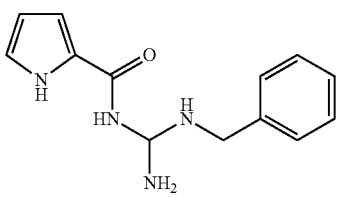 [SMILES: NC(NCc1ccccc1)NC(=O)c1ccc[nH]1]<br>N-(amino(benzylamino)methyl)-1H-pyrrole-2-carboxamide |
| Glutamate, Aspartate, Carboxylates, C-terminal Val, C-terminal Ala, C-terminal Phe (68) | 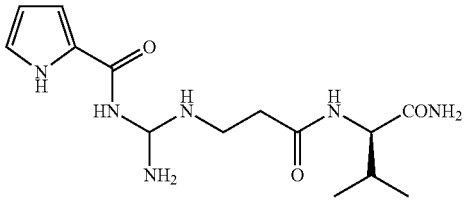 [SMILES: CC(C)[C@@H](NC(=O)CCNC(N)NC(=O)c1ccc[nH]1)C(N)=O]<br>N-(amino((3-(((R)-1-amino-3-methyl-1-oxobutan-2-yl)amino)-3-oxopropyl)amino)methyl)-1H-pyrrole-2-carboxamide |
| Glutamate, Aspartate, Carboxylates, C-terminal Val, C-terminal Ala, C-terminal Phe (68) | 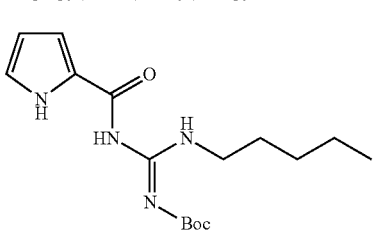 [SMILES: CCCCCN/C(=N\C(=O)OC(C)(C)C)NC(=O)c1ccc[nH]1] |
| Glutamate, Aspartate, Carboxylates, C-terminal Val, C-terminal Ala, C-terminal Phe (68) | 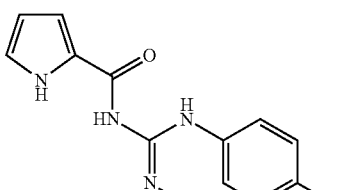 |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| Glutamate, Aspartate, Carboxylates, C-terminal Val, C-terminal Ala, C-terminal Phe (68) | 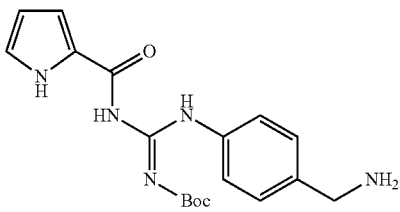 [SMILES: CC(C)(C)OC(=O)/N=C(/NC(=O)c1ccc[nH]1)Nc1ccc(CN)cc1] |
| Glutamate, Aspartate, Carboxylates, C-terminal Val, C-terminal Ala, C-terminal Phe (68) | 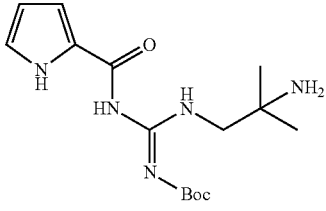 [SMILES: CC(C)(N)CN/C(=N\C(=O)OC(C)(C)C)NC(=O)c1ccc[nH]1] |
| Glutamate, Aspartate, Carboxylates, C-terminal Val, C-terminal Ala, C-terminal Phe (68) | 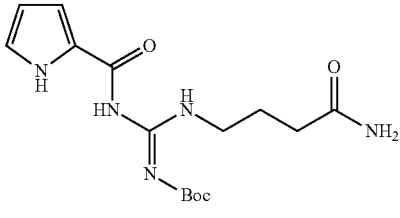 [SMILES: CC(C)(C)OC(=O)/N=C(\NCCCC(N)=O)NC(=O)c1ccc[nH]1] |
| Glutamate, Aspartate, Carboxylates, C-terminal Val, C-terminal Ala, C-terminal Phe N (68) | 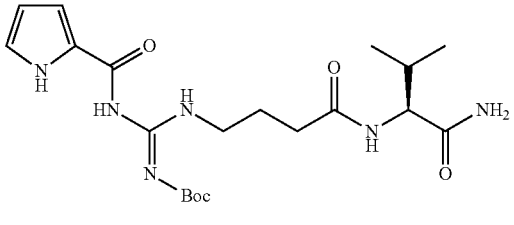 [SMILES: CC(C)[C@H](NC(=O)CCCN/C(=N\C(=O)OC(C)(C)C)NC(=O)c1ccc[nH]1)C(N)=O] |
| Arg-Gly-Asp (71) | 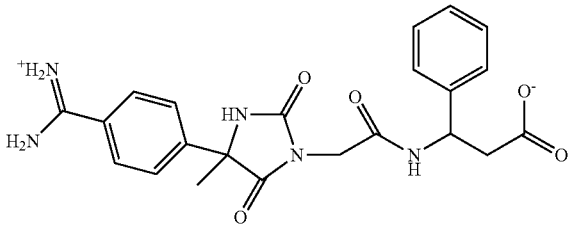 [SMILES: CC1(c2ccc(C(N)=[NH2+])cc2)NC(=O)N(CC(=O)NC(CC(=O)[O-])c2ccccc2)C1=O]<br>3-(2-(4-(4-(amino(iminio)methyl)phenyl)-4-methyl-2,5-dioxoimidazolidin-1-yl)acetamido)-3-phenylpropanoate<br>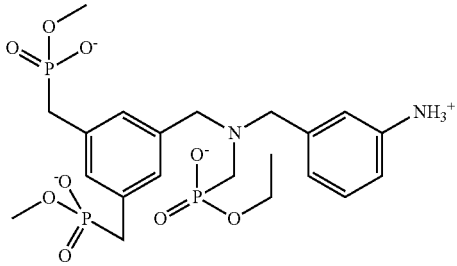<br>ethyl(((3-ammoniobenzyl)(3,5-bis((methoxyoxidophosphoryl)methyl)benzyl)amino)methyl)phosphonate |

… TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| Glu-Ser-Val, carboxy terminus, Glu, Asp (72) | 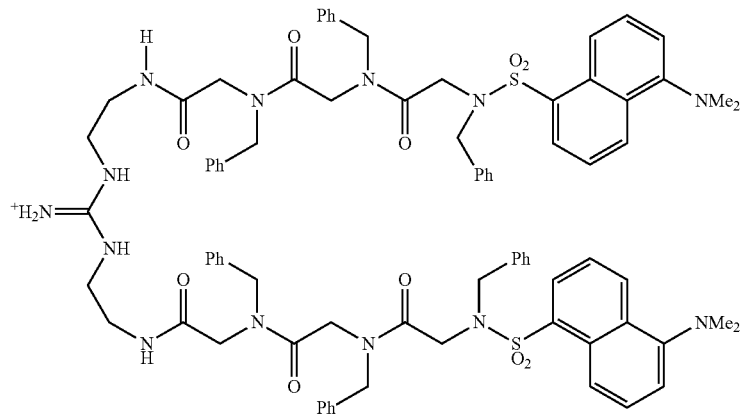 [SMILES: CN(C)c1cccc2c(S(=O)(=O)N(CC(=O)N(CC(=O)N(CC(=O)NCCNC(=[NH2+])NCCNC(=O)CN(Cc3ccccc3)C(=O)CN(Cc3ccccc3)C(=O)CN(Cc3ccccc3)S(=O)(=O)c3cccc4c(N(C)C)cccc34)Cc3ccccc3)Cc3ccccc3)Cc3ccccc3)cccc12]<br>5,8,22,25-tetrabenzyl-2,28-bis((5-dimethylamino)naphthalen-1-yl)sulfonyl)-4,7,10,20,23,26-hexaoxo-1,29-diphenyl-2,5,8,11,-14,16,19,22,25,28-decaazanonacosan-15-iminium |
| Glu-Ser-Val, carboxy terminus, Glu, Asp (72) | 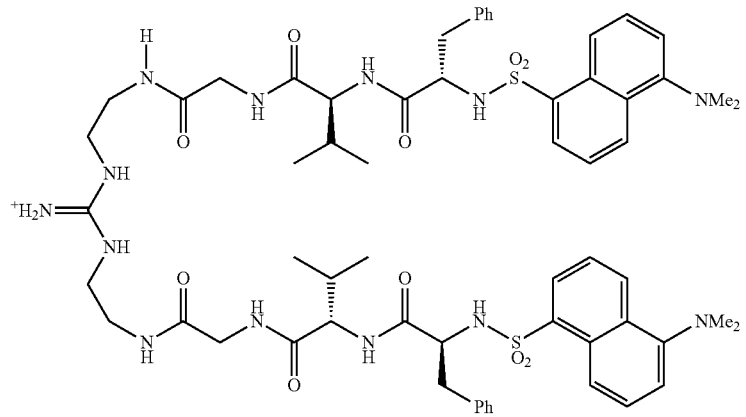 [SMILES: CC(C)[C@H](NC(=O)[C@H](Cc1ccccc1)NS(=O)(=O)c1cccc2c(N(C)C)cccc12)C(=O)NCC(=O)NCCNC(=[NH2+])NCCNC(=O)CNC(=O)[C@@H](NC(=O)[C@H](Cc1ccccc1)NS(=O)(=O)c1cccc2c(N(C)C)cccc12)C(C)C]<br>(2S,5S,23S,26S)-2,26-bis(5-dimethylamino)naphthalene-1-sulfonamido)-5,23-diisopropyl-3,6,9,19,22,25-hexaoxo-1,27-diphenyl-4,7,10,13,15,18,21,24-octaazaheptacosan-14-iminium |
| Glu-Ser-Val, carboxy terminus, Glu, Asp (72) | 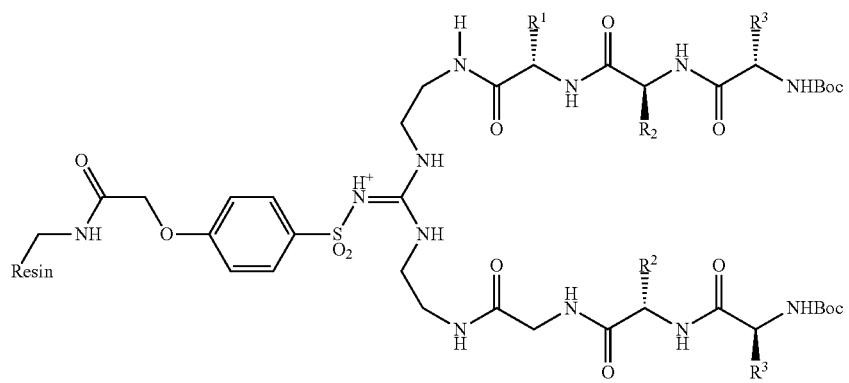 |

TABLE 2-continued
Illustrative guest amino acid(s) and their corresponding molecular tweezers.
References describing synthesis of tweezers are identified in brackets.
| Guest Amino Acid/ (Reference) | Molecular Tweezers |
|---|---|
| Glu-Ser-Val, carboxy terminus, Glu, Asp (72) | 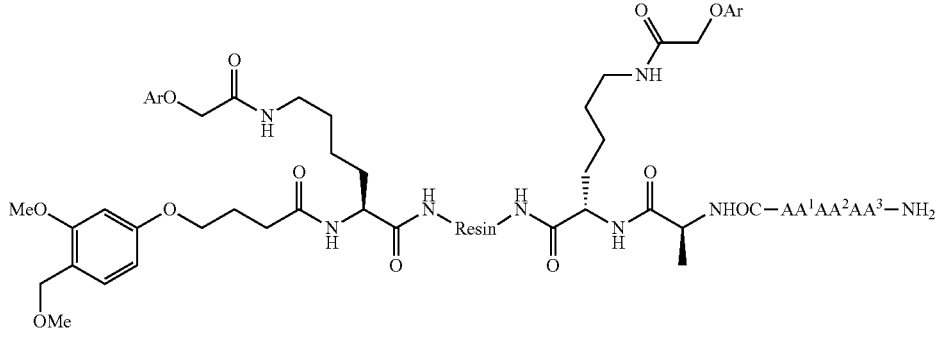 |
| C-terminal Ala-Gly-Ala (73) | 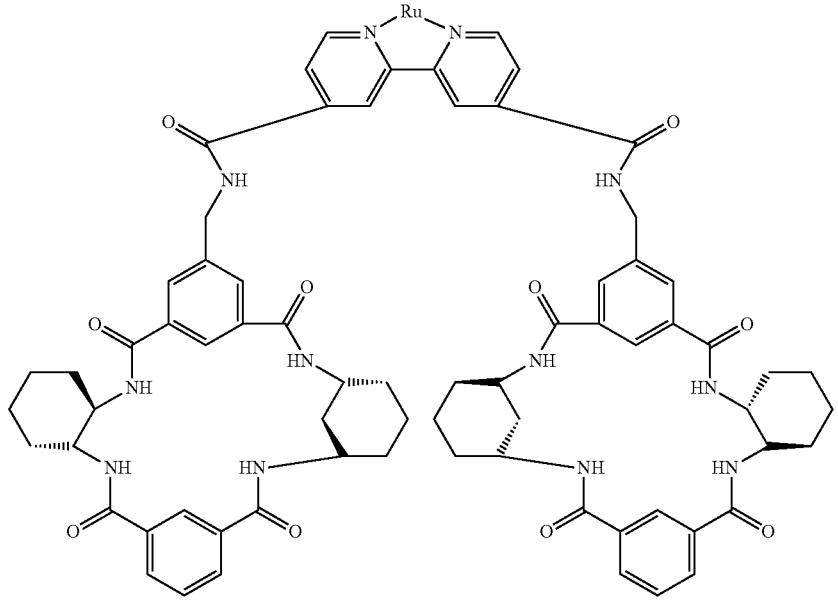 |

TABLE 2-continued
Illustrative guest amino acid(s) and their corresponding molecular tweezers.
References describing synthesis of tweezers are identified in brackets.
| Guest Amino Acid/ (Reference) | Molecular Tweezers |
|---|---|
| C-terminal Ala-Gly-Ala (73) | 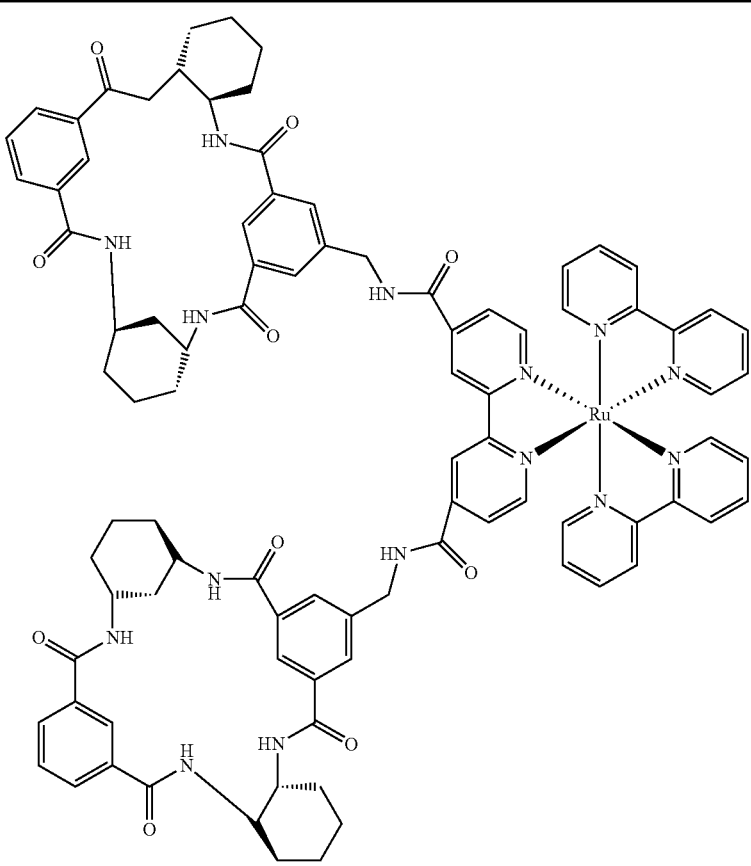 |
| His/Cys/Met-Lys-Lys (74) | 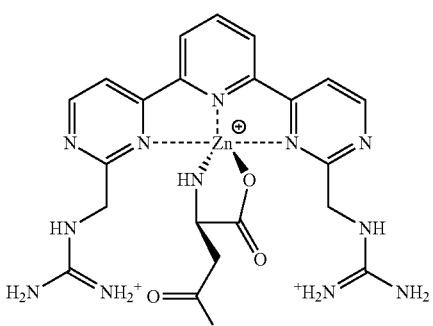 |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| His/Cys/Met-Lys-Lys (74) | 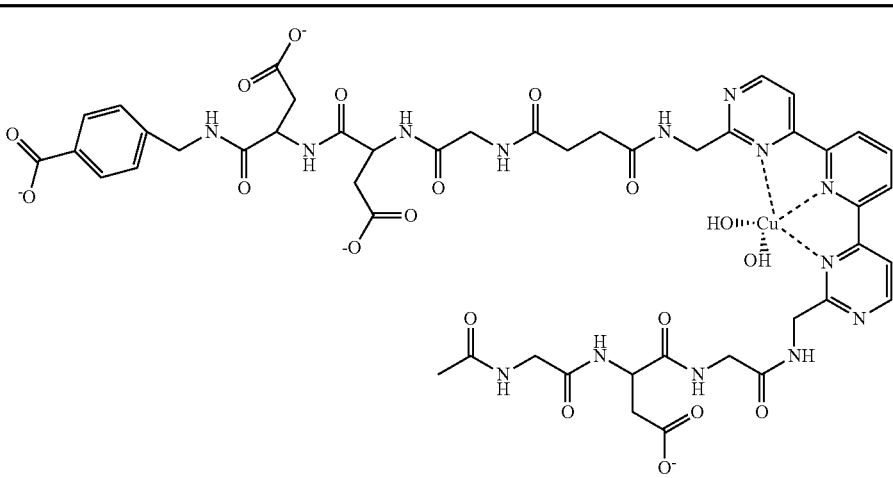 |
| Ala-Gln-Ala (76) | 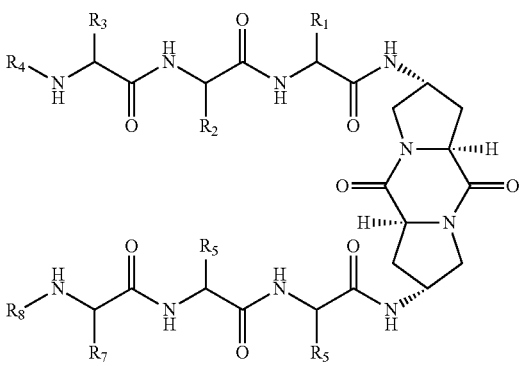 |
| Glu, Asp, C terminus (76) | 1,1'-Bis(isothiocyanato)ferrocene 2<br>1,1'-Bis(thioureido)ferrocenophanes<br>1,1'-bis(N-triphenylphosphoranylidenamino)ferrocene |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| Glu, Asp, C terminus (77) | 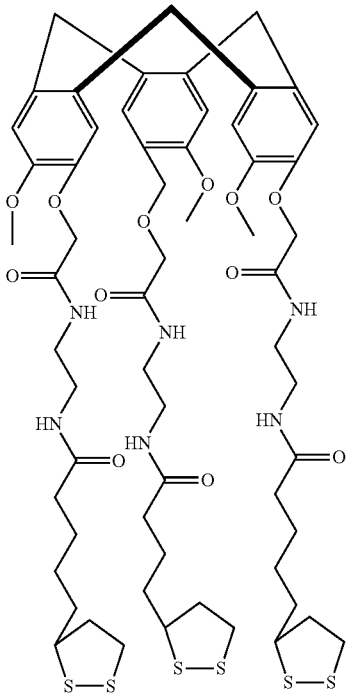<br>N,N'-(((2,2'-((12-((2-((2-(4-(1,2-dithiolan-3yl)butanamido)ethyl)amino)-2-oxoethoxy)methyl)-3,8-13-trimethoxy-10,15-dihydro-5H-tribenzo[a,d,g][9]annulene-2,7-diyl)(oxy))bis(acetyl))bis(azanedril))bis(ethane-2,1-diyl))bis(5-(1,2-dithiolan-3yl)pentanamide) |
| Val, Leu, Ile, Met (78) | 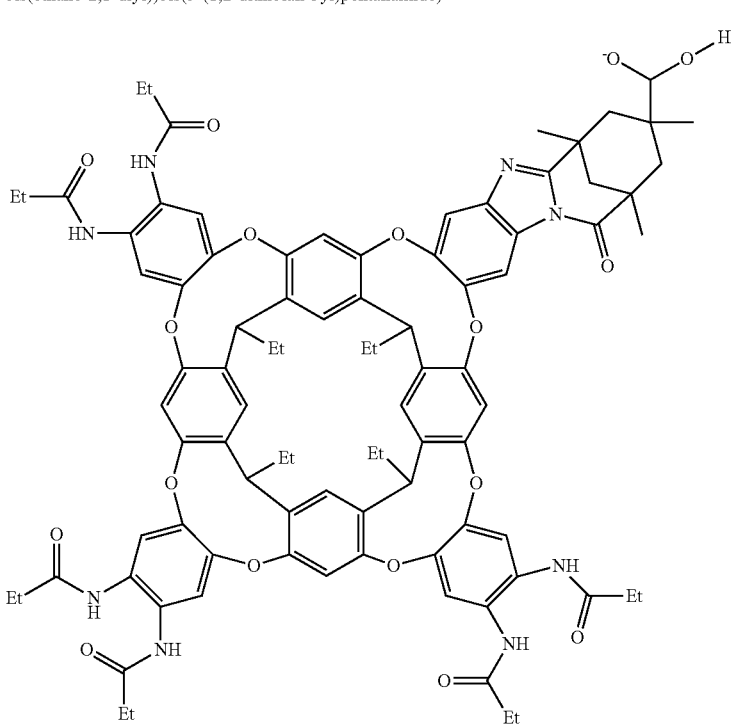 |

TABLE 2-continued
Illustrative guest amino acid(s) and their corresponding molecular tweezers.
References describing synthesis of tweezers are identified in brackets.
| Guest Amino Acid/ (Reference) | Molecular Tweezers |
|---|---|
| Val, Leu, Ile, Met (78) | 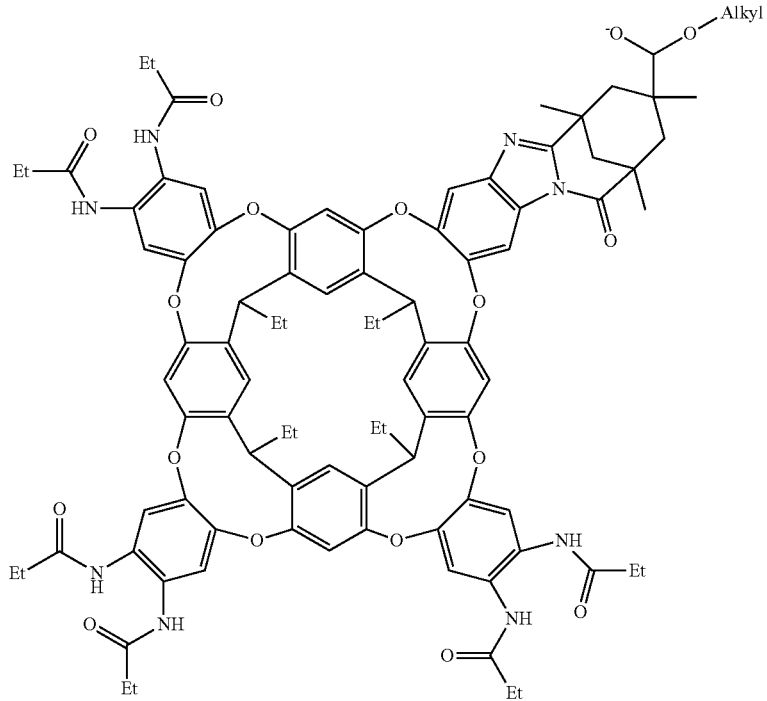 |
| Val, Leu, Ile, Met (78) | 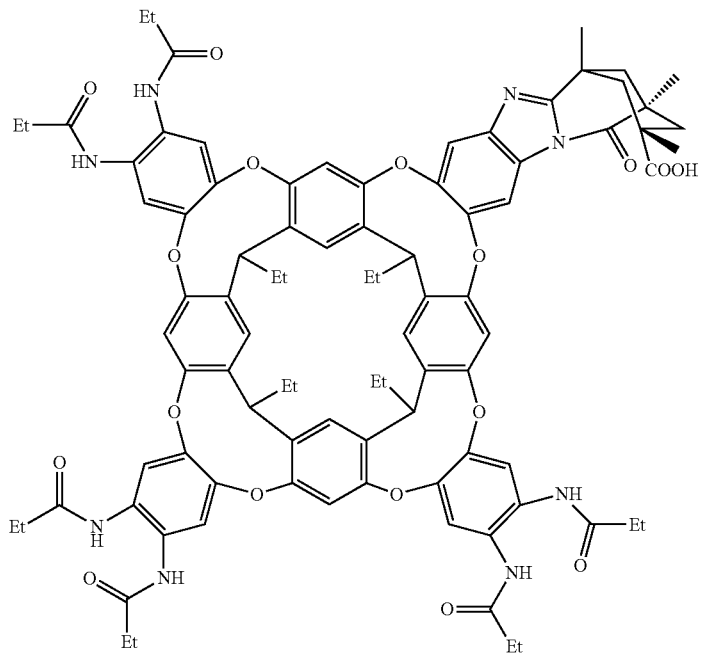 [SMILES: CCC(=O)Nc1cc2c(cc1NC(=O)CC)Oc1cc3c4cc1C(CC)c1cc5c(cc1O2)Oc1cc(NC(=O)CC)c(NC(=O)CC)cc1Oc1cc2c(cc1C5CC)C(CC)c1cc(c(cc1Oc1cc5c(cc1O2)nc1n5C(=O)[C@@]2(C)CC1(C)C[C@@](C)(C(=O)O)C2)Oc1cc(NC(=O)CC)c(NC(=O)CC)cc1O3)C4CC] |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| Val, Leu, Ile, Met (78) | [structure] |
| N-terminal Lysine (79) | [structure] dimethyl 10-(2-(10-(2-(tert-butoxycarbonyl)amino)ethyl)-21,23-dioxo-2,3,5,6,9,10,11,12,14,15,17,18-docecahydro-[1,4,7,10,13,16,19]hexaoxaazacyclohenicosino[8,9-f]isoindol-22(8H,21H,23H)-yl)ethyl-3,5,6,8,9,10,11,12,14,15,17,18-dodecahydro-2H-benzo[h][1,4,7,10,13,16,19]hexaoxaazacyclohenicosine-21,22-dicarboxylate |
| His, Thr, Gln (80) | [structure] Amino Acid Complex |
| Lys, Lys-Lys (81) | A-cyclodextrin Cucurbit[5]uril Cucurbit[6]iro; |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| Lys(Me$_3$) These references use acetylcholine as the guest molecule. They are included because acetylcholine resembles trimethyllysine (82) | 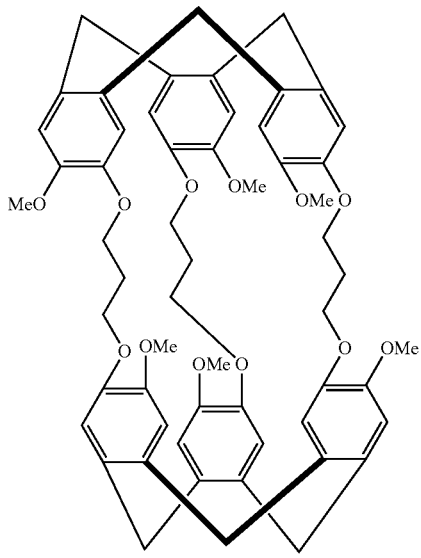 |
| Lys(Me$_3$) These references use acetylcholine as the guest molecule. They are included because resembles trimethyllysine (82) | 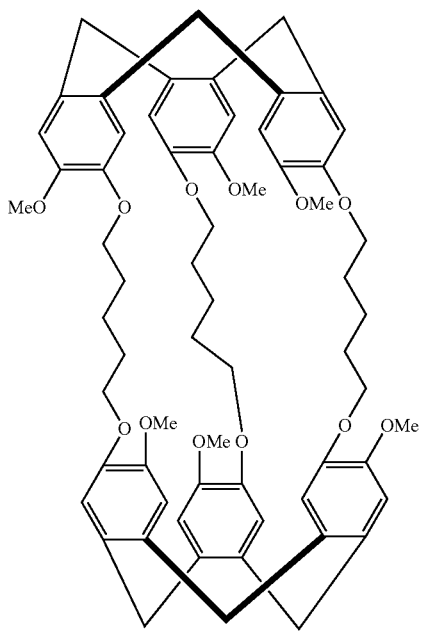 |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| Lys(Me$_3$) These references use acetylcholine as the guest molecule. They are included because acetylcholine resembles trimethyllysine (82) | 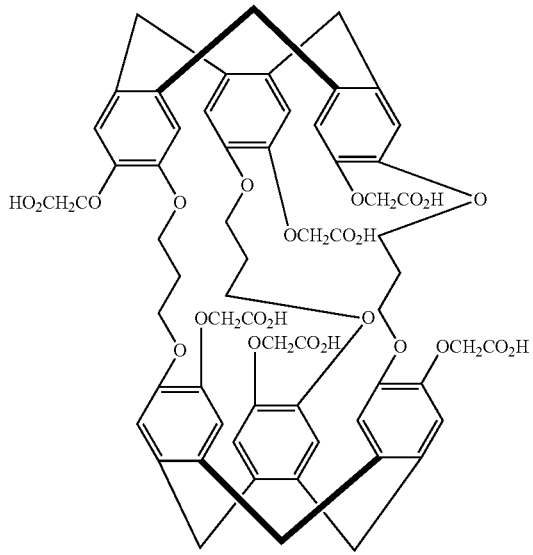 |
| Lys(Me$_3$) These references use acetylcholine as the guest molecule. They are included because acetylcholine resembles trimethyllysine (82) | 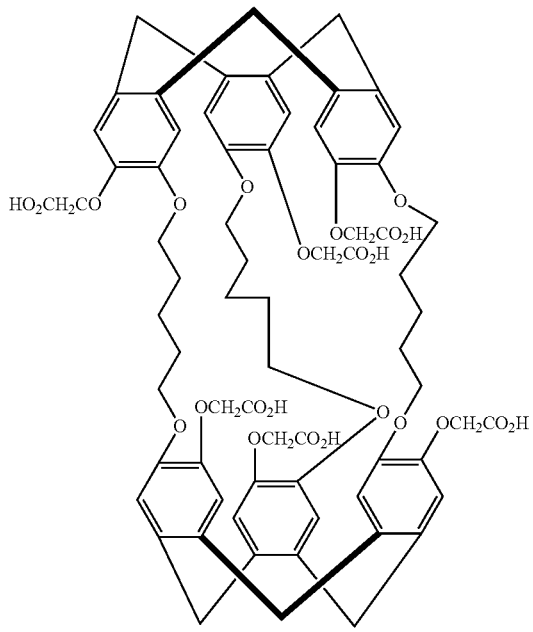 |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
|---|---|
| Lys(Me$_3$) These references use acetylcholine as the guest molecule. They are included because acetylcholine resembles trimethyllysine. (83) | 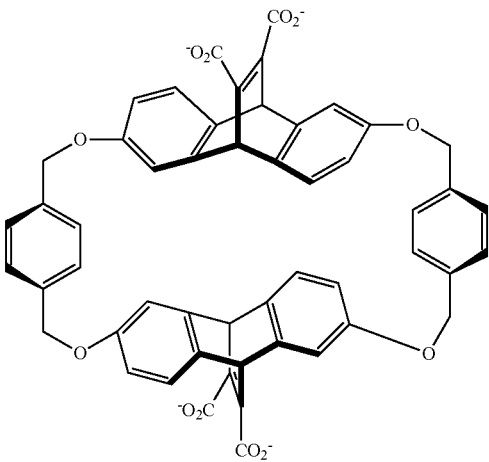 |
| Lys(Me$_3$) These references use acetylcholine as the guest molecule. They are included because acetylcholine resembles trimethyllysine. (83) | 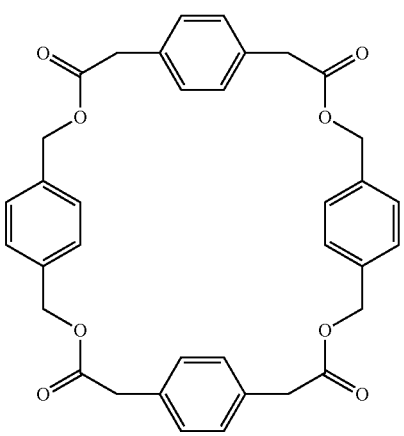 [SMILES: O=C1Cc2ccc(cc2)CC(=O)OCc2ccc(cc2)COC(=O)Cc2ccc(cc2)CC(=O)OCc2ccc(cc2)CO1] |
| Met (guest = dimethyl sulfide) (84) | 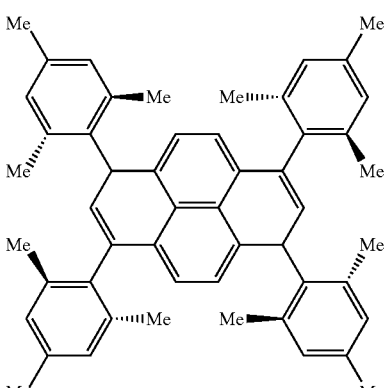 |

TABLE 2-continued

Illustrative guest amino acid(s) and their corresponding molecular tweezers.
References describing synthesis of tweezers are identified in brackets.

| Guest Amino Acid/ (Reference) | Molecular Tweezers |
| --- | --- |
| | 1,3,6,8-tetramesityl-1,6-dihydropyrene |
| Met (guest = dimethyl sulfide) (84) | 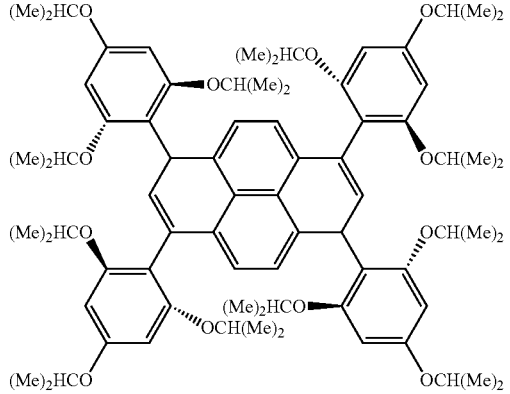 |
| | 1,3,6,8-tetrakis(2,4,6-triisopropoxyphenyl)1,6-dihydropyrene |
| Met (guest = dimethyl sulfide) (84) | 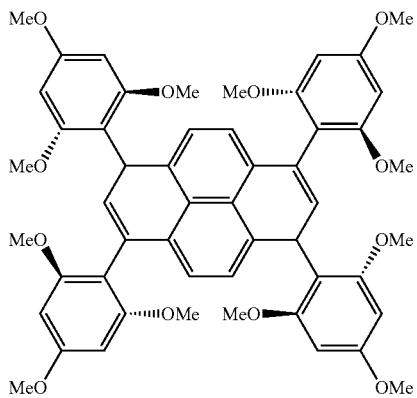 |
| | 1,3,6,8-tetrakis(2,4,6-trimethoxyphenyl)-1,6-dihydropyrene |
| Met (guest = dimethyl sulfide) (84) | 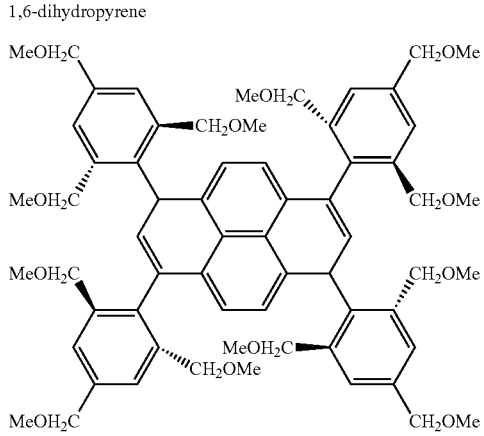 |
| | 1,3,6,8-tetrakis(2,4,6-tris(methoxymethyl)phenyl)-1,6-dihydropyrene |

References cited above (Table 2)

50. Talbiersky P, et al. "Molecular clip and tweezer introduce new mechanisms of enzyme inhibition." *J Am Chem Soc.* 2008 Jul 30;130(30):9824-8.

51. Mäkinen M, Karjalainen A and Vainiotalo P. "The complexation of two different ammonium ions with resorcarenes in protic solvent medium investigated by electrospray ionisation Fourier transform ion cyclotron resonance mass spectrometry." *Rapid Commun Mass* Sp. 2006 Jun 6;20(13):2009-2012.

TABLE 2-continued

Illustrative guest amino acid(s) and their corresponding molecular tweezers.
References describing synthesis of tweezers are identified in brackets.

Guest Amino
Acid/
(Reference)　　Molecular Tweezers

52. Huang WH, Zavalij PY and Isaacs L. "Folding of Long Chain Alkanediammonium Ions Promoted by a Cucurbituril Derivative." Org. Lett. 2008;10(12):2577-2580.
53. Rensing S, et al. "Optimization of a Synthetic Arginine Receptor. Systematic Tuning of Noncovalent Interactions." J Org Chem. 2001;66(17):5814-5821.
54. Ngola S, et al. "A Selective Receptor for Arginine Derivatives in Aqueous Media. Energetic Consequences of Salt Bridges That Are Highly Exposed to Water." J Am Chem Soc. 1999;121(6):1192-1201
55. N, et al. "Sensor for Nitrophenol Based on a Fluorescent Molecular Clip." Organic Letters. 2009;11(12):2603-2606.
56. Molt 0, Riibeling D and Schrader T. "A Selective Biomimetic Tweezer for Noradrenaline." J Am Chem Soc. 2003;125(40):12086-12087.
57. Sijbesma R, et al. "A molecular clip that binds aromatic guests by an induced-fit mechanism." J Am Chem Soc. 1992;114(25):9807-9813.
58. Sijbesma R, et al. "A molecular clip with allosteric binding properties." J Am Chem Soc. 1991;113(17):6695-6696.
59. Diederich F, et al. "Complexation of Arenes by Macrocyclic Hosts in Aqueous and Organic Solutions." J Am Chem Soc. 1986;108(9):2273-86.
60. Angelini N, et al. "Uncharged Water-Soluble Co(II)-Porphyrin: A Receptor for Aromatic a-Amino Acids." J Phys Chem B. 2005;109(39):18645-18651.
61. Colquhoun H, et al. "Sterically Controlled Recognition of Macromolecular Sequence Information by Molecular Tweezers." J Am Chem Soc. 2007 Nov 30;129(51):16163- 16174.
62. Arduini A, Secchi A and Pochini A. "Recognition of Amides by New Rigid Calix[4]arene-based Cavitands." J Org Chem. 2000;65(26):9085-9091.
63. Okada Y, et al. "The Selective Extraction and Transport of Amino Acids by Calix[4]arene-derived Esters." Tetrahedron Letters. 1995;36(4):555-558.
64. Raposo C, et al. "Readily Available Chromenone Receptors for Carboxylates." Tetrahedron Letters. 1994;35(20):3409-10.
65. Albert J and Hamilton A. "Synthetic analogs of the ristocetin binding site: neutral, multidentate receptors for carboxylate recognition." Tetrahedron Letters. 1993;34(46):7363-6.
66. Chmielewskia M, Szumnaa A and Jurczak J. "Anion induced conformational switch of a macrocyclic amide receptor." Tetrahedron Letters. 2004 Nov 15; 45(47): 8699-8703.
67. Dinares I, et al. "Bis(imidazolium)-Calix[4]arene Receptors for Anion Binding." J Org Chem. 2009;74(1):482-485.
68. Schmuck C and Bickert V. "N'-1-Alkylated Guanidiniocarbonyl Pyrroles: New Receptors for Amino Acid Recognition in Water." Org. Lett., 2003;5(24):4579-4581.
69. Schmuck C and Geiger L. "Dipeptide Binding in Water by a de Novo designed Guanidiniocarbonylpyrrole Receptor." J Am Chem Soc. 2004;126(29):8898-8899.
70. Hossain M and Schneider J. "Sequence-Selective Evaluation of Peptide Side-Chain Interaction. New Artificial Receptors for Selective Recognition in Water." J Am Chem Soc. 1998;120:11208-11209.
71. Rensing S, Schrader T. "The First Synthetic Receptor for the RGD Sequence." Org. Lett. 2002;4:2161-2164.
72. Davies M, et al. "Screening an Inverted Peptide Library in Water with a Guanidinium-Based Tweezer Receptor." J Org Chem. 1998;63:8696-8703.
73. Chang KH, et al. "Stereoselective Recognition of Tripeptides Guided by Encoded Library Screening: Construction of Chiral Macrocyclic Tetraamide Ruthenium Receptor for Peptide Sensing." J Org Chem. 2005;70(6):2026-2032.
74. Wright A and Anslyn E. "Cooperative Metal-Coordination and Ion Pairing in Tripeptide Recognition." Org Lett. 2004;6(9):1341-1344.
75. Bernard J and Wennemers H. "Macrocyclic Diketopiperazine Receptors: Effect of Macrocyclization on the Binding Properties of Two-Armed Receptors." Org Lett. 2007;9(21):4283-4286.
76. Oton C, et al. "Mononuclear Ferrocenophane Structural Motifs with Two Thiourea Arms Acting as a Dual Binding Site for Anions and Cations." Inorg Chem. 2009;48(4):1566-1576.
77. Zhang S and Echegoyen L. "Selective Anion Sensing by a Tris-Amide CTV Derivative: $^1$H NMR Titration, Self-Assembled Monolayers, and Impedance Spectroscopy." J. Am. Chem. Soc. 2005;127(6):2006-2011.
78. Purse B and Rebek J. "Self-fulfilling cavitands: Packing alkyl chains into small spaces." Proc Nat Acad Sci USA. 2006 Feb 21;103(8):2530-2534.
79. Mandl C and Konig B. "Luminescent Crown Ether Amino Acids: Selective Binding to N-terminal Lysine in Peptides." J Org Chem. 2005;70(2):670-674.
80. Terekhova I and Kulikov O. "Thermodynamic parameters of the interaction of cryptand[222] with amino acids in water at 298.15 K." Russian Chemical Bulletin. 1999;48(12):2259-2262.
81. Zhang H, Grabenauer M, Bowers M and Dearden DV. "Supramolecular Modification of Ion Chemistry: Modulation of Peptide Charge State and Dissociation Behavior through Complexation with Cucurbit[n]uril (n = 5, 6) or a-Cyclodextrin." J. Phys. Chem. A. 2009;113(8):1508-1517
82. Garel L, Lozach B, Dutasta JP and Collet A. "Remarkable effect of the receptor size in the binding of acetylcholine and related ammonium ions to water-soluble cryptophanes." J Am Chem Soc. 1993;115(24):11652-11653.
83. Barton S and Roelens S. "Binding of acetylcholine and tetramethylammonium to a cyclophane receptor: anion's contribution to the cation-pi interaction." J Am Chem Soc. 2002 Jul 17;124(28):8307-15.
84. Moorthy JN, Natarajan P and Venugopalan P. "Abundant Lattice Inclusion Phenomenon with Sterically Hindered and Inherently Shape-Selective Tetraarylpyrenes." J Org Chem. 2009 Oct 16;74(22):8566-8577.

Preparation of Molecular Tweezers.

The molecular tweezers can be synthesized according to any of a number of methods known to those of skill in the art. In this regard, methods of synthesizing molecular tweezers are known to those of skill in the art (see, e.g., Zimmerman et al. (1991) J. Am. Chem. Soc. 113: 183-196). More particularly, the synthesis of TW-2 is described by Fokkens et al. (2005) J. Am. Chem. Soc., 27 (41), pp 14415-14421) while the synthesis of various other molecular tweezers (including truncation variants) is described in Klärner et al. (2006) J. Am. Chem. Soc., 128(14): 4831-4841. The methods described therein can readily be modified to synthesize the other molecular tweezers described herein.

In addition, the synthesis of molecular tweezers TW1, TW2, and TW3 is illustrated in Example 1. Using the teachings provided herein, the other molecular tweezers described here can readily be prepared by simple modification of these protocols.

Pharmaceutical Formulations and Administration.

In order to carry out certain methods described herein, one or more active agents (e.g., molecular tweezers) are administered to a mammal in need thereof (e.g., a mammal diagnosed as having or at risk for a pathology characterized by amyloidosis (such as the pathologies listed in Table 1)).

The active agent(s) can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

Methods of formulating such derivatives are known to those of skill in the art. For example, acid salts of the active agents can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like.

An acid addition salt can be reconverted to the free base by treatment with a suitable base. Certain typical acid addition salts of the active agents described herein include, for example, halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Certain typical basic salts include, but are not limited to, alkali metal salts, e.g., the sodium salt, and copper salts.

Preparation of esters typically involves functionalization of, e.g., hydroxyl and/or carboxyl groups that are present within the molecular structure of the active agent. In certain embodiments, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

In various embodiments, the active agents identified herein are useful for parenteral, topical, oral, nasal (or otherwise inhaled), rectal, or local administration, such as by aerosol or transdermally, prophylactically and/or therapeutically (e.g., to inhibit the aggregation of amyloidogenic protein(s)) and/or to mitigate one or more symptoms of a disease characterized by amyloidosis and/or to improving quality of life of an individual diagnosed with such a disease or at risk for such a disease.

The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, lipid complexes, etc.

The active agents (molecular tweezers) described herein can also be combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s), to improve penetration of the blood brain barrier (where appropriate), etc. Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds, particularly of use in the preparation of tablets, capsules, gel caps, and the like include, but are not limited to binders, diluents/fillers, disintegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active component or components (e.g., molecular tweezers) and the resulting composition is compressed. Where necessary the compressed product is coated, e.g., known methods for masking the taste or for enteric dissolution or sustained release. Suitable coating materials include, but are not limited to ethyl-cellulose, hydroxymethylcellulose, polyoxyethylene glycol, cellulose acetate phthalate, hydroxypropylmethylcellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain therapeutic or prophylactic applications, the compositions (molecular tweezers) described herein are administered to a mammal (e.g., to a non-human mammal, to a human, to an elderly human, etc.) to prophylactically and/or therapeutically inhibit amyloidosis, and/or to slow the onset, and/or to slow the progression, and/or to mitigate one or more symptoms of a pathology characterized by an amyloidotic process (e.g., a pathology/disease described in Table 1), and/or to otherwise improve the quality of life of an individual developing or having a risk of developing such a pathology. An amount adequate to accomplish this is defined as a "therapeutically effective dose." Amounts effective for this use will depend upon the age of the subject, the geneder of the subject, the particular pathology, the severity of the symptoms, and the general state of the subject's health. Single or multiple administrations of the compositions may be used depending on the dosage and frequency as required and tolerated by the subject. In any event, in various embodiments, the composition should provide a sufficient quantity of the active agents (e.g., molecular tweezers) of this invention to effectively treat (ameliorate one or more symptoms in) the subject.

The amount and/or concentration of active agent(s) can vary widely, and will typically be selected primarily based on activity of the active ingredient(s), body weight and the like in accordance with the particular mode of administration selected and the subject's needs (see, e.g., Remington's Pharmaceutical Science, 15th ed., Mack Publishing Company, Easton, Pa. (1980), Remington: The Science and Practice of Pharmacy, 21st Ed. 2005, Lippincott Williams & Wilkins, and the like). In certain embodiments amounts, however, will typically be selected to provide dosages ranging from about 0.001, 0.01, 0.1 1, or 10 mg/kg/day to about 50 mg/kg/day and sometimes higher. In certain embodiments typical dosages range from about 1 mg/kg/day to about 3 mg/kg/day, preferably from about 3 mg/kg/day to about 10 mg/kg/day, more preferably from about 10 mg/kg/day to about 20.0 mg/kg/day, and most preferably from about 20 mg/kg/day to about 50 mg/kg/day. In certain preferred embodiments, dosages range from about 10 mg/kg/day to about 50 mg/kg/day. In certain embodiments, dosages range from about 20 mg to about 50 mg given orally twice daily. It will be appreciated that such dosages may be varied to optimize a therapeutic and/or prophylactic regimen in a particular subject or group of subjects.

In certain embodiments, the active agents of this invention are administered to the oral cavity. This is readily accomplished by the use of lozenges, aersol sprays, mouthwash, coated swabs, and the like.

In certain embodiments the active agents of this invention are administered systemically (e.g., orally, or as an injectable) in accordance with standard methods well known to those of skill in the art. In certain embodiments, the agents can also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one illustrative embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Other formulations for topical delivery include, but are not limited to, ointments, gels, sprays, fluids, and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

As indicated above, various buccal, and sublingual formulations are also contemplated.

In certain embodiments, particularly in the treatment of neurological pathologies such as Alzheimer's disease it may be desirable to deliver the molecular tweezers to the brain. Where the molecular tweezers are administered systemically, this could require that the active agent(s) cross the blood brain barrier. In various embodiments this is facilitated by coadministering the active agents with carrier molecules such as cationic dendrimers or arginine-rich peptides, which carry the active agents over the BBB. In certain embodiments the active agents can be delivered directly to the brain by the implantation of a biocompatible release system (a reservoir), by direct administration through an implanted canula, by an implanted or partially implanted drug pump, and the like. In certain embodiments the active agents can simply be systemically administered (e.g., injected into a vein) whereby the equilibrium between free monomeric and misfolded Alzheimer's peptide is shifted towards the side of free monomer, which in turn will shift the connected equilibrium in the brain to the "good" side. In certain embodiments it is expected that the molecular tweezers will simply be transported across the blood brain barrier.

In certain embodiments, one or more active agents of the present invention can be provided as a "concentrate", e.g., in a storage container (e.g., in a premeasured volume) ready for dilution, or in a soluble capsule ready for addition to a volume of water, alcohol, hydrogen peroxide, or other diluent.

While the invention is described with respect to use in humans, it is also suitable for animal, e.g., veterinary use. Thus certain preferred organisms include, but are not limited to humans, non-human primates, canines, equines, felines, porcines, ungulates, lagomorphs, and the like.

The foregoing formulations and administration methods are intended to be illustrative and not limiting. It will be appreciated that, using the teaching provided herein, other suitable formulations and modes of administration can be readily devised.

Kits

In various embodiments kits are provided for the treatment methods/uses described herein (e.g., mitigate or prevent the onset of one or more symptoms of a pathology characterized by the formation of amyloid deposits.). In various embodiments such kits typically include a container containing one or more molecular tweezers as described herein. Such kits can, optionally include instruments for formulating or administering the agent(s). with one or more pharmaceutically acceptable excipients.

The kit can, optionally, further comprise one or more other agents used in the treatment of the condition/pathology of interest. Such agents include, but are not limited to, pharmaceuticals routinely prescribed for the treatment or prevention of one or more pathologies characterized by an amyloidotic process (e.g., a pathology described in Table 1).

In addition, the kits optionally include labeling and/or instructional materials providing directions (i.e., protocols) for the practice of the methods or use of the "therapeutics" or "prophylactics" of this invention. Preferred instructional materials describe the use of one or more active agent(s) of this invention to mitigate one or more symptoms of a pathology characterized by an amyloidogenic process and/or to prevent the onset or increase of one or more pathologies or symptoms of such pathologies in a subject diagnosed as having or at risk for the disease. The instructional materials may also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Synthesis of Molecular Tweezers TW1, TW2, and TW3

Figure 2:
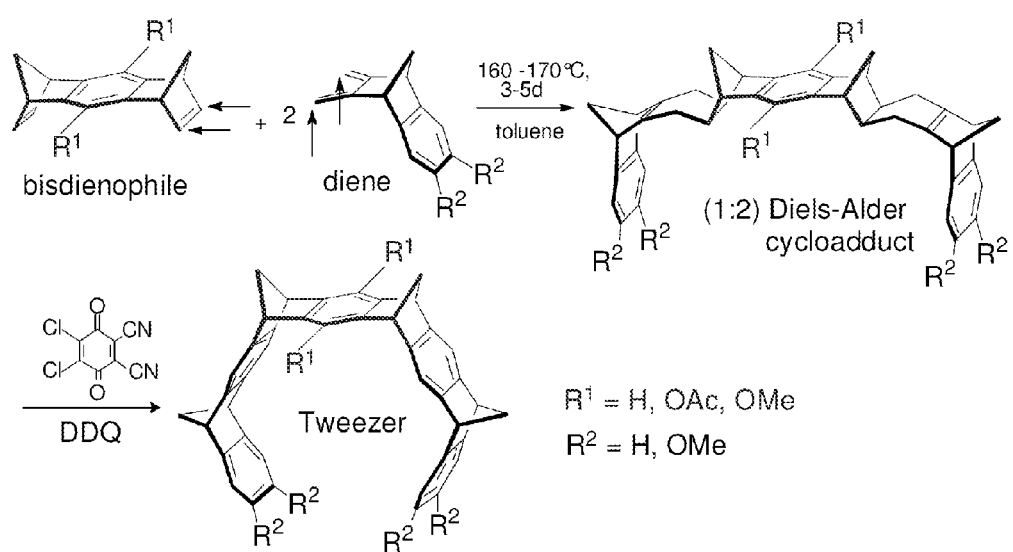
FIG. 2 shows synthesis Scheme 1.

The skeleton of the tetramethylene-bridged molecular tweezers (the starting material of tweezers TW1 and TW2, see, e.g., FIG. 1) can be constructed by repetitive Diels-Alder reactions of exo-5,6-bismethylene-2,3-benzonorbornene as diene with the bisnorbornadienobenzene as bisdieneophile. Subsequent oxidative dehydrogenation of the cyclohexene rings in the (1:2) Diels-Alder cycloadduct with DDQ leads to the molecular tweezers (Scheme 1, FIG. 2) (Klärner, et al. (1999) *Chem. Eur. J.* 5: 1700-1707; Klärner et al. (2001) *Tetrahedron* 57: 3573-3687; Klärner et al. (2004) *Eur. J. Org. Chem.* 7: 1405-1423; Klärner et al. (2008) "Synthesis of molecular tweezers and clips by the use of a molecular Lego set and their supramolecular functions" Chapter 4, page 99-153, in "*Strategies and Tactics in Organic Synthesis*", Vol. 7 (ed. Harmata, M.), Academic Press, Elsevier, Amsterdam).

Figure 3:
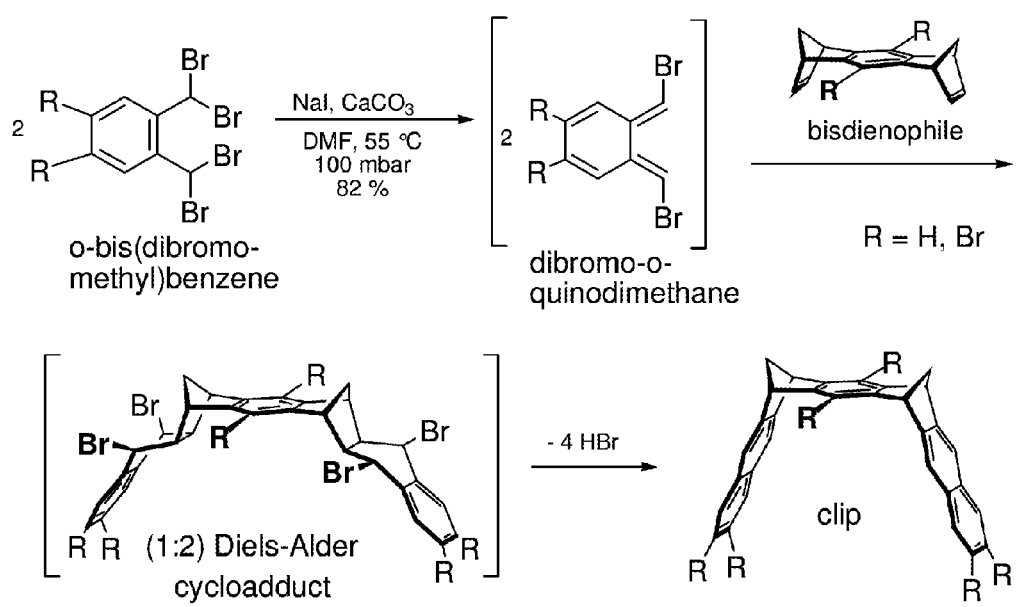
FIG. 3 shows synthesis Scheme 2.

The skeleton of the related dimethylene-bridged molecular clips can be synthesized by repetitive Diels-Alder reactions analogously to the synthesis of the tweezers using dibromo-o-quinodimethane derivatives as diene and the same bisdienophile. In this case the HBr elimination in the (1:2) Diels-Alder cycloadduct occurs under the condition of formation leading to the molecular clips in a one-pot reaction (Scheme 2, FIG. 3).

Figure 4:
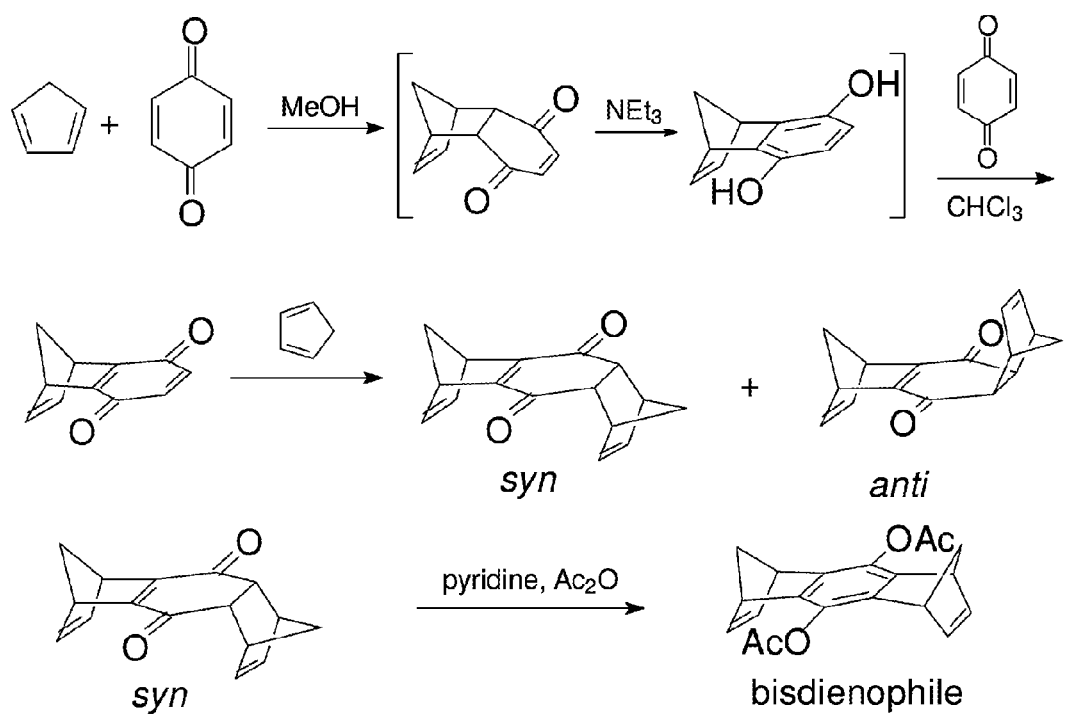
FIG. 4 shows synthesis Scheme 3.

The bisdienophile is the starting material for the synthesis of the tweezers of type TW3. Their preparation starts with a one-pot reaction producing the norbornadienoquinone. The Diels-Alder cycloaddition of 1,3-cyclopentadiene to p-benzoquinone leads to the known (1:1) adduct which isomerizes in the presence of triethylamine to the corresponding hydroquinone that is subsequently oxidized with an excess of p-benzoquinone. The resulting quinone readily reacts with 1,3-cyclopentadiene at −78° C. almost quantitatively leading to a (60:40) mixture of the syn- and anti-Diels-Alder adduct which can be easily separated by recrystallization from toluene. Under basic conditions in the presence of acetic anhydride the syn-adduct is converted to the corresponding diacetoxy-substituted bisdienophile, the starting material of TW3 (Scheme 3, FIG. 4).

Figure 5:
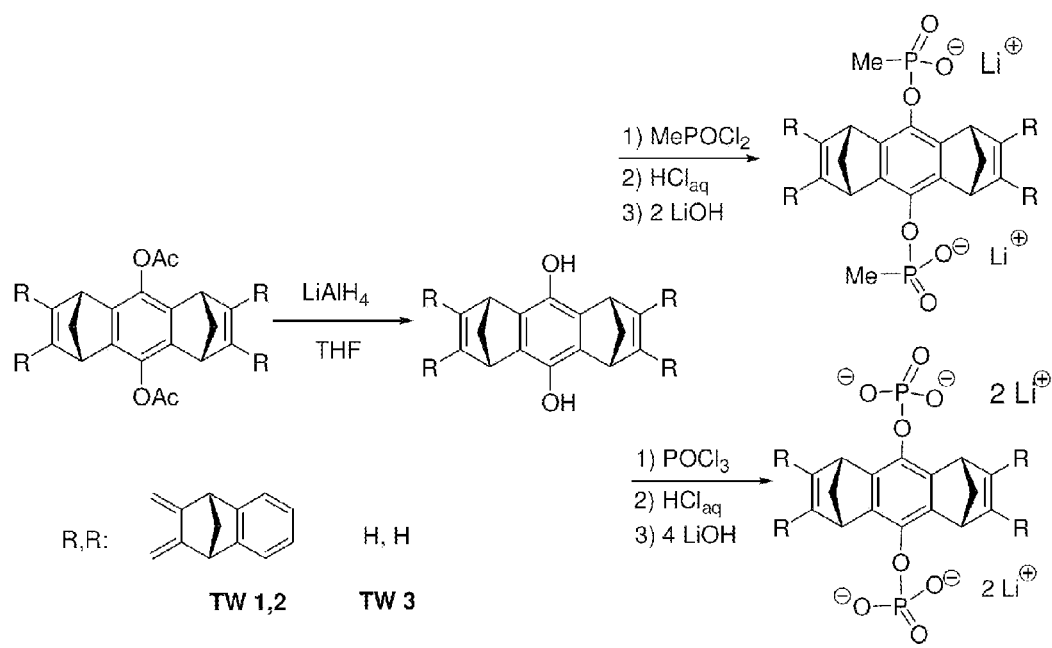
FIG. 5 shows synthesis Scheme 4.

The tweezers TW1-3 substituted by methanephosphonate or phosphate groups in the central benzene ring were prepared by reductive or basic ester hydrolysis of the corresponding diacetoxy derivatives followed by esterification of the hydroquinones with MePOCl$_2$ and POCl$_3$, respectively. Hydrolysis and neutralization of the methanephsphonic acid or phosphoric acid derivatives with lithium hydroxide lead to the desired methanephosphonate or phosphate salts (Scheme 4, FIG. 5) (Fokkens et al. (2005) *Chem. Eur. J.* 11: 477-494; Schrader et al. (2005) *J. Org. Chem.* 70: 10227-10237; Talbiersky et al. (2008) *J. Am. Chem. Soc.* 130: 9824-9828).

Example 2

The amino acid sequence of Aβ contains three positively charged amino acid residues, one Arg and two Lys, that may be involved in Aβ folding and self-assembly[16-24]. Thus, small molecules that bind to these residues are believed to inhibit Aβ oligomerization and toxicity.

Two molecular tweezers (TWw1 and TW2, but not TW3 in FIG. 1) were observed to inhibit Aβ aggregation. Although TW2 was found to inhibit Aβ aggregation, it is a toxic. In contrast, tweezers 1 (TW1) is non-toxic and inhibits both aggregation and toxicity of Aβ. TW1 and TW2 share a horseshoe-like hydrocarbon backbone. TW1 has two phosphate groups at the bridgehead, whereas TW2 has two methylphosphonate groups. TW3 has two methylphosphonate groups attached to a truncated hydrocarbon backbone. These three derivatives allow evaluation of the nature of the hydrocarbon backbone and the bridgehead groups separately.

The effect of the three derivatives on the assembly and toxicity of both Aβ40 and Aβ42 was assessed and is reported below. Aβ40 is ~10-times more abundant than Aβ42. It is deposited mainly in the brain vasculature and is the main cause of CAA, a syndrome that often accompanies AD and leads to death resulting from microhemorrhages. CAA also can occur as the main illness without overt AD. Although Aβ42 is less abundant than Aβ40, it is substantially more toxic and is the main cause for neuronal damage and memory loss in AD.

Figure 6:
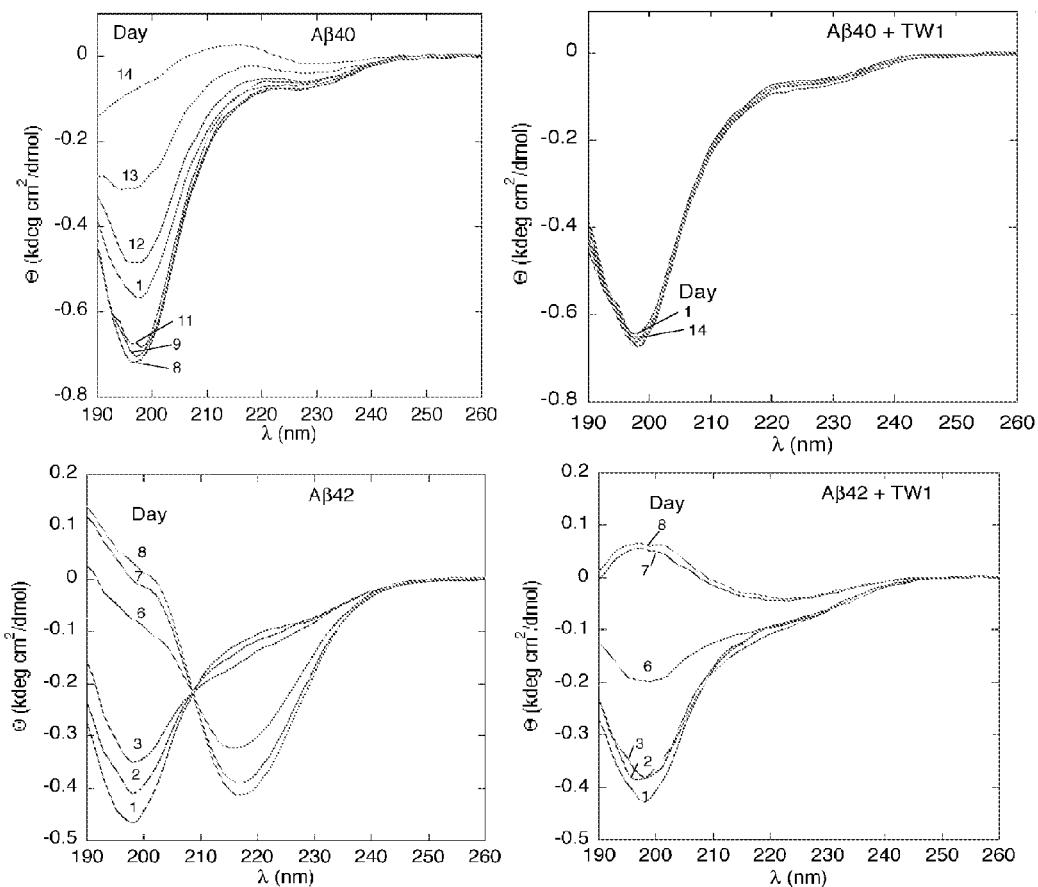
FIG. 6 shows that TW1 inhibits conformational transition of quiescent Aβ measured by CD. Measurements were carried out using a Jasco J-810 spectropolarimeter. Aβ samples were prepared in 10 mM sodium phosphate, pH 7.4, and filtered through a 0.02 μm filter. A) 25 μM Aβ40. B) 25 μM Aβ40+10 μM TW1. C) 30 μM Aβ42. D) 30 μM Aβ42+10 μM TW1. TW1 inhibits β-sheet formation by both Aβ40 and Aβ42.

Our experiments demonstrated the following findings:

1. Under quiescent conditions, TW1 inhibited the transition of Aβ40 and Aβ42 from an unstructured conformation to a structure rich in β-sheet at substoichiometric concentration ratios, as measured by circular dichroism (CD) spectroscopy (FIG. 6). The transition from unstructured conformation to β-sheet is known to accompany Aβ fibril formation (Serpell (2000) *Biochim. Biophys. Acta* 1502: 16-30).

Figure 7:
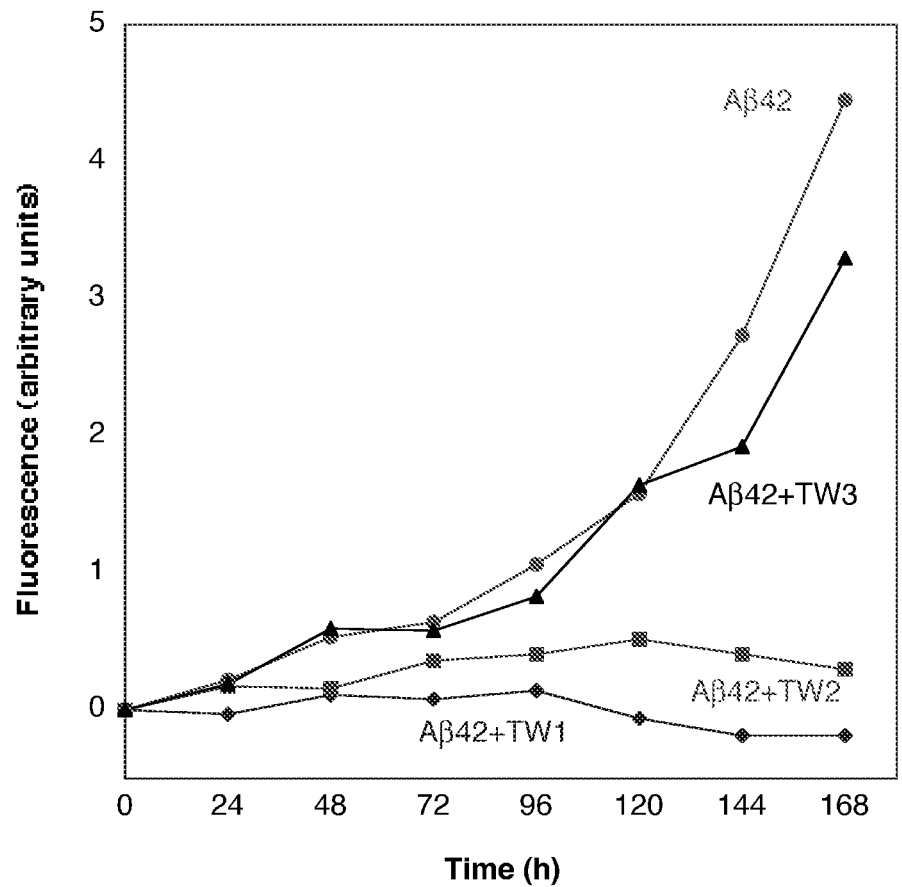
FIG. 7 illustrates inhibition of quiescent Aβ42 conformational transition measured by ThT fluorescence. Aβ42 (25 μM) was incubated in the presence or absence of 20 μM of each tweezers derivative. For ThT fluorescence measurements, 120 μl sample were incubated with 6 μl 100 μM ThT for 90 seconds and measured at λex=450/λem=482). Both TW1 and TW2, but not TW3, inhibit β-sheet formation by Aβ42.

2. Under quiescent conditions, TW1 and TW2, but not TW3, inhibit the transition of Aβ from an unstructured conformation to a structure rich in β-sheet at substoichiometric concentration ratios, as measured by thioflavin T (ThT) binding (LeVine (1993) *Protein Sci.* 2: 404-410) (FIG. 7). This is a corroboration of the findings described in point #1 using an alternative method. Because the tendency of Aβ42 to aggregate and form β-sheet conformation is substantially higher than that of Aβ40, it is safe to extrapolate these results and predict that the same behavior would be observed for the three tweezers derivatives with Aβ40. The data demonstrate that either the phosphate or the methylphosphonate groups support inhibition of Aβ aggregation by the tweezers and that the hydrocarbon skeleton shared by TW1 and TW2, but not TW3, is required for the inhibition.

Figure 8:
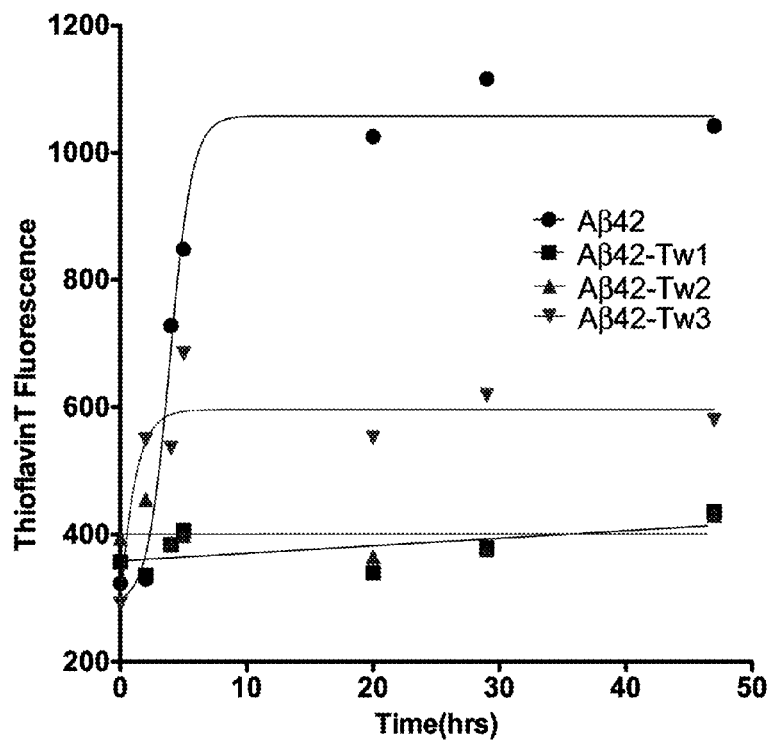
FIG. 8 illustrates inhibition of β-sheet formation by Aβ with shaking. Aβ42 was used at 10 μM. Each sample was pre-treated with HFIP, a reagent that disassembles pre-formed aggregates. Tweezers were dissolved in a 1:1 HFIP:MeOH mixture and added to the Aβ solution in HFIP. The organic solvents were then evaporated to dryness in vacuo. To initiate the aggregation experiment, the peptide or peptide:tweezers solution was dissolved in 60 mM NaOH and then diluted 10-times with 10 mM sodium phosphate, pH 7.4. The samples were shaken at 200 rpm. TW1 and TW2 completely inhibited Aβ42

3. Mechanical agitation is known to facilitate and accelerate Aβ aggregation (Fezoui et al. (2000) *Amyloid* 7: 166-178). Under agitation conditions, at 1:10 Aβ:tweezers concentration ratio, TW1 shows efficient inhibition of β-sheet formation by Aβ40 or Aβ42 but TW3 does not (FIG. 8).

4. Tweezers derivatives inhibit Aβ aggregation as measured by dynamic light scattering (DLS), a technique that measures the size distribution of particles in solution non-invasively, which has been used extensively to study Aβ fibrillogenesis (Lomakin et al. (1999) *Meth. Enzymol.* 309: 429-459; Lomakin et al. (2005) *Methods Mol. Biol.* 299: 153-174). In initial experiments, Aβ:TW1 solutions were prepared at a 1:10 concentration ratio (20 μM Aβ40 or Aβ42) in 10 mM sodium phosphate, pH 7.4. Under these conditions, in the absence of tweezers, Aβ40 initially displays 1-2 nm particles which over time (~1 week) convert into large particles of hydrodynamic radius ($R_H$)>200 nm. Aβ42 initially displays two groups of particles, with $R_H$=8-10 nm and 20-60 nm, which within ~1 week gradually grow into large 200-1000 nm particles. In the presence of 10-fold excess TW1, no particle growth was observed for either Aβ40 or Aβ42 for over a month. In a follow up experiment, solutions of Aβ40 or Aβ42 in the absence or presence of each of the tweezers derivatives were prepared in a similar fashion but at a 1:1 concentration ratio. Under these conditions, in the presence of TW1 or TW2, the Aβ42 fraction of $R_H$=20-60 nm particles was about twice as abundant as in the absence of tweezers. This suggests that the tweezers stabilized an oligomeric Aβ42 fraction, similar to results observed with inositol derivatives (McLaurin et al. (2006) *Nat. Med.* 12: 801-808; McLaurin et al. (2000) *J. Biol. Chem.* 275: 18495-51802), the green tea-derived polyphenol EGCG[15], and C-terminal peptides derived from Aβ42 (Fradinger et al. (2008) *Proc. Natl. Acad. Sci. USA*, 105(37): 14175-14180). Importantly, in all of those cases, the oligomers stabilized by these agents were non-toxic. In the absence of tweezers, this fraction grew in size over a week to yield 200-1000 nm particles, whereas in the presence of TW1 or TW2, particle growth was substantially delayed or not observed at all. In some experiments, a small number of particles of $R_H$~200 nm were observed after 20 days. The data demonstrate that in the presence of TW1 or TW2, initial oligomerization of Aβ into 20-60 nm particles is accelerated and further aggregation is inhibited, suggesting stabilization of non-toxic oligomers.

Figure 9:
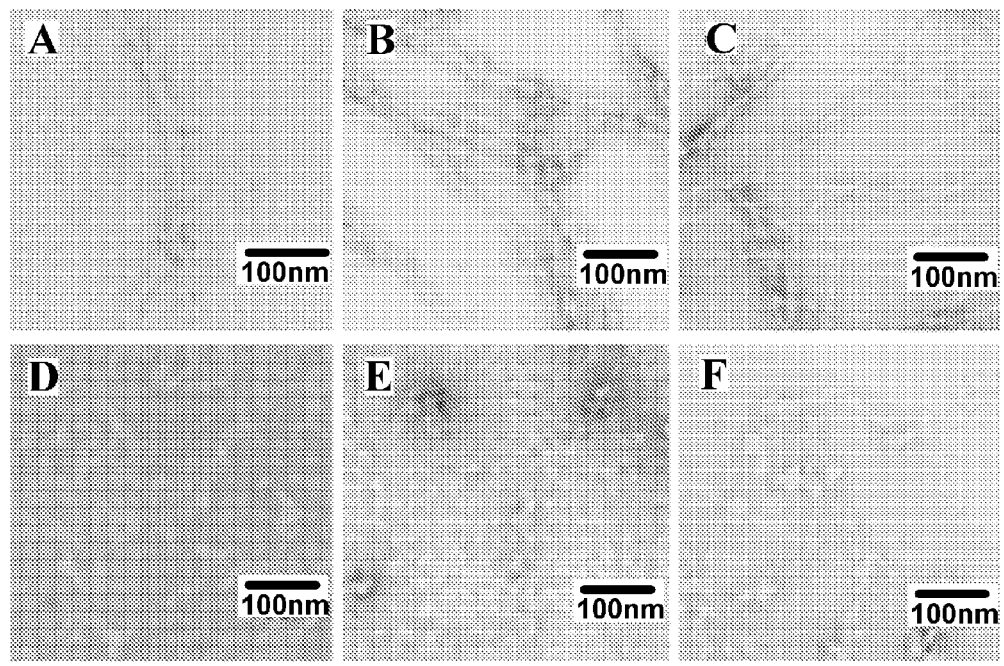
FIG. 9 illustrates attenuation of quiescent Aβ42 fibril formation by TW1 measured by EM. 8 μL of each solution were applied to glow-discharged, carbon-coated Formvar grids and incubated for 20 min. The samples were fixed by incubating with 5 μL of 2.5% glutaraldehyde for 5 min, and stained with 5 μL of 1% uranyl acetate for 5 min. The stained samples were examined using a JEOL CX100 electron microscope. A-C) 25 μM Aβ42. D-F) 25 μM Aβ42+20 μM TW1. A, D) day 3. B, E) day 5. C, F) day 10.

5. TW1 attenuates Aβ fibril formation as measured by electron microscopy (EM). As shown in FIG. 9, under quiescent conditions similar to those used for the ThT experiment discussed in point #2 and shown in FIG. 7, in the absence of tweezers, Aβ42 initially formed a mixture of globular and fibrillar structures, which converted to typical amyloid fibrils within 10 days. In contrast, in the presence of substoichiometric concentrations of TW1, this conversion was delayed substantially.

Figure 10:
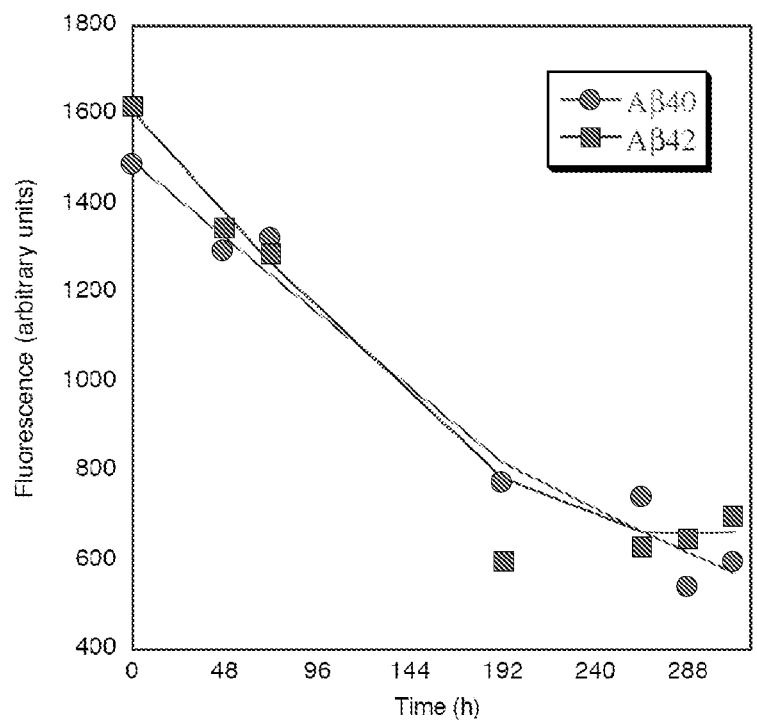
FIG. 10 shows that TW1 disaggregates of pre-formed Aβ fibrils. Fibrils of Aβ40 or Aβ42 were incubated with the TW1 at a ~1:100 nominal concentration ratio (Aβ monomer concentration within fibrils was measured by amino acid analysis) and the amount of β-sheet conformation was determined by ThT fluorescence. TW1 disaggregated both Aβ alloforms within approximately 1 week.

6. TW1 disaggregates pre-existing Aβ40 and Aβ42 fibrils. We incubated 10 μM fibrils of either Aβ40 or Aβ42 with 1 mM TW1 and measured the change in ThT fluorescence over time (FIG. 10). In both cases, the fluorescence signal decreased steadily until it reached a plateau after ~1 week of incubation, demonstrating that TW1 is capable of breaking the β-sheet conformation and disaggregating pre-formed Aβ fibrils.

Figure 11:
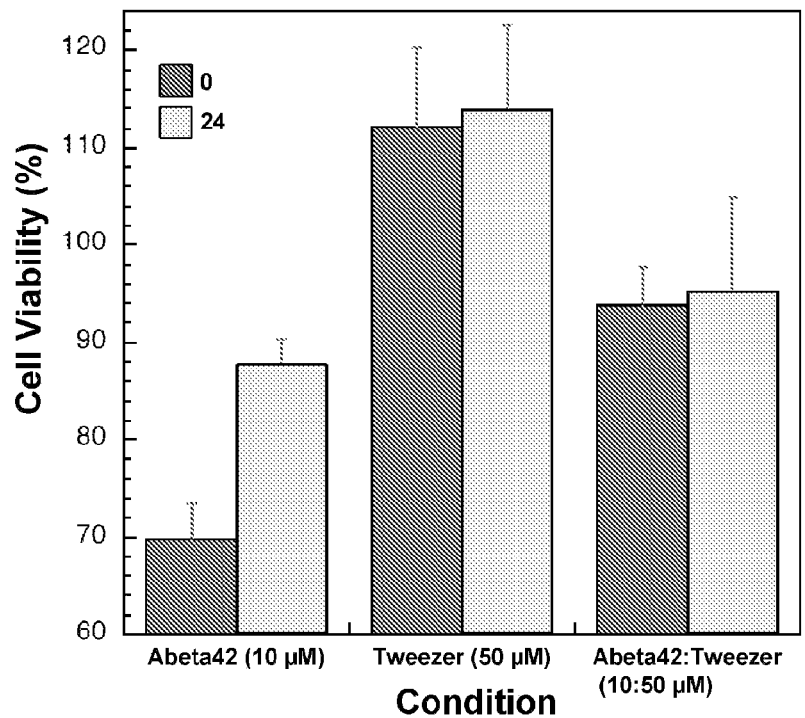
FIG. 11 shows that TW1 inhibits Aβ42-induced toxicity. 10 μM Aβ42, or 50 μM TW1, or a mixture of both, were added to differentiated PC-12 cells. Aβ42 was either freshly prepared (dark bars) or incubated for 24 hours at 37° C. in cell culture medium prior to mixing with TW1 and adding to cells (light bars). Cell viability relative to media control was measured using the MTT assay. Under these conditions, TW1 was found to be nontoxic and to inhibit Aβ42-induced toxicity.
Figure 12:
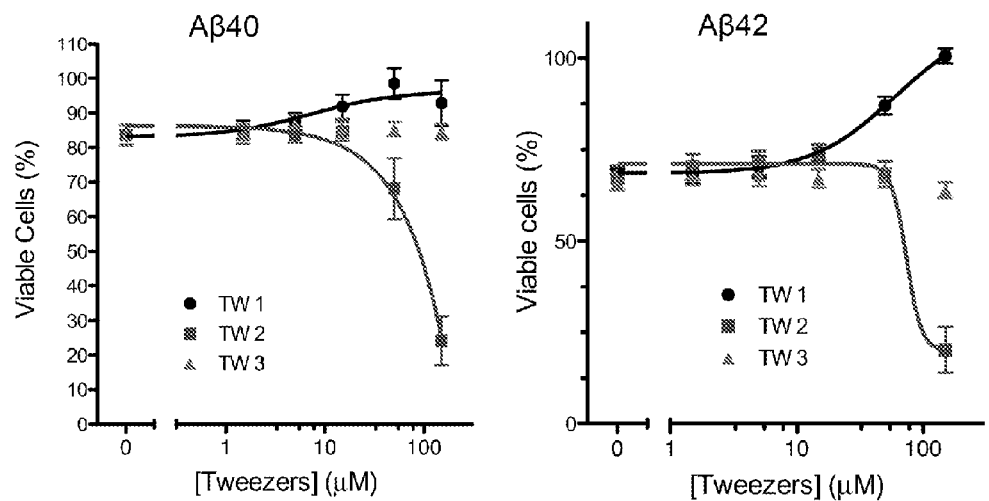
FIG. 12 shows that the tweezers' biological activity is structure-dependent. Freshly prepared 10 μM Aβ40 or Aβ42 were mixed with each of the three tweezers derivatives and added to differentiated PC-12 cells. Cell viability relative to media control was measured using the MTT assay. TW1 was found to inhibit Aβ-induced toxicity dose-dependently, whereas TW2 was found to be toxic at concentrations >10 μM. TW3 was inactive.
Figure 13:
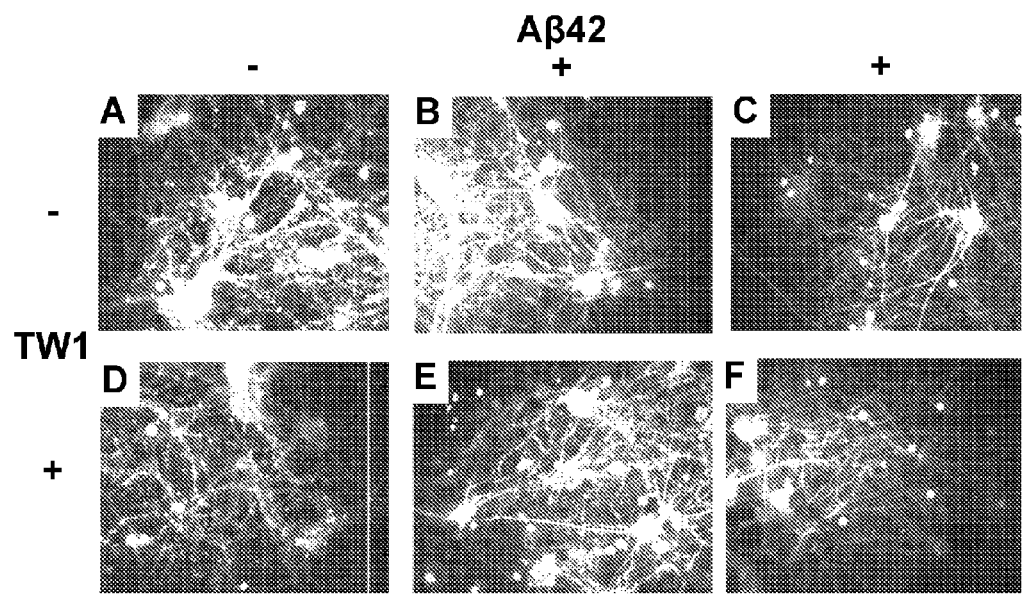
FIG. 13 shows that TW1 rescues Aβ-induced decrease of dendritic spine density. Primary rat hippocampal neurons were treated for 48 h with 500 nM Aβ42 oligomers in the absence or presence of TW1. Neurons were visualized by staining F-actin with phalloidin (red) and nuclei were stained with DAPI (blue). A) Untreated cells show abundant dendritic spines (rough appearance). B and C) Show duplicate fields from the same experiment. Cells incubated with 500 nM Aβ42 oligomers show essential absence of spines (smooth neurites). D) Cells treated with 5 μM TW1 alone show no effect. E) Cells treated with 500 nM Aβ42 oligomerized in the presence of 250 nM TW1 show essentially complete rescue of the toxic effect of Aβ42 oligomers. F) Cells treated with 500 nM pre-formed toxic Aβ42 oligomers (prepared in a similar manner to panels B and C) followed by addition of 5 μM TW1 show a moderate rescue effect of TW1.

7. TW1 inhibits Aβ-induced toxicity in cell culture. Based on the capability of the tweezers to inhibit Aβ aggregation, disaggregate pre-formed Aβ fibrils, and stabilize putatively non-toxic Aβ oligomers, we predicted that they should inhibit Aβ-induced toxicity. To test this prediction, in initial experiments, the effect of 5-fold excess TW1 on Aβ42-induced neurotoxicity was measured by the MTT assay (Datki et al. (2003) *Brain Res. Bull.* 62: 223-229) with differentiated PC-12 cells (Shearman et al. (1994) *Proc. Natl. Acad. Sci. USA* 91: 1470-1474) (FIG. 11). The data demonstrated that freshly prepared Aβ42 (predominantly oligomeric) was more toxic than "aged" Aβ42 (predominantly fibrillar) and TW1 attenuated the toxicity of both forms. Moreover, TW1 itself showed a moderate protective effect at 50 μM, as demonstrated by a 10-15% increase in cell viability relative to the untreated control. Next, we evaluated the dose-dependence of the effect of each of the three tweezers derivatives on Aβ40 and Aβ42 using the same cell culture system. Aβ42 was used at 10 μM as in the previous experiment, whereas the less neurotoxic Aβ40 was used at 25 μM. TW1, TW2, or TW3 were used at concentrations between 0.1-100 μM. PC-12 cells were differentiated for 48 hours prior to the start of the assay. TW1 was found to inhibit Aβ40- and Aβ42-induced toxicity with $IC_{50}$ values of 7 μM and 60 μM, respectively (FIG. 12). The difference in the inhibitory activity towards the two Aβ alloforms is in agreement with the difference in their intrinsic toxicity, i.e., 9-10 times more TW1 is required to inhibit the substantially more toxic Aβ42 (Dahlgren et al. (2002) *J. Biol. Chem.* 277: 32046-32053). As expected, TW3 was found to be inactive. Importantly, TW2, not only did not inhibit Aβ toxicity but also was found to be toxic itself at concentrations above 10 μM, killing ~80% of the cells at 100 μM. This finding is surprising in view of the relatively small structural difference between TW1 and TW2. This result is particularly important because it demonstrates that the activity of tweezers as inhibitors of Aβ toxicity does not necessarily correlate with their ability to inhibit Aβ assembly. Based on the data extant, prediction of inhibitory activity based on tweezers structure alone is impossible. Thus, using molecular tweezers as inhibitors of Aβ toxicity is by no means trivial.

8. TW1 rescues synapse structure and activity. An early neurotoxic event induced by Aβ oligomers and believed to be a predominant pathologic mechanism causing amnestic mild cognitive impairment (MCIa) and early AD[1] is disruption of synapse morphology and communication (Shankar et al. (2007) *J. Neurosci.* 27: 2866-2875). To evaluate the capability of TW1 to rescue these effects, we used dendritic spine morphology and electrophysiologic assay paradigms. To measure the effect of TW1 on Aβ42-induced decrease in dendritic spine density, rat primary hippocampal neurons were treated for 48 h with Aβ42 oligomers prepared according to Kayed et al. (2003) *Science* 300: 486-489, in the absence or presence of TW1 (FIG. 14). Aβ42 oligomers caused essentially complete depletion of dendritic spines (FIG. 14, panels B, C) compared to control (FIG. 14, panel A). When incubated with Aβ42 during the preparation of oligomers, TW1 rescued this toxic effect to baseline level at substoichiometric concentrations (FIG. 14, panel E). Addition of 10-fold excess TW1 together with pre-formed neurotoxic Aβ42 oligomers prepared in the absence of TW1 showed a moderate effect (FIG. 14, panel F). TW1 itself at 5 μM had no effect on dendritic spine morphology (FIG. 14, panel D). In addition, TW1 was found to rescue Aβ42-mediated inhibition of miniature excitatory postsynaptic currents (mEPSCs) in primary mouse hippocampal neurons (FIG. 14). After establishing a stable baseline recording for 5 min, cells were perfused with vehicle, Aβ42, or a 1:10-Aβ42:TW1 mixture. At 3 μM, Aβ42 was found to induce robust inhibition of mEPSCs, reducing spike frequency by ~70% relative to baseline level within 20 min. This effect endured after the 15-min washing period. In the presence of 10-fold excess TW1, this effect was rescued to baseline level.

9. Initial in vivo experiments show improvement in cognitive ability in a transgenic mouse model of AD. The model used is a mouse overexpressing three mutant human genes, PS1(M146V), APP(Swe), and tau(P301L) (Oddo et al. (2003) *Neuron* 39: 409-421), each of which causes severe early-onset familial AD in humans. Nine-month old mice were divided into three groups: A control group (n=6) that received vehicle only, and two treatment groups that were treated with 500 μM (n=7) or 1 mM (n=5) TW1 subcutaneously over a period of 4 weeks using miniosmotic pumps. Before and after the treatment, the mice were examined using the Y-maze paradigm (Lalonde (2002) *Neurosci. Biobehav. Rev.* 26: 91-104). Analysis of the percent alternations (defined as the normalized number of complete entry cycles to all arms divided by the total number of entries to any arm), showed an improvement of 21% and 16% for the 500 μM and 1 mM groups, respectively (FIG. 15). The improvement in the spatial memory of the mice in the two treatment groups is to the same level of untreated non-transgenic mice. It is also similar to, or even larger than, the difference observed using Y-maze between another AD transgenic mouse line (Tg2576) and wild-type mice (Ognibene et al. (2005) *Behav. Brain Res.* 156: 225-232; King and Arendash (2002) *Physiol. Behav.* 75: 627-642).

10. TW1 likely binds first to Lys16 and then to Lys28 of Aβ. TW1 (and similar molecular tweezers) are expected to bind to Aβ at peptide:tweezers stroichiometry up to 1:3 because Aβ contains one Arg (at position 5) and two Lys residues (positions 16 and 28). We have shown that tweezers have substantially higher affinity for Lys than for Arg (unpublished results). Therefore, we expected that the tweezers would bind first to the Lys residues and then to the single Arg. An interesting question is whether the tweezers bind to one of the Lys preferentially. If Lys28 interacts with residues 22-24 and stabilizes a turn as predicted by Teplow et al. (Lazo et al. (2005) *Protein Sci.* 14: 1581-1596; Grant et al. (2007) *Proc. Natl. Acad. Sci. USA* 104: 16522-16527; Cruz et al. (2005) *Proc. Natl. Acad. Sci. USA* 102: 18258-18263; Baumketner et al. (2006) *Protein Sci.* 15: 1239-1247), likely, it would be less available for interaction with the molecular tweezers. To determine the binding site of the tweezers, we used mass spectrometry (MS) in conjunction with electron capture dissociation (ECD) (Xie et al. (2006) *J. Am. Chem. Soc.* 128: 14432-14433), a state-of-the-art technique that enables detection of protein fragments associated non-covalently with small molecule ligands while dissociating peptide bonds. When 50 μM Aβ40 mixed with TW1 at 1:2 concentration ratio, respectively, in 100 mM ammonium bicarbonate, pH 7.6, was electrosprayed into a Q-TOF mass-spectrometer (Synapt, Waters) through a nanospray emitter (Proxeon Biosystem), complexes with up to 1:3—Aβ:tweezers stoichiometry, respectively, were observed and the 1:2 complex predominated (FIG. 16A). In contrast, when a 1:1 mixture was sprayed under similar conditions, the predominant complex had a 1:1 stroichiometry (not shown). This complex was subjected to ECD fragmentation and tandem MS analysis. Following fragmentation, TW1-bound Aβ40 generated fragments of the c (N-terminus containing peptides) and z (C-terminus containing peptides) series. Some of those fragments corresponded to free peptide whereas others were bound to TW1. Absence of TW1-bound fragments N-terminal to His14 and C-terminal to Asp23 suggested that TW1 was bound within the Aβ(14-23) region, most likely at Lys16.

Binding of TW1 in the order Lys16, then Lys28, and finally Arg5 has been corroborated by solution-state NMR experiments (FIG. 17). Heteronuclear single quantum coherence (HSQC) experiments using uniformly $^{15}$N-labeled Aβ40 showed that upon addition of TW1 at 2:1 concentration ratio, respectively, the resonance intensities of Lys16, Leu17, and Gln15 (both backbone and side chain) were reduced substantially. Slight movement and reduction in the intensity of Asn27, Lys28, and Gly29 also were observed. Increasing the Aβ40:TW1 concentration ratio to 1:2, respectively, resulted in disappearance of the peaks of residues 15-17, chemical shift alteration and reduction in peak intensities of multiple residues surrounding Lys28, and milder similar effects around Arg5. These data clearly demonstrate the order of TW1 binding to Aβ is Lys16, followed by Lys28, and finally, Arg5. The preferential binding to Lys16 likely represents the higher exposure of this residue relative to Lys28, which is involved in interactions with Glu22/Asp23 and Val24. Binding to Arg5 occurs last because the affinity of tweezers for Arg is substantially lower than for Lys.

Tweezers inhibit aggregation of amyloidogenic proteins other than Aβ. Based on the observations that tweezers inhibit Aβ assembly and toxicity, we have begun testing the tweezers for inhibition of other proteins that are known to aggregate and cause amyloidosis. Initial experiments evaluated the effect of TW1 on 5 such proteins: 1) calcitonin, aggregation of which is associated with medullary carcinoma of the thyroid (Dammrich et al. (1984) *Histochemistry* 81: 369-372); 2) β$_2$-microglobulin (β2m), which causes dialysis-related amyloidosis in patients with diabetes mellitus (Floege and Ehlerding (1996) *Nephron* 72: 9-26); 3) insulin, which is associated injection-related amyloidosis (Swift (2002) *Diabet. Med.* 19: 881-882); 4) islet amyloid polypeptide (IAPP), aggregation of which causes type 2 diabetes mellitus (Johnson et al. (1989) *N. Engl. J. Med.* 321: 513-518); and 5) the neurotoxic prion protein (PrP) fragment 106-126 (Ettaiche (2000) *J. Biol. Chem.* 275: 36487-36490). Of these proteins, β2m and insulin contain both Lys and Arg, calcitonin and PrP(106-126) contain one Lys but no Arg, and IAPP contains one Arg but no Lys. In PrP(106-126) the single Lys residue is at the very N-terminus (residue 106). The effect of TW1 on the fibrillogenesis and the kinetics of β-sheet formation of these proteins was assessed by EM and ThT fluorescence (FIG. 18). An exception was PrP(106-126), pre-formed fibrils of which did not bind ThT, and therefore its aggregation kinetics was studied using a turbidity assay (Jarrett and Lansbury (1992) *Biochemistry* 31: 12345-12352). TW1 inhibited the fibrillogenesis of calcitonin, β2m, insulin, and IAPP, but not PrP (106-126), suggesting that the presence of a single Lys or Arg residue within the sequence is sufficient for inhibition, unless it is distal to the aggregating core of the protein. Likely, in the first 4 proteins, TW1 binds sufficiently close to sequences that aggregates and form β-sheets, and thereby interferes with self-association and conformational transition of these sequences. In contrast, the data suggest that in PrP(106-126) the N-terminal Lys106 is far from the regions that control self-association and therefore binding of TW1 does not interfere with aggregation.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A molecular tweezers, said molecular tweezers having one of the formulas I-IV:

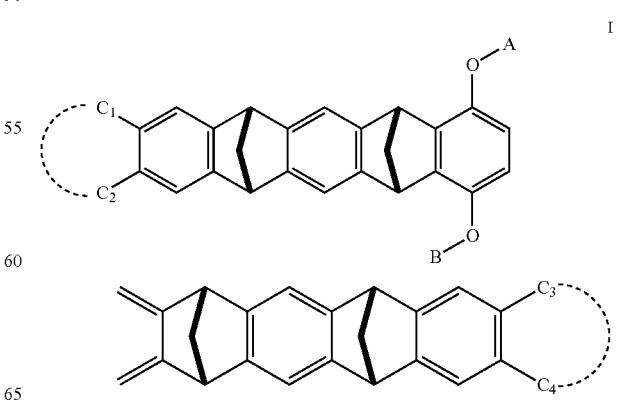

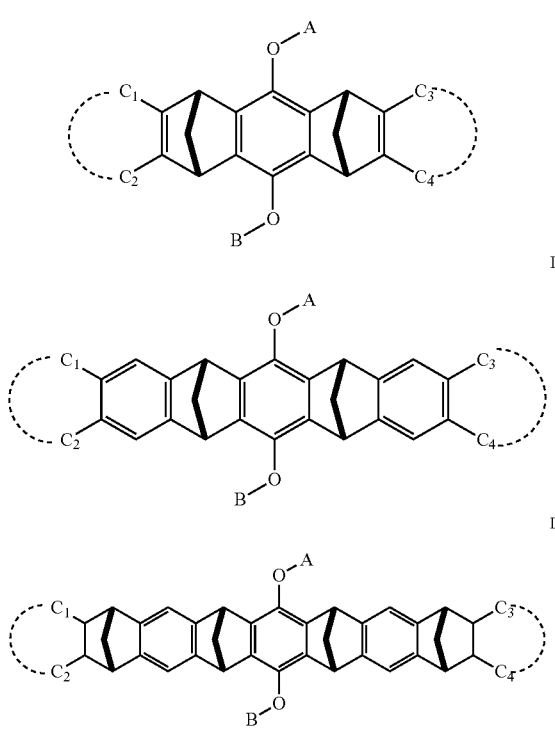

or a salt thereof, where:
- $C^1$, $C^2$, $C^3$, and $C^4$ are independently selected from the group consisting of H, Cl, Br, I, OR, $NR_2$, $NO_2$, $CO_2H$, and $CO_2R$, where R is alkyl, aryl, or H; or
- $C^1$ and $C^2$ and/or $C^3$ and $C^4$ form an aliphatic or aromatic ring;
- A is selected from the group consisting of phosphate, hydrogen phosphate, alkylphosphamide, arylphosphamide, sulfate, and alkylcarboxylate;
- B is selected from the group consisting of phosphate, hydrogen phosphate, alkylphosphonate, arylphosphonate, alkylphosphamide, arylphosphamide, and sulfate, or B has the formula:

—X—S—Y—Z where:
- X is present or absent and when present is —(C=O)—;
- S is a spacer;
- Y is selected from the group consisting of an ester, an amide, a urethane, and a sulfonic ester link; and
- Z is selected from the group consisting of a detectable label, a protein, a nucleic acid, a sugar, and a glycoprotein; and
- said molecular tweezers does not have the formula of TW2.

2. The molecular tweezers of claim 1, wherein said tweezers has Formula I or Formula II.

3. The molecular tweezers of claim 1, wherein $C^1$, $C^2$, $C^3$, and $C^4$ are the same.

4. The molecular tweezers of claim 1, wherein $C^1$, $C^2$, $C^3$, and $C^4$ are H.

5. The molecular tweezers of claim 1, wherein B is selected from the group consisting of phosphate, hydrogen phosphate, alkylphosphonate, arylphosphonate, alkylphosphamide, arylphosphamide, and sulfate.

6. The molecular tweezers of claim 5, wherein A is selected from the group consisting of

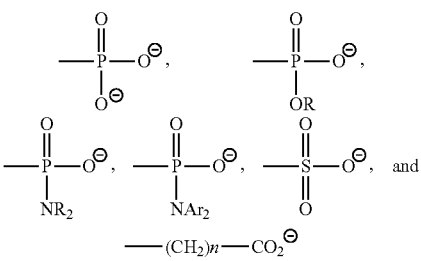

where R is alkyl, or H; n ranges from 1 to 10, and Ar is aryl.

7. The molecular tweezers of claim 1, wherein B is selected from the group consisting of

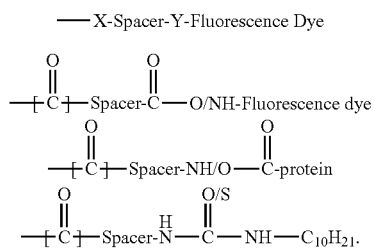

8. The molecular tweezers of claim 6, wherein A and B are the same.

9. The molecular tweezers of claim 1, wherein said molecular tweezers has the formula:

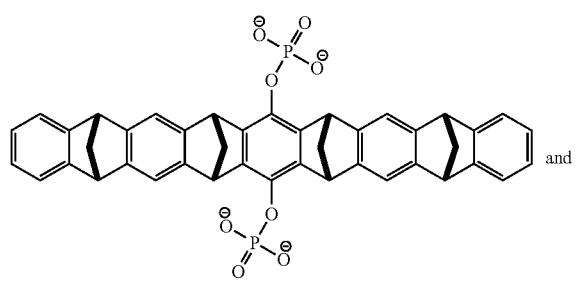

or a salt thereof.

10. The molecular tweezers of claim 1, wherein said molecular tweezers is attached to a second molecular tweezers.

11. A pharmaceutical formulation comprising the molecular tweezers of claim 1 and a pharmaceutically acceptable excipient.

12. The formulation of claim 11, wherein said formulation is formulated for administration via a route selected from the group consisting of intraperitoneal administration, topical administration, oral administration, inhalation administration, transdermal administration, subdermal depot administration, sub-dural administration, and rectal administration.

13. The formulation of claim 11, wherein said formulation is a unit dosage formulation.

* * * * *